United States Patent
Hogaboam et al.

(10) Patent No.: US 11,397,178 B2
(45) Date of Patent: Jul. 26, 2022

(54) METHOD OF PREDICTING PROGRESSION OF IDIOPATHIC PULMONARY FIBROSIS AND MONITORING OF THERAPEUTIC EFFICACY

(71) Applicant: Cedars-Sinai Medical Center, Los Angeles, CA (US)

(72) Inventors: Cory Hogaboam, Los Angeles, CA (US); David Habiel, Los Angeles, CA (US)

(73) Assignee: Cedars-Sinai Medical Center, Los Angeles, CA (US)

(*) Notice: Subject to any disclaimer, the term of this patent is extended or adjusted under 35 U.S.C. 154(b) by 216 days.

(21) Appl. No.: 16/344,313

(22) PCT Filed: Oct. 25, 2017

(86) PCT No.: PCT/US2017/058241
§ 371 (c)(1),
(2) Date: Apr. 23, 2019

(87) PCT Pub. No.: WO2018/081236
PCT Pub. Date: May 3, 2018

(65) Prior Publication Data
US 2019/0271689 A1 Sep. 5, 2019

Related U.S. Application Data

(60) Provisional application No. 62/414,443, filed on Oct. 28, 2016.

(51) Int. Cl.
| | |
|---|---|
| G01N 33/50 | (2006.01) |
| A61K 39/395 | (2006.01) |
| C07K 7/06 | (2006.01) |
| C07K 7/08 | (2006.01) |
| A61P 43/00 | (2006.01) |

(52) U.S. Cl.
CPC ..... *G01N 33/5088* (2013.01); *A61K 39/3955* (2013.01); *A61P 43/00* (2018.01); *C07K 7/06* (2013.01); *C07K 7/08* (2013.01); *G01N 2333/7158* (2013.01); *G01N 2800/12* (2013.01); *G01N 2800/52* (2013.01)

(58) Field of Classification Search
None
See application file for complete search history.

(56) References Cited

U.S. PATENT DOCUMENTS

| | | |
|---|---|---|
| 2010/0233705 A1 | 9/2010 | Arao et al. |
| 2012/0282276 A1 | 11/2012 | Hogaboam et al. |
| 2012/0329666 A1 | 12/2012 | Steele et al. |
| 2014/0087362 A1 | 3/2014 | Szalay et al. |
| 2016/0230226 A1 | 8/2016 | Abbas et al. |
| 2019/0270821 A1* | 9/2019 | Yarranton .......... C07K 16/2866 |

FOREIGN PATENT DOCUMENTS

WO 2018081236 A1 5/2018

OTHER PUBLICATIONS

International Search Report and Written Opinion of PCT/US2017/058241, dated Jan. 29, 2018, 13 Pages.
Crooks et al., Inflammation and Pulmonary Fibrosis, 2012, Chapter 5, Inflammatory Diseases—Immunopathology, Clinical and Pharmacological Bases, 32 Pages.
Englinger et al., Acquired Nintedanib Resistance in FGFR1-Driven Small Cell Lung Cancer: Role of Endothelin-A Receptor-Activated ABCB1 Expression, 2016, Oncotarget, vol. 7(31), pp. 50161-50179.
English et al., Inflammation of the Respiratory Tract is Associated with CCL28 and CCR10 Expression in a Murine Model of Allergic Asthma, 2006, Immunol. Lett., vol. 103(2), pp. 92-100.
Habiel et al., Characterization of Profibrotic EphA3 Expressing Cells in IPF Lungs, 2016, Plenary Scientific Session 5, QJM: An Int'l J. of Medicine, vol. 109(Suppl_1):S9, Conclusion, 2 Pages.
Richeldi et al., Nintedanib in Patients with Idiopathic Pulmonary Fibrosis: Combined Evidence from the TOMORROW and INPULSIS Trials, 2016, Respiratory Medicine, vol. 113, pp. 74-79.
Swords et a., KB004, A Novel Non-Fucosylated Humaneered Antibody, Targeting EphA3, is Active and Well Tolerated in a Phase I/II Study of Advanced Hematologic Malignancies, 2014, Blood, vol. 124(21), 3 Pages.

* cited by examiner

*Primary Examiner* — Daniel C Gamett
(74) *Attorney, Agent, or Firm* — Nixon Peabody LLP; Linda B. Huber

(57) ABSTRACT

The present invention describes methods of monitoring the efficacy of a pulmonary fibrosis, such as idiopathic pulmonary, fibrosis (IPF), treatment. Also described are methods of predicting the progression of IPF. These methods are based, at least in part, on the presence and/or level of CCR10-positive cells.

14 Claims, 36 Drawing Sheets

FIG. 26

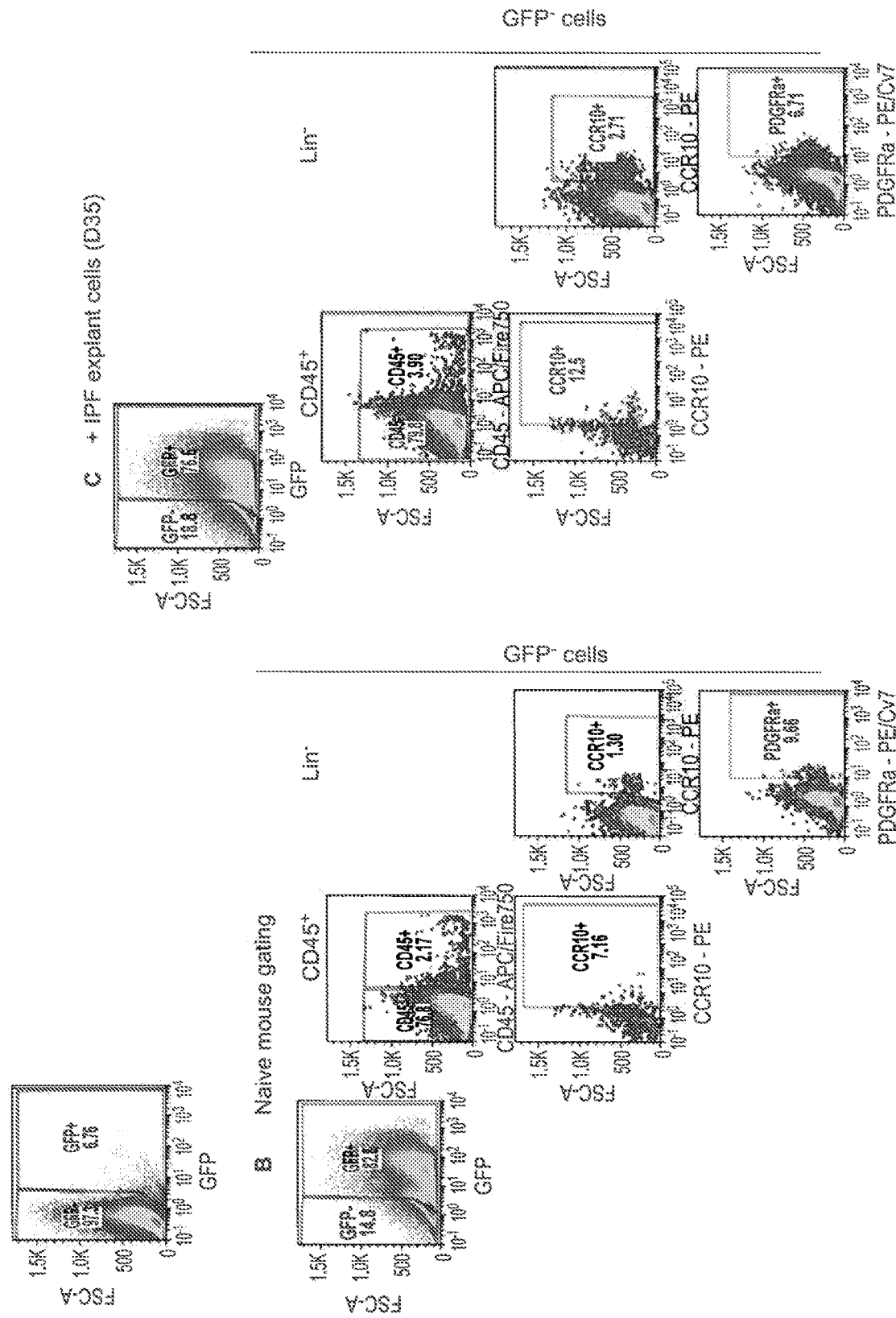

US 11,397,178 B2

METHOD OF PREDICTING PROGRESSION OF IDIOPATHIC PULMONARY FIBROSIS AND MONITORING OF THERAPEUTIC EFFICACY

CROSS-REFERENCE TO RELATED APPLICATIONS

This application is a National Phase of International Application No. PCT/US2017/058241 filed Oct. 25, 2017, currently pending, which designated the U.S. and that International Application was published under PCT Article 21(2) in English, which also includes a claim of priority under 35 U.S.C. § 119(e) to U.S. provisional patent application No. 62/414,443 filed Oct. 28, 2016, the entirety of which is hereby incorporated by reference.

STATEMENT REGARDING FEDERALLY-SPONSORED RESEARCH

This invention was made with Government support under Grant Nos. HL123899 and HL073728 awarded by the National Institutes of Health. The Government has certain rights in the invention.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Idiopathic Pulmonary Fibrosis (IPF) is the most common clinical form of Interstitial Lung Disease (ILD), with poor prognosis, median survival at 3-5 years after diagnosis, and limited pharmacological intervention. Recently, two new therapeutics have been FDA approved for the treatment of IPF patients, OFEV and ESBRIET, both of which were effective at slowing down, but not halting, disease progression.

One major challenge in designing therapeutics for IPF is the lack of a known cause and a sensitive biomarker to monitor disease outcome. It is speculated that persistent lung injury leads to alveolar epithelial cell injury and death, and subsequent aberrant repair mechanism(s) ablates the alveolus. The origin of epithelial injury in IPF is currently controversial; however, several reports have suggested various sources including pathogens, ER stress and immune activation.

Accordingly, there remains a need in the art for options to predict pulmonary fibrosis, including IPF progression and monitor the efficacy of therapies used to treat pulmonary fibrosis.

SUMMARY OF INVENTION

The following embodiments and aspects thereof are described and illustrated in conjunction with compositions and methods which are meant to be exemplary and illustrative, not limiting in scope.

Various embodiments of the present invention provide for a method of determining the efficacy of a pulmonary fibrosis treatment, and optionally treating pulmonary fibrosis, comprising: obtaining a biological sample from a subject; detecting the number of CCR10-positive cells in the biological sample; comparing the number of CCR10-positive cells in the biological sample to the subject's baseline value or to a reference value; determining that the pulmonary fibrosis treatment is effective in the subject if the number of CCR10-positive cells is the same as the subject's baseline value, is less than the subject's baseline value, or is less than the reference value, or determining that the pulmonary fibrosis treatment is ineffective in the subject if the number of CCR10-positive cells is higher the reference value.

In various embodiments, method can comprise treating pulmonary comprising: administering the pulmonary fibrosis treatment to a subject who has been determined that the pulmonary fibrosis treatment is effective, or stopping the administration of the pulmonary fibrosis treatment to a subject who has been determined that the pulmonary fibrosis treatment is ineffective.

Various embodiments of the present application provide for a method of treating pulmonary fibrosis, comprising: requesting or obtaining the results regarding the number of CCR10-positive cells in a biological sample obtained from the subject; determining that a pulmonary fibrosis treatment is effective in the subject if the number of CCR10-positive cells is the same as the subject's baseline value, is less than the subject's baseline value, or is less than the reference value, and administering the pulmonary fibrosis treatment, or determining that the pulmonary fibrosis treatment is ineffective in the subject if the number of CCR10-positive cells is higher the reference value, and stopping the administration of the pulmonary fibrosis treatment.

In various embodiments, the results can be obtained by a method comprising: obtaining a biological sample from a subject; detecting the number of CCR10-positive cells in the biological sample; comparing the number of CCR10-positive cells in the biological sample to a reference value; determining that the pulmonary fibrosis treatment is effective in the subject if the number of CCR10-positive cells is the same as the subject's baseline value, is less than the subject's baseline value, or is less than the reference value, or determining that the pulmonary fibrosis treatment is ineffective in the subject if the number of CCR10-positive cells is higher the reference value.

Various embodiments of the present application provide for a method of treating pulmonary fibrosis, comprising: administering a pulmonary fibrosis treatment to a subject who has been diagnosed that the pulmonary fibrosis treatment is effective by a method comprising: obtaining a biological sample from a subject; detecting the number of CCR10-positive cells in the biological sample; comparing the number of CCR10-positive cells in the biological sample to the subject's baseline value or to a reference value; determining that the pulmonary fibrosis treatment is effective in the subject if the number of CCR10-positive cells is the same as the subject's baseline value, is less than the subject's baseline value, or is less than the reference value, or determining that the pulmonary fibrosis treatment is ineffective in the subject if the number of CCR10-positive cells is higher the reference value.

Various embodiments of the present application provide for a method of predicting progression of pulmonary fibrosis, and optionally selecting a pulmonary fibrosis treatment, comprising: obtaining a biological sample from a subject; detecting the number of CCR10-positive cells in the biological sample; comparing the number of CCR10-positive cells in the biological sample to the subject's baseline value or to a reference value; and predicting a faster progression of pulmonary fibrosis if the number of CCR10-positive cells are higher than the reference value, or predicting a slower progression of pulmonary fibrosis if the number of CCR10-positive cells are lower than the reference value.

In various embodiments, the method can comprise selecting a pulmonary fibrosis treatment, comprising: selecting an experimental pulmonary fibrosis (PF) treatment if the subject is predicted to have a faster progression of pulmonary fibrosis, or selecting a standard pulmonary fibrosis treatment if the subject is predicted to not have a faster progression of pulmonary fibrosis.

In various embodiments of these inventive methods, the pulmonary fibrosis can be idiopathic pulmonary fibrosis (iPF).

In various embodiments of these inventive methods, the pulmonary fibrosis treatment for CCR10+ cells can be an anti-EphA3 antibody.

In various embodiments of these inventive methods, the pulmonary fibrosis treatment CCR10+ cells can be antibody KB004.

Various embodiments of the present invention provide for a method of detecting a change in the number of CCR10+ cells in a subject having or suspected of having idiopathic pulmonary fibrosis, comprising: detecting the number of CCR10-positive cells in a biological sample from the subject; comparing the number of CCR10-positive cells in the biological sample to the subject's baseline value or to a reference value; and determining an increase or decrease in the number of CCR10-positive cells in the biological sample.

In various embodiments, the method can comprise first obtaining the biological sample from the subject having or suspected of having idiopathic pulmonary fibrosis.

In various embodiments, detecting the number of CCR10-positive cells can comprise using an assay selected from the group consisting of flow cytometry, enzyme-linked immunosorbent assay (ELISA), immunohistochemistry, fluorescence in situ hybridization (FISH), radioimmuno assay, and affinity purification, transcript analysis, qPCR, RNA sequencing, and affymetrix array.

Various embodiments of the present invention provide for a method of detecting resistance to nintedanib in a subject having idiopathic pulmonary fibrosis, comprising: detecting the number of CCR10-positive cells in a biological sample obtained from the subject; comparing the number of CCR10-positive cells in the biological sample to the subject's baseline value or to a reference value; determining an increase or decrease in the number of CCR10-positive cells in the biological sample; and determining resistance to nintedanib if there is an increase in the number of CCR10-positive cells in the biological sample.

In various embodiments, the method can comprise first obtaining the biological sample from the subject having or suspected of having idiopathic pulmonary fibrosis.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

FIG. 26 shows transcript expression of tyrosine kinases that are resistant to nintedanib in IPF lung biopsies. Publicly-available transcriptomic datasets were analyzed using Geo2R and uploaded onto ingenuity's Integrated Pathway Analysis (IPA). Tyrosine kinases not inhibited by BIBF1120 were added into a custom pathway designer in ingenuity IPA. Fold changes and p-values of transcript expression for these kinases in IPF compared with normal lung biopsies (GSE24206) is shown. Up- and down-regulated transcripts are depicted in red and green, respectively. Top and bottom values depict p-values and fold changes in expression, respectively, n=6 normal, and n=6 IPF lung biopsies.

FIG. 36 shows GFP-NSG flow cytometric gating strategy. Human GFP$^+$ cells were detected in GFP-NSG mice at day 35 after IPF cell injection using flow cytometry. (A) GFP$^-$ mouse cells from wikitype mice were used to determine both the GFP$^+$ and GFP$^-$ gates. (B) Human CD45, EpCAM, CCR10, and PDGFRα gates were determined based upon any background staining observed with the anti-human antibodies in non-humanized mice. (C) Depicted are representative flow cytometric dot plots for various human cell types present in GFP-NSG murine lungs and spleens after injection of IPF cells 35 days previously.

DESCRIPTION OF THE INVENTION

Figure 1:
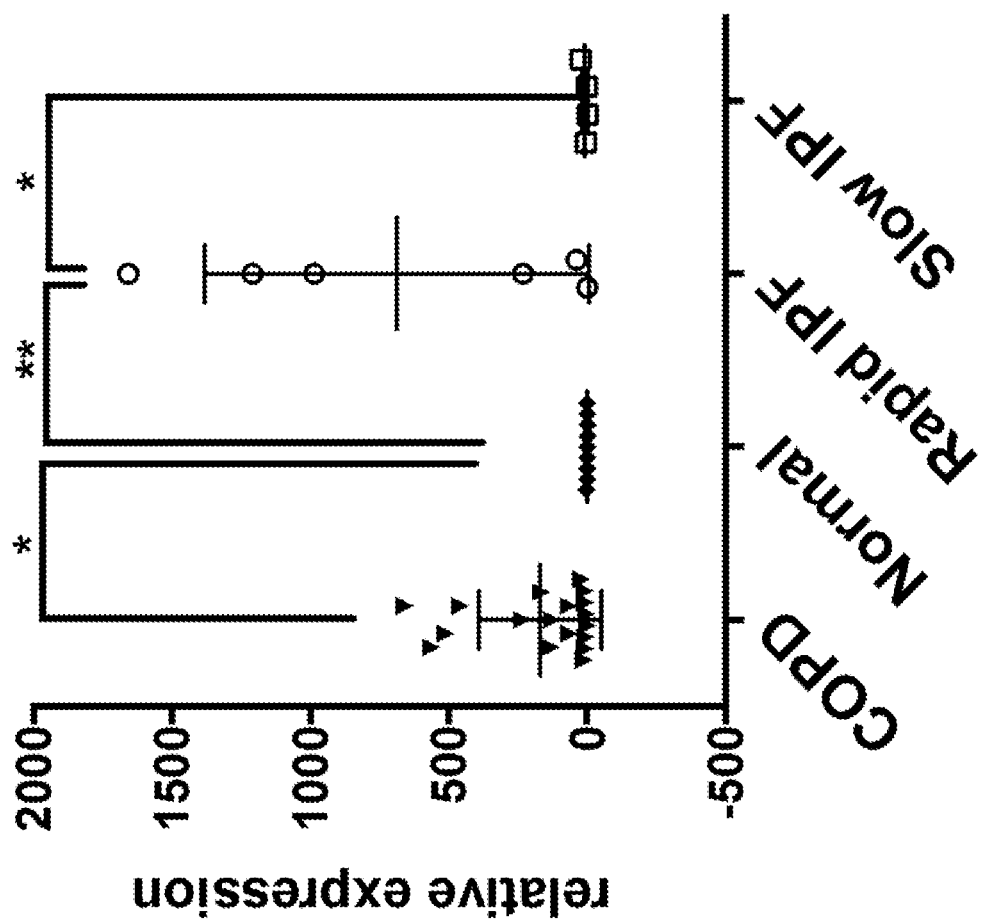
FIG. 1 shows that CCR10 was present in rapid but not slow IPF using quantitative PCR. CCR10 is upregulated in a subset of COPD patients.
Figure 2:
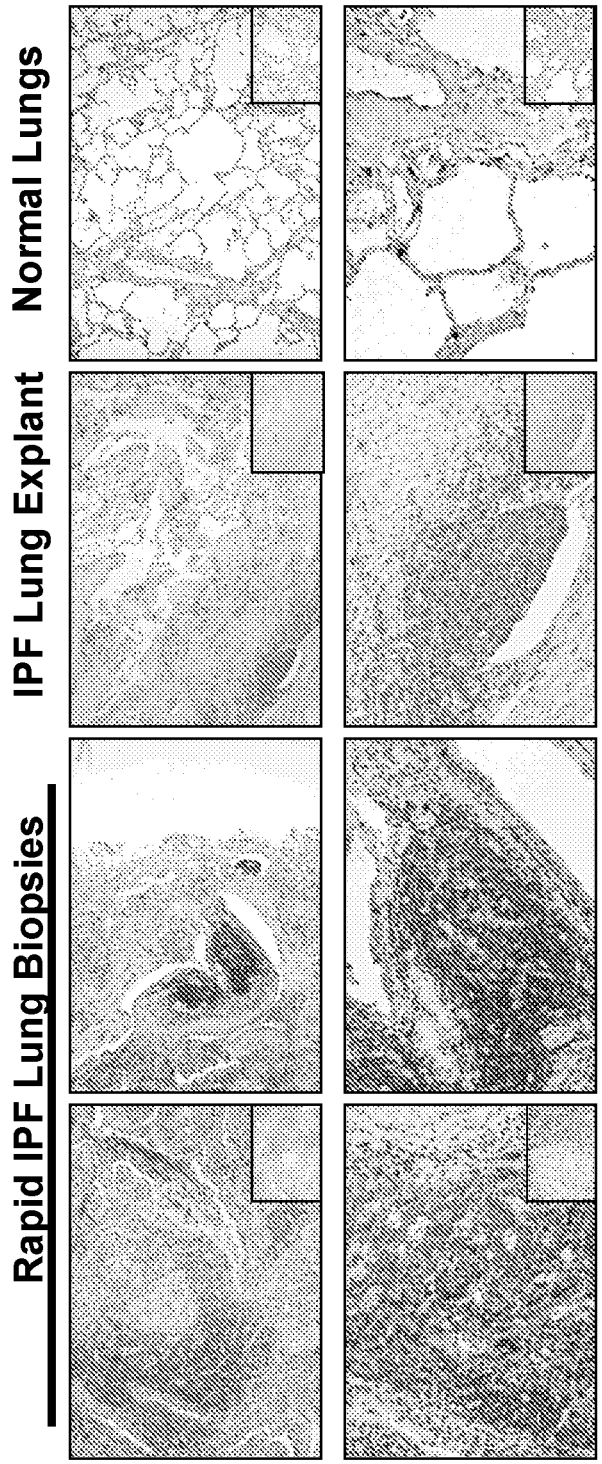
FIG. 2 shows the protein expression profile of CCR10 in lung biopsies in patients who showed rapid progression, as well as the expression of this receptor in an explanted lung sample from an IPF patient who received a lung transplant. This receptor is not abundantly expressed in normal donor lung samples.
Figure 3:
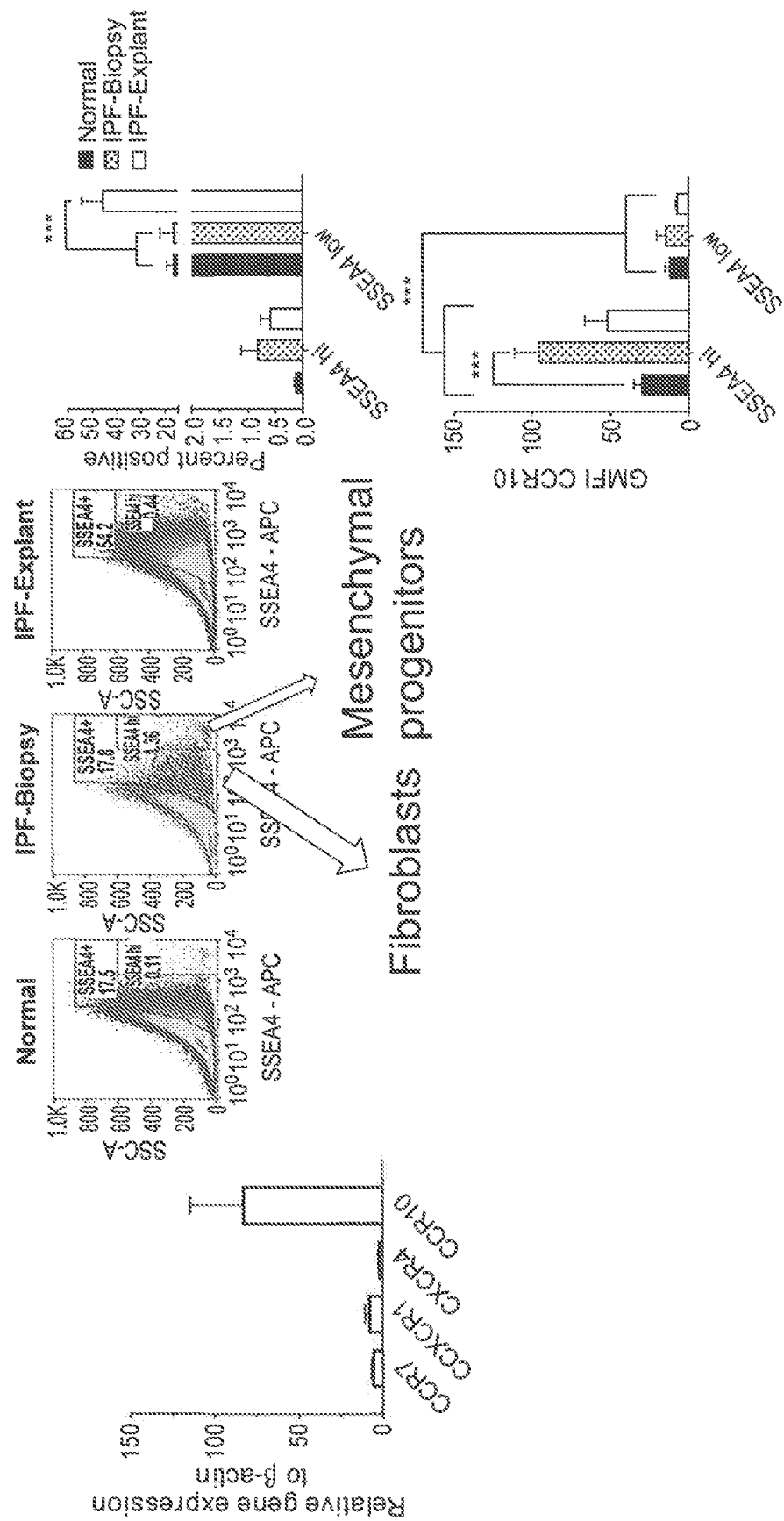
FIG. 3 shows that fibroblasts and fibroblast progenitor cells identified in lung samples were also found to highly express CCR10.
Figure 4:
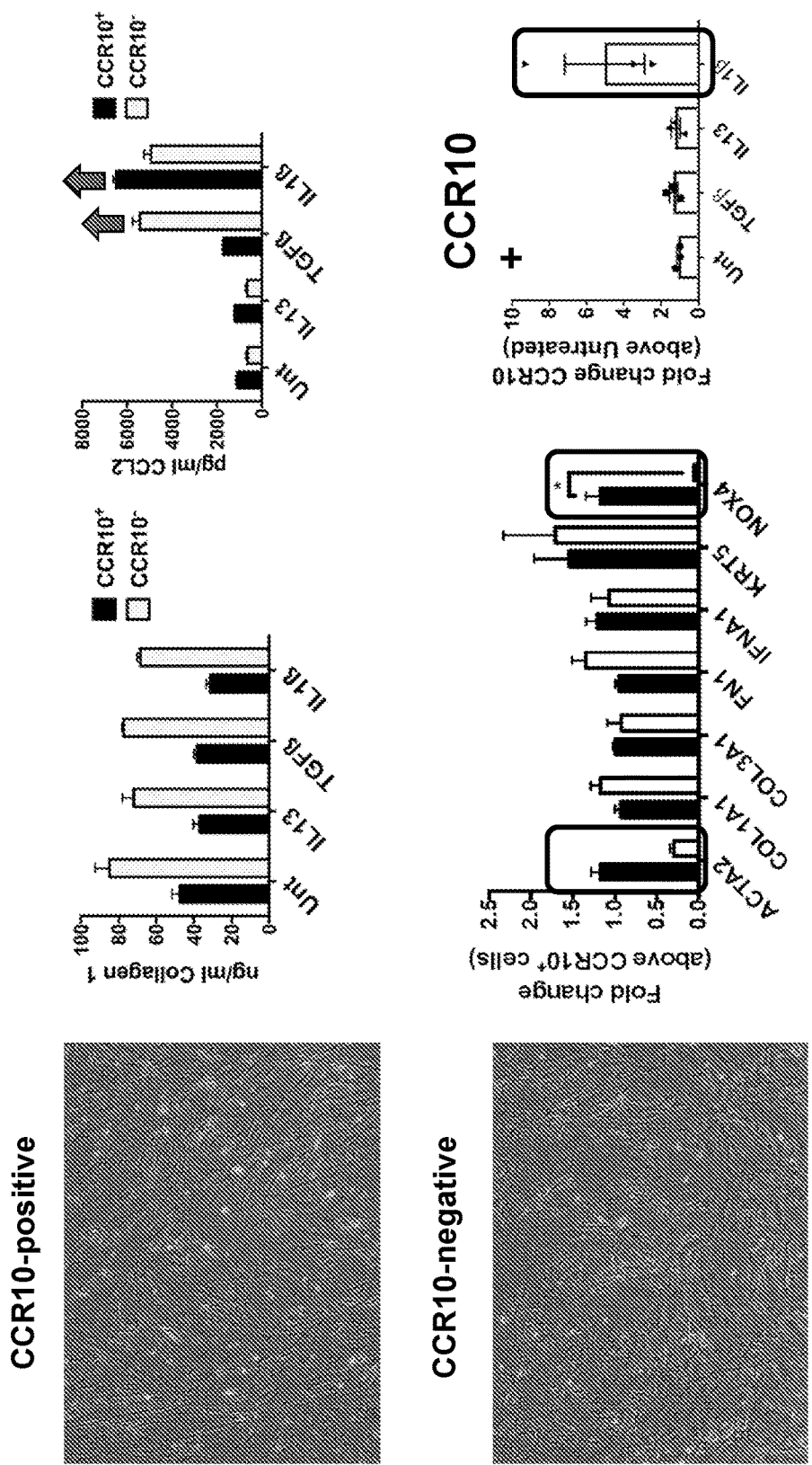
FIG. 4 shows the analysis of CCR10 positive versus CCR10 negative fibroblasts, which revealed key differences between these cells. First, CCR10-positive cells generated less collagen but more interleukin-1 beta (IL-1) compared with their CCR10-negative counterparts. CCR10 positive fibroblasts expressed more alpha smooth muscle actin and NOX4, and were highly responsive to IL-1 compared with CCR10-negative fibroblasts. These data highlight that the expression of CCR10 on fibroblasts appears to alter the function of these cells and likely contributes to the disease pathology we observe in rapid IPF.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., Revised, J. Wiley & Sons (New York, N.Y. 2006); March, *Advanced Organic Chemistry Reactions, Mechanisms and Structure* 7$^{th}$ ed., J. Wiley & Sons (New York, N.Y. 2013); and Sambrook and Russel, *Molecular Cloning: A Laboratory Manual* 4$^{th}$ ed., Cold Spring Harbor Laboratory Press (Cold Spring Harbor, N.Y. 2012), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

Studies in our laboratory have focused on identifying factors that contribute to the progressive lung remodeling in IPF. Transcriptomic analysis in normal, stable- and progressive-IPF lung explants identified a C-C chemokine, CCR10, to be highly enriched in IPF lungs especially in the progressive form of this disease. In vitro studies indicated that CCR10 is highly expressed on Stage Specific Embryonic Antigen 4 (SSEA4) positive fibroblast progenitor cells, whose fibroblast progeny were intrinsically distinct from other fibroblasts as noted by their reduced collagen 1 protein expression, increased alpha smooth muscle actin (αSMA) and NADPH Oxidase 4 (NOX4) transcript expression and responsiveness the cytokine Interleukin 1 (IL1). Immunohistochemical (IHC) analysis supported the transcriptomic analysis, where there were few SSEA4 and CCR10 expressing cells in normal lung explants and an abundance of these cells in progressive IPF lung biopsies and end-stage IPF lung explants. Flow cytometric analysis of normal and IPF lung explants indicated that CCR10 is also expressed on a unique population of cells expressing the lineage markers EpCAM and CD45 that was abundant in IPF and rarely observed in normal lungs. In vivo studies in immunocompromised NSG mice indicated that these cells progressively localized to the lungs, 35 and 63 days after intravenous administration of IPF lung explant cellular suspensions. In vitro expansion of these cells followed by intravenous administration in NSG mice confirmed their profibrotic potential, where cells expanded from IPF lungs consistently induced lung remodeling unlike their normal lung counterparts. Finally, the capacity for these cells to induce disease was confirmed by intravenous administration of these cells into NSG mice followed by their purification from the spleens of the challenged mice and injecting them in another group of mice, where the cells were observed in the lungs and spleens of both the primarily and the secondarily challenged mice and biochemical and histological evidence for pulmonary fibrosis was apparent.

Collectively, these studies suggest that SSEA4+ CCR10+ fibroblast progenitors and EpCAM+ CD45+ CCR10+ cells are more abundant in IPF lungs, where they contribute to the remodeling response and the progression of this disease. Flow cytometric and/or transcriptomic detection of these cells in the blood, lung or bronchoalveolar lavage of these patients can be a useful biomarker to monitor disease progression and therapeutic efficacy. Finally, developing therapeutic strategies to target these cells can be beneficial in slowing or halting the progression of this devastating fibrotic lung disease.

The identity of fibrotic triggers in IPF remain elusive but it is speculated that persistent lung injury might lead to activation of lung fibroblasts. Since nintedanib slows but does not stop progression, efforts have been directed at identifying and characterizing additional mechanisms driving progression in IPF. Described herein, we characterized immune and non-immune cells that express CCR10; this receptor was highest in rapidly progressive IPF patients compared with slow progressing or stable IPF patients and normal lung samples. Intravenous introduction of CCR10$^+$ IPF cells into NSG mice promoted and transferred fibrosis, and nintedanib therapy failed to modulate fibrosis in this model. Most importantly, targeting CCR10$^+$ EphA3$^+$ cells prevented fibrosis in NSG mice. Together, these findings demonstrate that cells from IPF patients expressing CCR10 and EphA3 are profibrotic.

The expression of CCR10, CCL27, and CCL28 were altered in IPF was an unexpected finding given the preponderance of the literature describing these chemokine factors outside the lung. CCR10 or GPR2 is expressed on various normal and neoplastic cell types outside the lung and it binds CCL27 and CCL28. CCL28 was predominantly expressed in normal lung-derived AT2 and in the focal regions in IPF lungs. However, CCL28 transcript levels in peripheral blood mononuclear cells from IPF patients significantly correlated with reduced progression free survival, which is in line with the observed expression of CCR10 (both transcript and protein) in IPF lungs from those patients who experienced rapid progression over the first year after diagnosis compared with IPF patients showing slow or stable disease and normal donors. Together, these findings demonstrate that CCR10 and its ligand, CCL28, are increased in IPF, and their expression appeared to be tied to the progressive nature of this disease.

A humanized mouse model was used to elucidate the role of CCR10$^+$ cells in IPF. In this model, hydroxyproline levels correlated with the abundance of both human CCR10$^+$ immune and non-immune cells, demonstrating that these cells contributed to fibrosis in the lung. The introduction of human IPF CCR10$^+$ cells from a primary NSG group induced lung fibrosis in a secondary group of NSG mice. In these studies, these cells were isolated from the spleens of the primary group of humanized NSG mice due to their relative abundance in this organ. Interestingly, the human cells in the secondary group were predominately Lin$^-$ CCR10$^+$ at the time of analysis in this model. Collectively, CCR10$^+$ cells from IPF patients initiated and transferred fibrotic lung disease after intravenous introduction into NSG mice.

Although nintedanib is a FDA-approved therapeutic in IPF, we observed that this drug did not therapeutically modulate fibrosis in this model. Since the number of human CCR10$^+$ cells were increased in the lungs of nintedanib-treated NSG mice, we speculated that the lack of efficacy of this drug was due to drug resistance in CCR10$^+$ cells. Due to a paucity of validated reagents that target human CCR10, we consequently addressed whether nintedanib resistance in CCR10$^+$ cells was due, in part, to other non-targeted tyrosine kinases. Accordingly, EphA3 was elevated the highest in both IPF lung biopsies and explants. Ephrin receptors represent the largest family of receptor tyrosine kinases, and signaling via these tyrosine kinases has been shown to be essential for various developmental processes in the embryo. The type A Ephrin receptor EphA3 protein is expressed by mesenchymal cells during lung development in mice but it is rarely expressed in normal adult murine lungs. In contrast, EphA3 is frequently over-expressed in various malignancies, and increased EphA3 has been observed in IPF and multi-organ fibrosis. In cultured CCR10$^+$ Lin$^-$ normal and IPF cells, EphA3 was detected intracellularly but the presence of IL1β promoted EphA3 localization to the surface of these cells, Neutralizing Ephrin A ligands using EphA3-FC chimeric protein significantly reduced the synthetic activity of both normal and IPF lung fibroblasts. These findings are consistent with those of Campbell et al., who demonstrated that the EphA3 ligand Ephrin A5 activated mouse fibroblasts. Together, these results point to an profibrotic role for EphA3 and ligands in the lung.

To address the role of CCR10$^+$ EphA3 cells in humanized NSG mice, an EphA3-specific, afucosylated mAb (KB004) was used to target EphA3$^+$ cells through an ADCC-dependent mechanism. Prophylactic treatment with KB004 but not KB243 over 35 days completely prevented the development of lung fibrosis. Targeting EphA3$^+$ cells significantly reduced both CD45$^+$ and Lin$^-$ cells expressing CCR10, thereby confirming the expression of EphA3 on CCR10$^+$ IPF cells. Conversely, the therapeutic treatment with KB004 from days 35 to 63 failed to reduce the numbers of CD45$^+$ and Lin$^-$ CCR10$^+$ cells and pulmonary fibrosis in humanized NSG mice. An explanation for this observation is not presently clear but the failure of human effector immune cells (i.e., CD3$^+$ cells needed to facilitate ADCC) to engraft in NSG mice might be a contributing factor. Indeed, we observed that the numbers of effector CD3$^+$ T cells progressively fall after intravenous introduction into NSG mice.

In summary, we have identified and characterized CCR10$^+$ cells in IPF. CCR10 is expressed in immune and Lin$^-$ cell types, and the introduction of these CCR10$^-$ into NSG mice initiates, maintains, and transfers pulmonary fibrosis. Human CCR10$^+$ cells are resistant to nintedanib treatment and strongly express the receptor tyrosine kinase, EphA3. Finally, the ADCC-dependent targeting of CCR10$^+$ EphA3$^+$ IPF cells prevented fibrosis in humanized NSG mice. Thus, these findings provide further motivation to explore the targeting of CCR10$^+$ EphA3$^+$ cells in IPF.

The invention described herein is based, at least in part, on these findings.

Various embodiments of the invention provide for a method of determining the efficacy of a pulmonary fibrosis treatment, comprising: Obtaining a biological sample from a subject; detecting the number of CCR10-positive cells in the biological sample; comparing the number of CCR10-positive cells in the biological sample to the subject's baseline value or to a reference value; determining that the pulmonary fibrosis treatment is effective in the subject if the number of CCR10-positive cells is the same as the subject's baseline value, is less than the subject's baseline value, or is less than the reference value, or determining that the pulmonary fibrosis treatment is ineffective in the subject if the number of CCR10-positive cells is higher the reference value. In various embodiments, the pulmonary fibrosis is idiopathic pulmonary fibrosis.

In various embodiments, detecting the number of CCR10-positive cells in the biological sample comprises detecting the number of cells that are positive for CCR10, CD45 and EpCAM. That is, to detect the number of triple positive cells. In various instances, the number of triple positive cells will be compared to a subject's baseline value or to a reference value of triple positive cells.

In various embodiments, detecting the number of CCR10-positive cells in the biological sample comprises detecting the number of cells that are positive for at least two markers selected from the group consisting of CCR10, CD45 and EpCAM. That is, to detect the number of double positive cells. In various instances, the number of double positive cells will be compared to a subject's baseline value or to a reference value of double positive cells. For example, if the detection is for CCR10 and CD45, it will be compared to CCR10 positive and CD45 positive cells. If the detection is for CCR10 and EpCAM, it will be compared to CCR10 positive and EpCAM positive cells.

In other embodiments, detecting the number of CCR10-positive cells in the biological sample comprises detecting the number of cells that are positive for CCR10 and CCL28. In various instances, the number cells positive for both CCR10 and CCL28 will be compared to a subject's baseline value or to a reference value of cells positive for both CCR10 and CCL28.

Various embodiments of the invention provide for a method of determining the efficacy of a pulmonary fibrosis treatment and treating pulmonary fibrosis in a subject, comprising: obtaining a biological sample from a subject; detecting the number of CCR10-positive cells in the biological sample; comparing the number of CCR10-positive cells in the biological sample to the subject's baseline value or a reference value; determining that the pulmonary fibrosis treatment is effective in the subject if the number of CCR10-positive cells is the same as the subject's baseline value, is less than the subject's baseline value, or is less than the reference value, and administering the pulmonary fibrosis treatment to the diagnosed subject, or determining that the pulmonary fibrosis treatment is ineffective in the subject if the number of CCR10-positive cells is higher the reference value, and stopping the administration of the pulmonary fibrosis treatment. In various embodiments, the pulmonary fibrosis is idiopathic pulmonary fibrosis.

In various embodiments, detecting the number of CCR10-positive cells in the biological sample comprises detecting the number of cells that are positive for CCR10, CD45 and EpCAM. That is, to detect the number of triple positive cells. In various instances, the number of triple positive cells will be compared to a subject's baseline value or to a reference value of triple positive cells.

In various embodiments, detecting the number of CCR10-positive cells in the biological sample comprises detecting the number of cells that are positive for at least two markers selected from the group consisting of CCR10, CD45 and EpCAM. That is, to detect the number of double positive cells. In various instances, the number of double positive cells will be compared to a subject's baseline value or to a reference value of double positive cells. For example, if the detection is for CCR10 and CD45, it will be compared to CCR10 positive and CD45 positive cells. If the detection is for CCR10 and EpCAM, it will be compared to CCR10 positive and EpCAM positive cells.

In other embodiments, detecting the number of CCR10-positive cells in the biological sample comprises detecting the number of cells that are positive for CCR10 and CCL28. In various instances, the number cells positive for both CCR10 and CCL28 will be compared to a subject's baseline value or to a reference value of cells positive for both CCR10 and CCL28.

Various embodiments of the invention provide for a method of treating pulmonary fibrosis, comprising: requesting or obtaining the results regarding the number of CCR10-positive cells in a biological sample obtained from the subject; determining that a pulmonary fibrosis treatment is effective in the subject if the number of CCR10-positive cells is the same as the subject's baseline value, is less than the subject's baseline value, or is less than the reference value, and administering the pulmonary fibrosis treatment, or determining that the pulmonary fibrosis treatment is ineffective in the subject if the number of CCR10-positive cells is higher the reference value, and stopping the administration of the pulmonary fibrosis treatment. In various embodiments, the pulmonary fibrosis is idiopathic pulmonary fibrosis.

In various embodiments, requesting or obtaining the results regarding the number of CCR10-positive cells in the biological sample comprises requesting or obtaining the results regarding the number of cells that are positive for CCR10, CD45 and EpCAM. That is, the number of triple positive cells. In various instances, the number of triple positive cells will be compared to a subject's baseline value or to a reference value of triple positive cells.

In various embodiments, requesting or obtaining the results regarding the number of CCR10-positive cells in the biological sample comprises requesting or obtaining the results regarding the number of cells that are positive for at least two markers selected from the group consisting of CCR10, CD45 and EpCAM. That is, the number of double positive cells. In various instances, the number of double positive cells will be compared to a subject's baseline value or to a reference value of double positive cells. For example, if the detection is for CCR10 and CD45, it will be compared to CCR10 positive and CD45 positive cells. If the detection is for CCR10 and EpCAM, it will be compared to CCR10 positive and EpCAM positive cells.

In other embodiments, requesting or Obtaining the results regarding the number of CCR10-positive cells in the biological sample comprises requesting or obtaining the results regarding the number of cells that are positive for CCR10 and CCL28. In various instances, the number cells positive for both CCR10 and CCL28 will be compared to a subject's baseline value or to a reference value of cells positive for both CCR10 and CCL28.

Various embodiments of the present invention provide for a method of treating pulmonary fibrosis in a subject, comprising: requesting or obtaining the results regarding whether a pulmonary fibrosis treatment is effective in the subject, wherein the results are obtained by a method comprising: obtaining a biological sample from a subject; detecting the number of CCR10-positive cells in the biological sample; comparing the number of CCR10-positive cells in the biological sample to a reference value; determining that the pulmonary fibrosis treatment is effective in the subject if the number of CCR10-positive cells is the same as the subject's baseline value, is less than the subject's baseline value, or is less than the reference value, or determining that the pulmonary fibrosis treatment is ineffective in the subject if the number of CCR10-positive cells is higher the reference value; and administering the pulmonary fibrosis treatment to the subject if the pulmonary fibrosis treatment is effective, or stopping the administration of the pulmonary fibrosis treatment to the subject if the pulmonary fibrosis treatment is ineffective.

In various embodiments, requesting or obtaining the results regarding the number of CCR10-positive cells in the biological sample comprises requesting or obtaining the results regarding the number of cells that are positive for CCR10, CD45 and EpCAM. That is, the number of triple positive cells. In various instances, the number of triple positive cells will be compared to a subject's baseline value or to a reference value of triple positive cells.

In various embodiments, requesting or obtaining the results regarding the number of CCR10-positive cells in the biological sample comprises requesting or obtaining the results regarding the number of cells that are positive for at least two markers selected from the group consisting of CCR10, CD45 and EpCAM. That is, to detect the number of double positive cells. In various instances, the number of double positive cells will be compared to a subject's baseline value or to a reference value of double positive cells. For example, if the detection is for CCR10 and CD45, it will be compared to CCR10 positive and CD45 positive cells. If the detection is for CCR10 and EpCAM, it will be compared to CCR10 positive and EpCAM positive cells.

In other embodiments, requesting or obtaining the results regarding the number of CCR10-positive cells in the biological sample comprises requesting or obtaining the results regarding the number of cells that are positive CCM10 and CCL28. In various instances, the number cells positive for both CCR10 and CCL28 will be compared to a subject's baseline value or to a reference value of cells positive for both CCR10 and CCL28.

Various embodiments of the present invention provide for a method of treating pulmonary fibrosis, comprising: administering a pulmonary fibrosis treatment to a subject who has been diagnosed that the pulmonary fibrosis treatment is effective by a method comprising: obtaining a biological sample from a subject; detecting the number of CCR10-positive cells in the biological sample; comparing the number of CCR10-positive cells in the biological sample to a reference value; determining that the pulmonary fibrosis treatment is effective in the subject if the number of CCR10-positive cells is the same as the subject's baseline value, is less than the subject's baseline value, or is less than the reference value, or determining that the pulmonary fibrosis treatment is ineffective in the subject if the number of CCR10-positive cells is higher the reference value. In various embodiments, the pulmonary fibrosis is idiopathic pulmonary fibrosis.

In various embodiments, detecting the number of CCR10-positive cells in the biological sample comprises detecting the number of cells that are positive for CCR10, CD45 and EpCAM. That is, to detect the number of triple positive cells. In various instances, the number of triple positive cells will be compared to a subject's baseline value or to a reference value of triple positive cells.

In various embodiments, requesting or obtaining the results regarding the number of CCR10-positive cells in the biological sample comprises requesting or obtaining the results regarding the number of cells that are positive for at least two markers selected from the group consisting of CCR10, CD45 and EpCAM. That is, to detect the number of double positive cells. In various instances, the number of double positive cells will be compared to a subject's baseline value or to a reference value of double positive cells. For example, if the detection is for CCR10 and CD45, it will be compared to CCR10 positive and CD45 positive cells. If the detection is for CCR10 and EpCAM, it will be compared to CCR10 positive and EpCAM positive cells.

In other embodiments, detecting the number of CCR10-positive cells in the biological sample comprises detecting the number of cells that are positive for CCR10 and CCL28. In various instances, the number cells positive for both CCR10 and CCL28 will be compared to a subject's baseline value or to a reference value of cells positive for both CCR10 and CCL28.

Various embodiments of the present invention provide for a method of predicting progression of pulmonary fibrosis, comprising: obtaining a biological sample from a subject; detecting the number of CCR10-positive cells in the biological sample; comparing the number of CCR10-positive cells in the biological sample to a reference value; and predicting a faster progression of pulmonary fibrosis if the number of CCR10-positive cells are higher than the reference value, or predicting a slower progression of pulmonary fibrosis if the number of CCR10-positive cells are lower than the reference value. In various embodiments, the pulmonary fibrosis is idiopathic pulmonary fibrosis.

In various embodiments, detecting the number of CCR10-positive cells in the biological sample comprises detecting the number of cells that are positive for CCR10, CD45 and EpCAM. That is, to detect the number of triple positive cells. In various instances, the number of triple positive cells will be compared to a subject's baseline value or to a reference value of triple positive cells.

In various embodiments, detecting the number of CCR10-positive cells in the biological sample comprises detecting the number of cells that are positive for at least two markers selected from the group consisting of CCR10, CD45 and EpCAM. That is, to detect the number of double positive cells. In various instances, the number of double positive cells will be compared to a subject's baseline value or to a reference value of double positive cells. For example, if the detection is for CCR10 and CD45, it will be compared to CCR10 positive and CD45 positive cells. If the detection is for CCR10 and EpCAM, it will be compared to CCR10 positive and EpCAM positive cells.

In other embodiments, detecting the number of CCR10-positive cells in the biological sample comprises detecting the number of cells that are positive for CCR10 and CCL28. In various instances, the number cells positive for both CCR10 and CCL28 will be compared to a subject's baseline value or to a reference value of cells positive for both CCR10 and CCL28.

Various embodiments of the present invention provide for a method of selecting a pulmonary fibrosis treatment, comprising: obtaining a biological sample from a subject; detecting the number of CCR10-positive cells in the biological sample; comparing the number of CCR10-positive cells in the biological sample to a reference value; predicting a faster progression of pulmonary fibrosis if the number of CCR10-positive cells higher than the reference value; and selecting an experimental treatment if the subject is predicted to have a faster progression of pulmonary fibrosis, or selecting a standard pulmonary fibrosis treatment if the subject is predicted to not have a faster progression of pulmonary fibrosis. In various embodiments, the pulmonary fibrosis is idiopathic pulmonary fibrosis.

In various embodiments, detecting the number of CCR10-positive cells in the biological sample comprises detecting the number of cells that are positive for CCR10, CD45 and EpCAM. That is, to detect the number of triple positive cells. In various instances, the number of triple positive cells will be compared to a subject's baseline value or to a reference value of triple positive cells.

In various embodiments, detecting the number of CCR10-positive cells in the biological sample comprises detecting the number of cells that are positive for at least two markers selected from the group consisting of CCR10, CD45 and EpCAM. That is, to detect the number of double positive cells. In various instances, the number of double positive cells will be compared to a subject's baseline value or to a reference value of double positive cells. For example, if the detection is for CCR10 and CD45, it will be compared to CCR10 positive and CD45 positive cells. If the detection is for CCR10 and EpCAM, it will be compared to CCR10 positive and EpCAM positive cells.

In other embodiments, detecting the number of CCR10-positive cells in the biological sample comprises detecting the number of cells that are positive for CCR10 and CCL28. In various instances, the number cells positive for both CCR10 and CCL28 will be compared to a subject's baseline value or to a reference value of cells positive for both CCR10 and CCL28.

Various embodiments of the present invention provide for a method of detecting a change in the number of CCR10+ cells in a subject having or suspected of having pulmonary fibrosis, comprising: detecting the number of CCR10-positive cells in a biological sample from the subject; comparing the number of CCR10-positive cells in the biological sample to the subject's baseline value or to a reference value; and determining an increase or decrease in the number of CCR10-positive cells in the biological sample. In various embodiments, the pulmonary fibrosis is idiopathic pulmonary fibrosis.

In various embodiments, detecting the number of CCR10-positive cells in the biological sample comprises detecting the number of cells that are positive for CCR10, CD45 and EpCAM. That is, to detect the number of triple positive cells. In various instances, the number of triple positive cells will be compared to a subject's baseline value or to a reference value of triple positive cells.

In other embodiments, detecting the number of CCR10-positive cells in the biological sample comprises detecting the number of cells that are positive for CCR10 and CCL28. In various instances, the number cells positive for both CCR10 and CCL28 will be compared to a subject's baseline value or to a reference value of cells positive for both CCR10 and CCL28.

In various embodiments, the method comprises first obtaining the biological sample from the subject having or suspected of having pulmonary fibrosis.

Various embodiments provide for a method of detecting resistance to nintedanib in a subject having pulmonary fibrosis, comprising: detecting the number of CCR10-positive cells in a biological sample obtained from the subject; comparing the number of CCR10-positive cells in the biological sample to the subject's baseline value or to a reference value; determining an increase or decrease in the number of CCR10-positive cells in the biological sample; and determining resistance to nintedanib if there is an increase in the number of CCR10-positive cells in the biological sample. In various embodiments, the pulmonary fibrosis is idiopathic pulmonary fibrosis.

In various embodiments, detecting the number of CCR10-positive cells in the biological sample comprises detecting the number of cells that are positive for CCR10, CD45 and EpCAM. That is, to detect the number of triple positive cells, in various instances, the number of triple positive cells will be compared to a subject's baseline value or to a reference value of triple positive cells.

In other embodiments, detecting the number of CCR10-positive cells in the biological sample comprises detecting the number of cells that are positive for CCR10 and CCL28. In various instances, the number cells positive for both CCR10 and CCL28 will be compared to a reference value of cells positive for both CCR10 and. CCL28.

In various embodiments the method comprises first obtaining the biological sample from the subject having or suspected of having pulmonary fibrosis.

In various embodiments, the if resistance to nintedanib is determined to be present, the subject will not be administered nintedanib or administration of nintedanib will cease.

Reference Values

When monitoring the efficacy of a pulmonary fibrosis treatment, the number of CCR10-positive cells in a pre-established sample size from the subject can be measured as used as the baseline value for comparison to the number of CCR10-positive cells (or CCR10+/CD45+/EpCAM+ cells, or CCR10+/CD45+ cells, or CCR10+/EpCAM+ cells, or CD45+/EpCAM+ cells, or CCR10+/CCL28+ cells) that the subject in the same sample size has during treatment. Thus, when the number of CCR10-positive cells (or CCR10+/CD45+/EpCAM+ cells, or CCR10+/CD45+ cells, or CCR10+/EpCAM+ cells, or CD45+/EpCAM+ cells, or CCR10+/CCL28+ cells) decrease, it is indicative the effective treatment. Alternatively, when the number of CCR10-positive cells (or CCR10+/CD45+/EpCAM+ cells, or CCR10+/CD45+ cells, or CCR10+/EpCAM+ cells, or CD45+/EpCAM+ cells, or CCR10+/CCL28+ cells) remains the same, it can be indicative of effective treatment, that is, the treatment has halted or inhibited the progression of pulmonary fibrosis.

When monitoring the efficacy of a pulmonary fibrosis treatment, there are instances wherein the number of CCR10-positive cells (or CCR10+/CD45+/EpCAM+ cells, or CCR10+/CD45+ cells, or CCR10-EpCAM+ cells, or CD45+/EpCAM+ cells, or CCR10+/CCL28+ cells) can increase compared to the subject's baseline level, but still indicate that the pulmonary fibrosis treatment is effective. For example, while the number of CCR10-postitive cells (or CCR10+/CD45+/EpCAM+ cells, or CCR10+/CD45+ cells, or CCR10+/EpCAM+ cells, or CD45+/EpCAM+ cells, or CCR10+/CCL28+ cells) increased, the increase of the number of cells may have been slowed by the pulmonary fibrosis treatment. Thus, compared to similar subjects who have pulmonary fibrosis that did not undergo the pulmonary fibrosis treatment, the number of CCR10-positive cells (or CCR10+/CD45+/EpCAM+ cells, or CCR10+/CD45+ cells, or CCR10+/EpCAM+ cells, or CD45+/EpCAM+ cells, or CCR10+/CCL28+ cells) is lower than the number of CCR10-positive cells in those similar subjects. Thus, a reference value can be calculated from those similar subjects to provide the comparison value. One of ordinary skill in the art will readily appreciate how to calculate this reference value. For example, the average number of CCR10-positive cells (or CCR10+/CD45+/EpCAM+ cells, or CCR10+/CD45+ cells, or CCR10+/EpCAM+ cells, or CD45+/EpCAM+ cells, or CCR10+/CCL28+ cells) from 2, 3, 4, 5, 6, 7, 8, 9, 10, 11, 12, 13, 14, or 15 subjects can be taken as used as the reference value. Additional number of subjects, such as, but not limited to 15-20, 20-25, 30-40, 50-60, 70-80, 90-100, 100-125, 125-150, 150-175, 175-200, or 200-300 can be used to calculate this reference value.

When predicting progression of pulmonary fibrosis, the reference value can be calculated from subjects who have pulmonary fibrosis at a certain stage of the disease. For example, a reference value can be calculated from pulmonary fibrosis subjects that did not have a rapid progression of the disease.

In other embodiments, the presence of CCR10-positive cells in a sample taken at the time of diagnosis, for example, in a transbronchial biopsy (TBBX), predicts a rapid progression of pulmonary fibrosis. Thus, the reference value can be zero, or can be the number of CCR10-positive cells from a healthy subject, or calculated from a population of healthy subjects.

Selecting Therapies

Various embodiments of the present invention provide for selecting a pulmonary fibrosis therapy. Selecting a therapy as used herein, includes but is not limited to selecting, choosing, prescribing, advising, recommending, instructing, or counseling the subject with respect to the treatment.

If the subject is predicted to not have a rapid progression of pulmonary fibrosis, a standard therapy can be selected for the subject. Examples of standard therapies include but are not limited to, OFEV (Nintedanib) and ESBRIET (Pirfenidone).

If the subject is predicted to have a rapid progression of pulmonary fibrosis, the subject likely has a poor prognosis and survival time may be limited, for example to 1-2 years. In these instances, aggressive and/or experimental therapy can be selected for the subject. One such therapy at the time of the present invention is KB004 (KaloBios), which targets EphA3. Other experimental therapies, such as those that are part of clinical trials can be selected for the subject. Examples of these therapies include but are not limited to tipelukast (MN-001 MediciNova), IW001 (ImmuneWorks), sildenafil citrate; combined plasma exchange (PEX), rituximab, and conventional corticosteroid; Dasatinib+Quercetin; QAX576 (Novartis) Pamrevlumab (anti-CTGF) Fibrogen; CC90001 (JNK) Celgene; GLPG1690 (autotaxin) Galapagos; Duplimab (anti-IL-4/IL-13) Regeneron/Sanofi; Erivedge (sonic hedgehog inhibitor) Roche; Anti-IL-13 (Roche), Additional IPF therapies can be found on clinicaltrials.gov.

Systems and Compositions

Various embodiments provide for a system or composition comprising a biological sample obtained from a subject suspected of having or having pulmonary fibrosis; and an assay to detect the number of CCR10-positive cells. In other embodiments, the system or composition comprises a biological sample obtained from a subject suspected of having or having pulmonary fibrosis and an assay selected from the group consisting of an assay to detect CCR10+/CD45+/EpCAM+ cells, an assay to detect or CCR10+/CD45+ cells, an assay to detect CCR10+/EpCAM+ cells, an assay to detect CD45+/EpCAM+ cells, an assay to detect CCR10+/CCL28+ cells), and combinations thereof.

Biological Samples

Examples of biological samples include but are not limited to body fluids, whole blood, plasma, serum, lung aspirate, lung sputum, lung draining lymph node biopsies, pulmonary secretions, transbronchial biopsies, bronchial brushings, bronchoalveolar lavage fluid, surgical lung biopsies, and saliva. Additional examples include intestinal fluids or aspirate, and stomach fluids or aspirate, cerebral spinal fluid (CSF), urine, sweat, saliva, tears, breast aspirate, prostate fluid, seminal fluid, cervical scraping, amniotic fluid, intraocular fluid, mucous, and moisture in breath. Further examples include tissue samples, such as lung tissue sample. In particular embodiments of the method, the biological sample may be whole blood, blood plasma, blood serum, lung fluid or aspirate. In various embodiments, the biological sample may be whole blood. In various embodiments, the biological sample may be serum. In various embodiments, the biological sample may be plasma. In various embodiments, the biological sample is peripheral blood mononuclear cells. In various embodiments, the biological sample is bronchoalveolar lavage fluid. In various embodiments, the biological sample is lung cells or lung tissue.

Assays

Detecting the number of CCR10-positive cells in the biological sample can be done via assays such as, but are not limited to, flow cytometry, enzyme-linked immunosorbent assay (ELISA), including but not limited to indirect ELISA, sandwich ELISA, competitive ELISA, multiple and portable ELISA, immunohistochemistry, fluorescence in situ hybridization (FISH), radioimmuno assays, and affinity purification, transcript analysis, qPCR, RNA sequencing, affymetrix array.

Kits

The present invention is also directed to a kit to for monitoring the efficacy of a pulmonary fibrosis treatment, for selecting a pulmonary fibrosis treatment and for determining the progression of pulmonary fibrosis. The kit is useful for practicing these inventive methods. The kit is an assemblage of materials or components.

The exact nature of the components configured in the inventive kit depends on its intended purpose. For example, some embodiments are configured for the purpose of monitoring the efficacy of a pulmonary fibrosis treatment, some for the purposes of selecting a pulmonary fibrosis treatment, and some for the purpose of determining the progression of pulmonary fibrosis. In one embodiment, the kit is configured particularly for mammalian subjects. In another embodiment, the kit is configured particularly for human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to monitoring the efficacy of a pulmonary fibrosis treatment, to select a pulmonary fibrosis treatment and to determine the progression of pulmonary fibrosis. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example, the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. The packaging materials employed in the kit are those customarily utilized in pulmonary treatments. As used herein, the term "package" refers to a suitable solid matrix or material such as glass, plastic, paper, foil, and the like, capable of holding the individual kit components. The packaging material generally has an external label which indicates the contents and/or purpose of the kit and/or its components.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

We have generated to date regarding the expression of CCR10 on a unique cell population, which we have found to be the primary initiator of pulmonary fibrosis in our humanized model systems.

CCR10 was first identified using an Affymetrix platform to explore the genomic differences between rapid and slow progression in group of IPF patients. CCR10 was identified as a key cell surface expressed protein that distinguished these two groups of patients. We confirmed that CCR10 was present in rapid but not slow IPF using quantitative PCR. Also of note was our finding that CCR10 is upregulated in a subset of COPD patients.

The figures herein highlight the protein expression profile of CCR10 in lung biopsies in patients who showed rapid progression, as well as the expression of this receptor in an explanted lung sample from an IPF patient who received a lung transplant. Note that this receptor is not abundantly expressed in normal donor lung samples.

Fibroblasts and fibroblast progenitor cells identified in lung samples were also found to highly express CCR10.

Analysis of CCR10 positive versus CCR10 negative fibroblasts revealed key differences between these cells. First, CCR10-positive cells generated less collagen but more interleukin-1 beta (IL-1) compared with their CCR10-negative counterparts. Also of note, CCR10-positive fibroblasts expressed more alpha smooth muscle actin and NOX4, and were highly responsive to IL-1 compared with CCR10-negative fibroblasts. These data highlight that the expression of CCR10 on fibroblasts appears to alter the function of these cells and likely contributes to the disease pathology we observe in rapid IPF.

Further analysis of CCR10 expression in IPF and normal lung samples revealed the presence of another cell, which did not have the elongated appearance of a fibroblast but this other cell was highly positive for CCR10. Without wishing to be bound by any particular theory, we believe that this cell was an immune cell but in analyzing these tissues for immune cells like plasmacytoid DCs, we noted that CCR10 expression was much lower on these cells compared with the strongly positive cells clearly observed in IPF-1.

Flow cytometry was used on various cell populations dissociated from normal and IPF biopsies and it was then observed that the CCR10 expression was uniquely localized to a population of cells in IPF, which expressed CD45, EpCAM, and CCR10. Note this population is not present in normal lung but is abundantly expressed in IPF. The percentages of the various CD45 and EpCAM double positive cells are shown in the figures, and these data clearly highlight the presence of a EpCAM, CD45, CCR10 population in IPF compared with normal lung samples.

Immunohistochemistry was used to confirm the presence of CD45 and EpCAM expressing cells in IPF lung samples. Double positive cells were observed and these cells were uniquely positioned next to fibroblastic foci (black circle) and in the areas of the lung that are undergoing 'honeycombing' or abnormal remodeling.

To further confirm the relevance of this CD45, EpCAM, and CCR10 expressing cell (or triple positive cell) to IPF, we have completed three separate studies in which we have explored the significance of this cell in a humanized mouse model of IPF. The details of this model and the variations we have tested in this model are shown in the figures We found that the infusion of human IPF cells causes lung fibrosis, which is apparent in histological sections and following biochemical analysis of other lung tissue for the presence of hydroxyproline.

Also of note, the CCR10 cells localize to the spleens of SCID mice following the infusion of IPF cells.

We demonstrated that the triple positive cells are present in the cells infused into SCID mice, these cells are not present in naive SCID mice, and once infused the human triple positive cells localize in the spleen before moving to the lungs of injected SCID mice. The presence of human CCR10 in the lungs of SCID mice receiving human cells 63 days later is also shown.

In order to study the triple-positive cells in more detail, we utilized a cell culture technique to expand these cells. As shown in the figures, this technique was very effective in expanding the triple positive population using both normal and IPF cells. With these expanded cells, we were able to use RNA sequencing to better characterize and contrast normal and IPF triple positive cells. The IPF cells express much higher levels of fibrosis transcripts while the normal cells have a much stronger epithelial transcript signature.

Infusion of IPF but not normal CD45, EpCAM, and CCR10 cells into SCID mice induced pulmonary fibrosis as shown histologically and via the hydroxyproline assay.

The third SCID provides yet further proof that the triple positive cell is both pro-fibrotic and disease transferring. In this 3rd study, we introduced IPF explant cells and 63 days later isolated the CCR10-expressing cells from the spleens of these mice. These human cells from mouse spleen were then introduced into a second group of SCID mice and 63 days later these mice were examined for the presence of pulmonary fibrosis. There was both biochemical and histological evidence of pulmonary fibrosis in the secondary model, and the predominant cell type was the human CCR10-expressing cell both in spleen and lung from this secondary group.

The key findings from our studies around the expression and function of CCR10 in IPF includes (1) CCR10 expression is markedly elevated in rapid IPF; (2) Several cell types express CCR10 including mesenchymal cells, immune cells, epithelial cells, and 'others', and (3) CCR10-expressing cells are both pro-fibrotic and disease-transferring cells in a NSG SCID model of IPF.

Example 2

Flow cytometric analysis of lung explant cellular suspensions demonstrated an abundance of EphA3 expressing cells in IPF relative to normal lungs. IHC analysis indicated the presence of these cells near honeycombing cysts, in the interstitium and their expansion in IPF lung biopsies and explants relative to normal lungs. Cell sorting, in vitro expansion, RNAseq analysis and flow cytometric validation indicated that these cells expressed markers commonly observed in Mucosal Invariant T (MAIT) cells. Further, pulmonary injury and remodeling was observed in NOD/SCID mice 63 days after intravenous administration of IPF but not normal in vitro expanded MAIT cells. Finally, targeting EphA3 expressing cells using an ADCC inducing afucosylated anti-EphA3 antibody ameliorated the fibrotic response in IPF explant cell challenged NOD/SCID mice.

EphA3 expression was detected in IPF but not normal MAIT cells. These cells home to the lungs of NOD/SCID mice when intravenously administered, where they induce injury and remodeling. Finally, targeting these cells using an ADCC inducing afucosylated anti-EphA3 antibody ameliorated lung remodeling in IPF explant cell challenged NOD/SCID mice.

Example 3

To identify unique cellular population(s) contributing to the fibrotic progression in IPF, cells in fibrotic lung tissues were compared to their normal lung counterparts. The use of all patient tissues and animals for these studies was approved by the University of Michigan's and Cedar-Sinai Medical Center's Institutional Review Boards and Cedar-Sinai Medical Center's Comparative medicine. Lung explants were mechanically dissociated to generate cellular suspensions. Red blood cells were lysed using a hypotonic buffer and the remaining cells were utilized for further analysis. For v/ire expansion of CD45+ EPCAM+ CCR10+ cells, lung explant cells were cultured in 50% senescent IPF fibroblast conditioned medium and 50% complete medium (DMEM containing 15% FBS, L-Glutamine and antibiotics) in the presence of 10 µM Y-27632 (Stern Cell Technologies). Medium was replenished every 2-3 days until colonies were apparent. Cells were passaged 2-3 times prior to utilization. Normal and IPF lung fibroblasts were generated by mechanically dissociating lung tissue on cell culture dishes and culturing the dissociated tissue in complete medium. Fresh medium was added every 2-3 days until fibroblast colonies were observed. Fibroblasts were passaged 5-6 times prior to utilization. Murine lung suspensions were generated by enzymatic dissociation using a tissue dissociation kit (Miltenyi Biotech) as recommended by the manufacturer.

For transcriptomic analysis, RNA was isolated from tissues or cells using Trizol™ reagent, complementary DNA (cDNA) was generated using M-HTLV reverse transcriptase and oligo dT primers (ThermoFisher Scientific) and quantitative PCR (qPCR) analysis was performed using predesigned primers and probes and a 2× TaqMan master mix (ThermoFisher Scientific) as recommended by the manufacturer. All qPCR analysis was performed using a 7500 or a Viia7 Real-Time PCR systems (ThermoFisher Scientific).

Flow cytometric analysis of lung fibroblasts and explant cells was performed using antibodies to SSEA4 and human CD45, EpCAM, and CCR10 proteins. Nonspecific binding was blocked by incubating cells with anti-human Fc antibodies (Fc block, Biolegend) in staining buffer (DPBS+2% FBS) for 15 minutes on ice. Cells were then incubated with the fluorophore conjugated antibodies diluted 1:200 or as recommended by the manufacturer for an additional 15 minutes at 4° C. in the dark. As a control for non-specific binding of the antibodies, fluorophore conjugated isotype control antibodies were added to an aliquot of the cells at a similar concentration and incubated for 15 minutes at 4° C. in the dark. After 15 minutes, cells were washed twice with flow cytometry staining buffer and fixed using 5% neutral buffered formalin (NEW). Flow cytometric data was acquired using a MacsQuant 10 flow analyzer within one week of staining and fixation. All the data was analyzed using Flowjo version 10.1 (FlowJo, LLC).

For histological analysis paraffin sections were deparaffinized in xylene and hydrated. Antigen retrieval was performed using Citrate buffer pH 6 at 80° C. for 12-15 hours. Tissues were then washed, permeabilized and then blocked using 2% Normal Goat Serum. Tissues were then incubated with the primary antibodies overnight at 4° C. as follows: CCR10 (Abcam ab30718; 1 µg/ml), SSEA4 (Abcam ab16287; 1:100), biotin-anti-CD1a (Biolegend 300112; 5 µg/ml), CD45 (Abcam ab10558, 5 µg/ml) and EpCAM (Cell Signaling 2929S, 1:200). After incubation, tissues were washed, incubated with an HRP, AP or fluorophore conjugated secondary for 30-45 minutes at room temperature. Fluorescent samples were mounted using a DAPI containing mounting medium. Histological samples where developed, counter stained in hematoxylin. All images were acquired using a Zeiss fluorescence microscope.

Example 4

Cells and Cell Culture Conditions:

IPF surgical lung biopsy samples were obtained. IPF lung fibroblasts were generated by mechanically dissociating IPF lung biopsies or explants into sterile tissue culture plates. After mechanical dissociation, tissues were passed through a 25-ml pipette for 10 times, in DMEM (Lonza)+15% FBS (Cell Generation), 100 IU penicillin and 100 µg/ml streptomycin (Mediatech), 292 µg/ml L-Glutamine (Mediatech) and 100 µg/ml of Primocin (Invivogen) (complete medium). Cells were cultured at 37° C. and 10% $CO_2$, medium was changed twice a week by careful removal of the liquid and retaining the minced tissues. This process was repeated for 1-2 weeks, until stromal colonies were apparent, after which fibroblast colonies were trypsinized and passaged. After 4-5 passages, fibroblast purity was confirmed using flow cytometry and/or qPCR analysis for CD45, EpCAM and CD31. Fibroblasts were then cultured in complete medium; fresh medium was added to the fibroblasts every 2-3 days and the cells were passaged when they were 70-90% confluent. For stimulation experiments, $2.5 \times 10^5$ cells/well were plated onto a 6 well plate. Cells were incubated overnight and then washed and stimulated with 20 ng/ml TGFβ, 10 ng/ml IL-13, 20 ng/ml IL-4, 20 ng/ml IL-6, 20 ng/ml IL-1β, 20 ng/ml VEGF, 20 ng/ml DLL4, 20 ng/ml. SCF and 20 ng/ml OSM (R&D systems) for 24 h. After treatment, cells were then analyzed by flow cytometry for cell surface EphA3 expression.

Soluble Collagen 1 and in Cell αSMA ELISA Analysis:

Lung fibroblasts (5000/well) were plated into a 96 well plate and incubated overnight. After incubation, cells were stimulated with 20 ng/ml of IL1β or vehicle in the presence or absence of 20 µg/ml of EphA3-Fc or IgG antibodies (supplied by Kalobios) for 24 and 72 h. After stimulation, conditioned supernatants were collected and the cells were washed and fixed with 4% paraformaldehyde solution in PBS for 10 min at room temperature.

In Cell αSMA ELISA:

After fixation, cells were washed and permeabilized with 0.5% Triton X-100 in DPBS for 10 min, washed and endogenous peroxidase activity was blocked by adding a solution of 0.3% $H_2O_2$ in DPBS to the cells and incubating the cells with the solution for 20 min at room temperature. Cells were then washed and wells were blocked with a 1% BSA solution in DPBS for 30 min at room temperature. After blocking, cells were incubated with 500 ng/ml of anti-czSMA antibodies (Clone 1A4, Abcam) overnight at 4° C. on a rocker. After incubation, cells were washed and incubated with an HRP conjugated rabbit anti-mouse antibody (1:5000 diluted, R&D systems) for 30 min at room temperature. Cells where then washed and the reaction was developed using 100 µl of TMB developing reagent (Fitzgerald Industries International) until sufficient color was observed. The reaction was then stopped by adding 50 µl of 2N sulfuric acid and data were acquired by reading the absorbance at 405 nm using a Synergy H1 microplate reader (BioTek Instruments Inc.). To normalize to cell number, the plate was then washed and cells were incubated with 500 ng/ml of anti-β-tubulin antibodies (Abcam) and incubated overnight at 4° C. Cells were then washed, incubated with 200 ng/ml of AP-conjugated goat anti-rabbit IgG antibody (SeraCare Life Sciences) for 1 h at room temperature, then washed and developed using an Bluephos AP developing reagent (SeraCare Life Sciences). Data were acquired by reading the absorbance at 595 nm using a Synergy H1 microplate reader (BioTek Instruments Inc.). Ratios were generated from αSMA/β-tubulin absorbance data and the results were normalized to vehicle. The fold change after 24 and 72 h relative to vehicle was then determined and depicted in the figures.

Soluble Collagen 1 ELISA:

Lung fibroblast conditioned supernatants were diluted 1:5 in DPBS. Purified Collagen 1 (STEMCELL Technologies Inc), diluted in 1:5 DBPS diluted complete medium, was utilized to generate an 8-point collagen 1 standard ranging from 200-0 ng/ml. Fifty microliters of the supernatants and standards were coated onto multisorb 96 well plates (Thermo Fisher Scientific) overnight at 4° C. After coating, the plates were washed and blocked with 200 µl of 3% BSA solution in DPBS (Lonza) for 1 h at room temperature on an orbital shaker. After blocking, plates were washed and 50 µl of 200 ng/ml biotin-conjugated anti collagen-1 antibody (Abcam Ab24821) was added to each well and the plates were incubated for 2 h at room temperature on an orbital shaker. After incubation, plates were washed and 50 µl of HRP-conjugated streptavidin (R&D systems, diluted as recommended by the manufacturer) was added to each well and the plates were incubated for 30 min at room temperature on an orbital shaker. Plates were then washed and the wells were developed by adding 100 µl of TMB peroxidase substrate solution (Fitzgerald Industries international) until sufficient color is observed, after which the reaction was stopped by adding 50 µl of 2N Sulfuric acid. Data were acquired by reading the absorbance at 405 nm using a Synergy H1 microplate reader (BioTek Instruments Inc.). The results were then graphed using Graph:Pad Prism version 7 (GraphPad Inc).

Isolation of Mixed Cells from IPF Explants:

Normal and IPF lung explants were placed into sterile PBS, washed, and transferred into fresh PBS. Tissue was minced and spun at 600×g for 5 min. Supernatants were collected with the PBS utilized to wash the explanted lungs (lung wash). The top layer of the pellet enriched in mechanically-dissociated cells and red blood cells (RBCs) were strained through a 70-µm strainer, the strainer washed repeatedly with DPBS until the RBCs and dissociated cells were free of the tissue pellet. These cells were centrifuged at 400×g for 5 min. RBC lysis buffer (Biolegend) was added, the remaining cells were counted, added to CryoStor CS10 freezing medium (STEMCELL Technologies Inc.), and viably preserved in liquid $N_2$.

Gene Expression Array Data Mining and Ingenuity IPA Analysis.

RNA was extracted from bronchial brushings from 6 IPF patients, and subjected to microarray analysis. Signal intensities for various chemokine receptors from normal and IPF bronchial brushings were mined. To generate a list of tyrosine kinases not targeted by BIBF1120, known BIBF1120 targets were excluded from analysis and remaining tyrosine kinases were added to a custom Ingenuity pathway generated using the Ingenuity database. Publicly available gene expression datasets (GSE24206) were mined from NCBI's geo datasets database. Groups were defined as follows—IPF lung biopsies vs normal lungs (early IPF) and IPF lung explants vs normal lungs (Advanced IPF). Gene expression values were extracted using NCBI's Geo2R gene expression analysis tool and the expression data were uploaded onto ingenuity IPA. Ingenuity IPA was set to only consider changes in gene expression of 1.5-fold or greater and $p \leq 0.05$. Tyrosine kinase expression values were overlaid onto the custom generated list of tyrosine kinases not targeted by BIBF1120 to generate the images shown.

Quantitative PCR Analysis.

Cells were lysed in Trizol™ reagent, RNA was extracted as recommended by the manufacturer and 1 µg of RNA was reverse transcribed into cDNA using superscript II reverse transcriptase (Life technology). Complementary DNA (cDNA) was subsequently loaded into a Taqman plate (Thermo-Fisher Scientific) and gene expression analysis were performed using predesigned primers and probes for human-CCR10, CCXCR1, CXCR4, ACTB and RNA18S5 (Thermo-Fisher Scientific). For chemokine receptors, chemokine ligands and tyrosine kinase expression analysis in sorted $CCR10^+$ cells, custom 384-well microfluidic cards containing predesigned primers and probes for the transcripts analyzed were purchased and utilized as recommended by the manufacturer (Thermo-Fisher Scientific). All Taqman analysis was performed using an Applied Bio system's Viia 7 instrument (Thermo-Fisher Scientific). The results were then exported, normalized to RNA18S5 expression (Thermo-Fisher Scientific) and fold change values were calculated using DataAssist software (Thermo-Fisher Scientific).

CCL28 Correlation Analysis:

Peripheral blood microarray gene expression datasets from normal and IPF patients (as part of the COMET-IPF cohort (Correlating Outcomes with Biochemical Markers to Estimate Time-Progression in Idiopathic Pulmonary Fibrosis) was mined for CCL28 transcript expression. The resulting expression values clustered into three expression taffies, and CCL28 low vs high were defined as lowest expression and the upper two expression tertiles, respectively. The expression of CCL28 was then correlated to progression free survival as defined by death or a decline in Forced Vital Capacity (FVC). Statistical analysis was then performed unadjusted or adjusted for gender, age and physiological score.

Mice:

Six to eight-week old, female, pathogen free NOD Cg-Prkdc$^{SCID}$ IL2rg$^{Tm1wil}$ Szi (NSG) or NOD.Cg-Prkdc$^{SCID}$ IL2rg$^{tm1Wil}$ Tg(CAG-EGFP) 10sb/SzJ (NSG-GFP) were purchased from Jackson Laboratories and housed in Cedars-Sinai Medical Center's high isolation animal rooms. NSG mice were allowed a minimum of one week to acclimate in the facility and then these mice either received nothing (i.e., non-humanized) $1 \times 10^6$ IPF cells by intravenous injection (i.e. humanized). In most in vivo experiments, the IPF cells used were removed from liquid $N_2$ storage, rapidly thawed, and washed in serum-free medium prior to injection into NSG mice. Humanized NSG mice received KB004 (i.e., anti-EphA3 mAb supplied by Kalobios; 5 mg/kg) or KB243 (i.e., appropriate IgG control supplied by Kalobios; 5 mg/kg) either from days 0 to 35 or from days 35 to 63 by intraperitoneal injection twice weekly. KB004 is an afucosylated mAb, which has been shown to target $EphA3^+$ cells via an antibody-dependent cell-mediated cytotoxicity (ADCC) mechanism. Other groups of humanized NSG mice received either vehicle (i.e., solutol) or BIBF1120 (Cayman Chemicals) by oral gavage beginning at day 35 after IPF cell injection. Vehicle or drug was administered 5 days a week until day 63 after IPF cell injection. All NSG groups were monitored daily and mice were sacrificed if there is evidence for morbidity such as weight loss of more than 20%, loss of fur, paralysis and/or lack of responsiveness when handled. At the indicated times after IPF cell injection, Broncho Alveolar Lavage (BAL) fluid and serum were collected for protein analysis, the superior and middle lobes were collected for biochemical hydroxyproline quantification, the inferior lobe and spleens for flow cytometric analysis, postcaval lobe for quantitative PCR analysis, and the left lung for histological analysis from each NSG mouse.

Detection of IL-12p70, IFNγ and TNFα in the BAL from Non-Humanized and Humanized NSG Mice.

Figure 21:
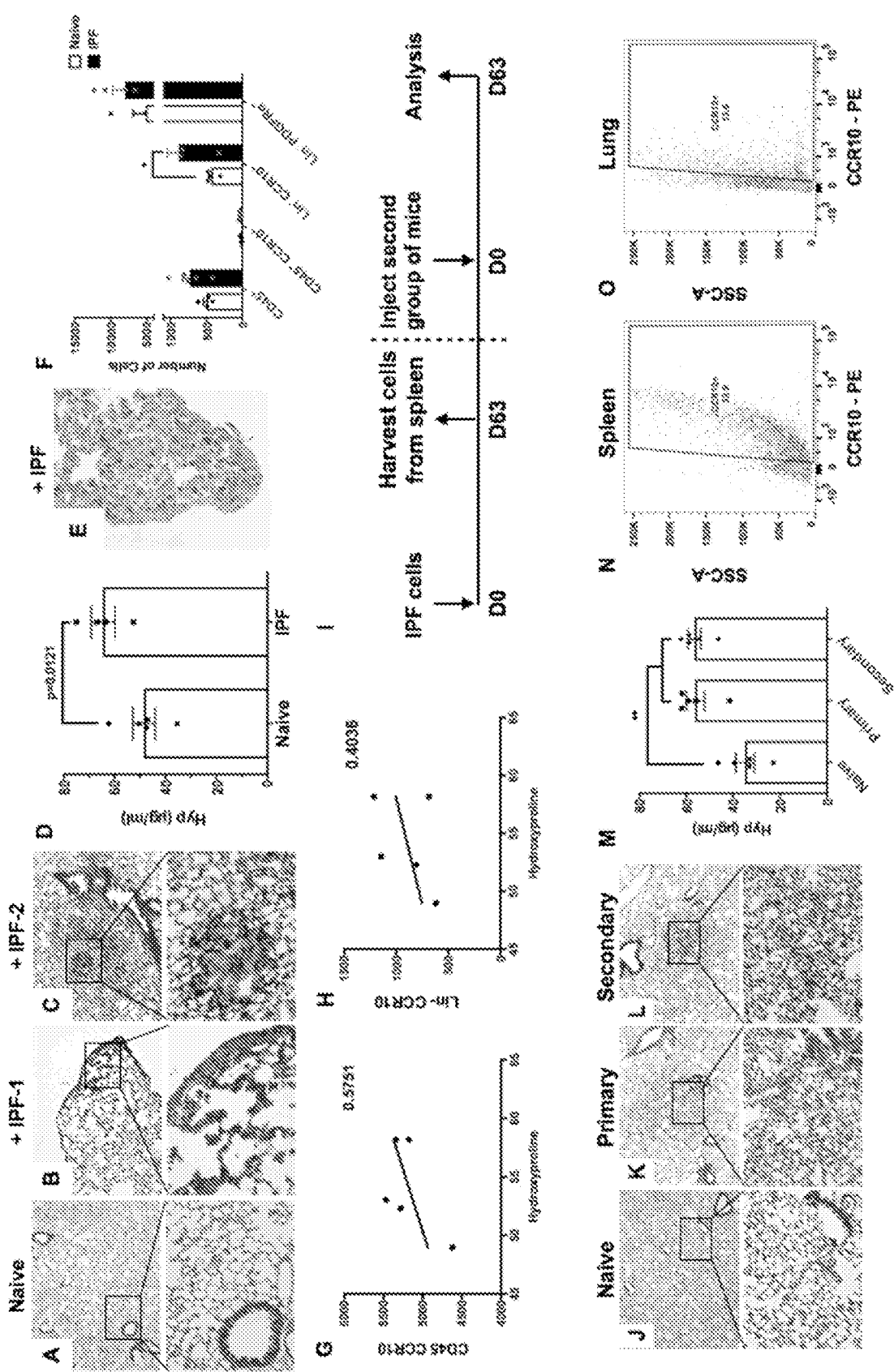
FIG. 21 shows IPF lung cells promote fibrosis in the lungs of NSG mice. (A-C) Representative images of Masson's trichrome staining of non-humanized NSG lung (A), and humanized NSG lungs (B&C) at day 63 after intravenous injection of IPF cells. Representative images were obtained at 50× (top) and 200× (bottom). n=5/group (D) Hydroxyproline in humanized and non-humanized NSG lungs. Data shown are mean±s.e.m.; n=5/group. p values indicated (E) Sixty-three days after IPF cell injection, lung samples from NSG-GFP mice stained for GFP protein. A representative image showing both the GFP+ cells (i.e. mouse) and the GFP$^-$ cells (i.e. introduced human) is shown at 200× (F) NSG-GFP lungs were analyzed by flow cytometry. Shown is the average number of GFP$^-$ cells, expressing human-CD45, CCR10, EpCAM and/or PDGFRα proteins in humanized (black) relative to non-humanized mice (white). Data shown are mean±s.e.m.; n=5/group. *$p \le 0.05$. (G-H) Correlation between hydroxyproline concentration and number of human CD45$^+$ CCR10$^+$ (G) and Lin$^-$ CCR10$^+$ (H) cells in NSG lungs, 35 days after IPF cell administration. n=5/group. (I) At day 63 after IPF cell injection into NSG mice (primary), spleen cells from this group were isolated and 1×10$^6$ of these cells were intravenously injected into a second group of NSG mice (secondary). Sixty-three days after injection, the lungs from these mice were analyzed. (J-L) Masson's Trichrome staining of lung samples from the non-humanized (J), primary NSG (K) and secondary NSG (L) groups. Representative images were obtained at 50× (top) and 200× (bottom). (M) Hydroxyproline in the lungs of both groups of humanized NSG compared with non-humanized NSG. Data shown are mean±s.e.m.; n=5/group. **p 0.01 (N-O) Representative dot plots for surface CCR10 expression in Lin$^-$ cells from the spleens (N) and lungs (O) of the secondary NSG group.
Figure 35:
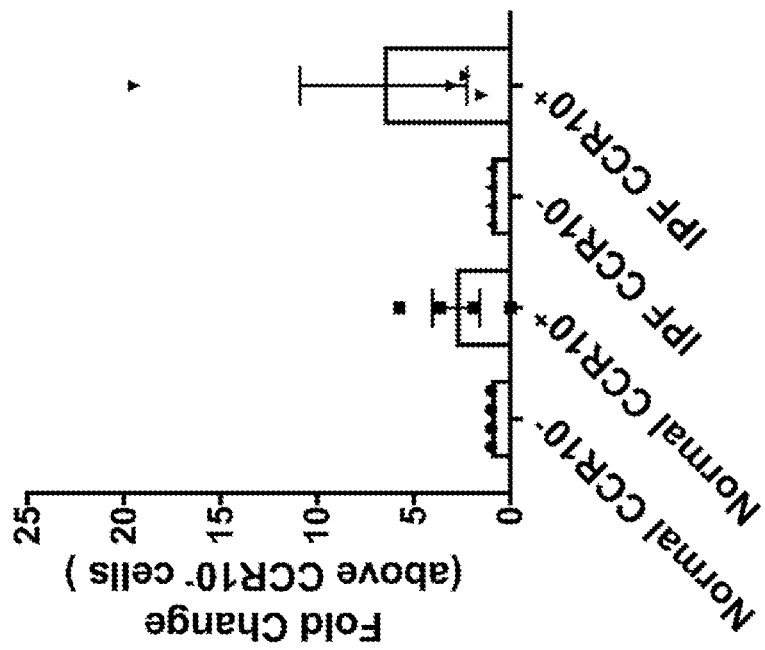
FIG. 35 shows enrichment for CCR10 transcript in magnetically-sorted CCR10$^+$ cells. Flow cytometry antibodies for CCR10 were validated by magnetic antibody-mediated purification of CCR10 expressing (i.e. CCR10$^+$) cells from normal and IPF lung explants followed by RNA extraction and qPCR analysis for the chemokine receptor in the sorted cells. Depicted is the average expression of CCR10 transcript in the sorted cells compared with non-sorted cells. Data are mean±sem; n=4.

Lungs in non-humanized and humanized NSG mice were washed using 1 ml of saline solution, and the resulting BAL was centrifuged to remove cells and the supernatants were stored at −80° C. until analysis. Mouse cytokines in the BAL were measured using predesigned Bioplex assays (Bio-Rad) as recommended by the manufacturer, Flow Cytometry:
Mouse Lung and Spleen Cells:

Murine lung cellular suspensions were generated using a mouse lung dissociation kit, C-tubes, and a GentleMacs dissociator (Miltenyi Biotech). Spleens were dissociated using a sterile rubber tip of 1 ml syringe plunger and 100 μm 50 ml tube filters (BD bioscience) as follows: isolated spleens were placed in 1 ml of sterile complete medium until all the samples were collected. Sterile 50 ml conical tube filters were placed on top of sterile 50 ml conical tubes and were equilibrated by pipetting 1 ml of calcium and magnesium free DPBS (DBPS; Cellgro) through the filters. Spleens were transferred to a sterile 50 ml filter, cellular suspensions were generated using a sterile rubber tip of a syringe plunger, and splenic material was flushed with 5 ml of DPBS. Lung and splenic cell suspensions were centrifuged and resuspended in 1 ml of RBC lysis buffer (Biolegend), incubated at room temperature for 1-2 min and then equilibrated by adding 25 ml of DPBS to each tube. Cells were centrifuged and resuspended in flow cytometric wash/staining buffer (DPBS+2% FBS) in the presence of human and mouse Fc receptor blocking antibodies (Biolegend). Cells were then stained with anti-human-CD45, -EpCAM and -CCR10 antibodies for 20 min at 4° C. Unstained, isotype controls, fluorescent minus one controls and staining in non-humanized murine lung and spleen suspensions were utilized to gate out any non-specific antibody binding and background fluorescence. CCR10 antibodies were validated via the enrichment for CCR10 transcripts in magnetically sorted CCR10+ cells versus non-sorted normal and IPF explant cells (FIG. 35). Flow cytometric data were acquired within one week of staining using a LSR Frotessa (BD Biosciences) or MACSQuant 10 (Miltenyi Biotech) flow cytometers and data were analyzed using Flowjo software V10.2 (Treestar Inc.). GFP− cells and gating strategies are summarized in FIGS. 36A & 36B). The resulting gates from non-humanized NSG-GFP mice were used to identify human CD45-, EPCAM-, CCR10-, and PDGFRα-stained cells (FIGS. 36C & 21F).

Human Lung Cell Suspensions:

Human lung cells were added to flow cytometry wash/staining buffer, and blocked with anti-human Fc receptor antibodies (Biolegend) for 15 min at 4° C. After blocking, cells were stained with PE conjugated anti-human CCM 0 (Biolegend), BV421 conjugated anti-human EpCAM (Biolegend), PE/Cy7 conjugated anti-human CD45 (Biolegend) or biotin-conjugated anti-human EphA3 (supplied by Kalobios) and FITC-conjugated strepdavidin (ThermoFisher Scientific) for 20 min at 4° C. Cells were then washed twice with flow cytometry wash/staining buffer, and fixed in 5% neutral buffered formalin (NBF). Flow cytometric data were acquired using a BD LSR Frotessa (BD Biosciences) or MACSQuant 10 (Miltenyi Biotech) flow cytometers and data were analyzed using Flowjo software V10.2 (Treestar Inc.).

Lung Fibroblasts:

Lung fibroblasts were plated and treated as described above. At the conclusion of an experiment, fibroblasts were trypsinized, washed and resuspended in flow cytometric wash/staining buffer containing anti-human Fc receptor blocking antibodies (Biolegend). Cells were then stained with APC-conjugated anti-EphA3 antibodies (supplied by KaloBios) for 20 min at 4° C., washed, and fixed in 5% NBF solution. Flow cytometric data were acquired using a MACSQuant 10 (Miltenyi Biotech) flow cytometer and data were analyzed using Flowjo software V10.2 (freest& Inc.).

Magnetic Cell Sorting:

Lung explant cells were stained with PE-conjugated anti-CCR10 antibodies (Biolegend) and then magnetically sorted using anti-PE microbeads (Miltenyi Biotech) as recommended by the manufacturer.

Histological Analysis:

Lung tissue was fixed in 10% NBF solution for 24 h and subsequently transferred into tissue cassettes and kept in a 70% ethanol solution for approximately 24 h, Lungs were then processed using routine histology techniques and stained using Masson's trichrome. A Zeiss Axio Observer Z1 microscope and the Zeiss Zen 2012 v 1.1.2.0 software (Zeiss) were used to obtain representative images.

Immunohistochemistry:

Slides containing 4 μm sections were deparaffinized and hydrated by incubating them in two changes of xylene for five min each, followed by 2 changes of 100% ethanol for 3 min each, 70% ethanol for 2 min, 50% ethanol for 2 min, and distilled water for 5 min. Antigen retrieval was performed by incubating the slides in 10 mM Citric acid solution (pH 6.0) in an 80° C. oven overnight. The slides were subsequently washed in PBS and permeabilized in 10% methanol containing 0.4% $H_2O_2$ for 30 min. After permeabilization, slides with murine tissues were washed and stained with a rabbit anti-human CCR10 or rabbit anti-GFP antibodies (Abcam). IHC analysis for CCR10 on human lung biopsies or explants were performed using a rabbit anti-human CCR10 (Abcam) antibody. Dual color IHC was performed using a dual color IHC kit (Enzo Lifesciences), rabbit anti-human CCR10 (Abcam) and mouse anti-human EphA3 (Clone, SL2, Kalobios) antibodies as recommended by the manufacturer. Immunofluorescence staining was completed by washing the slides following primary antibody incubation and subsequent incubation with fluorescent probe conjugated secondary antibodies for 1 h at room temperature. Slides were then washed and mounted using a DAPI containing mounting medium (Thermo Fisher Scientific). IHC staining for lung fibroblasts as briefly outlined: cells were fixed using 4% formaldehyde solution for 10 mi at room temperature. The cells were then, washed, permeabillzed by incubating them in 10% methanol solution for 5 min and stained with anti-EphA3 antibodies followed by HRP conjugated secondary antibodies and DAB developing reagent. Images were acquired using an AxioCam MRc camera Zeiss AX10 microscope using a 5× (0.16aperture) and 20× (0.8 aperture) lenses (Carl Zeiss Microscopy GmbH) at room temperature and Zen 2012 (Blue edition) v 1.1.2.0 software.

Hydroxyproline Assay:

Total lung hydroxyproline was analyzed. Superior and middle lobes were surgically dissected, and placed into 5 ml sterile tubes and flash frozen until all the samples have been collected. On the day of the assay, tissues were thawed and 500 μm of distilled water ($dH_2O$) was added to the tissues. Tissues were homogenized using a micro-sample homogenizer (Pro Scientific) as follows: the homogenizing tip was washed in 70% ethanol, then $dH_2O$ and then utilized to homogenize the tissues. The homogenizer was washed in dH$_2$O between samples and a new batch of dH$_2$O was utilized after 5 samples. After homogenization, samples were transferred into Fisherbrand Borosilicate glass screw capped tubes with a rubber liner (Fisher Scientific) and 560 μl of 12N HCl was added to the homogenized tissues. Samples were capped, vortexed, placed into a preheated oven set to 120° C. and incubated overnight. The next morning, samples were cooled down to room temperature, vortexed and filtered through a 0.45 μm syringe filter. Fifty microliters of the filtered samples were transferred into a 1.5 ml micro-centrifuge tube and evaporated on a heating block at 100° C. for 2-3 h. While the samples were incubating, standards to generate a standard curve were prepared by diluting Hydroxyl-L-Profine (Sigma Aldrich) in Acetate-citrate buffer (17 g Sodium Hydroxide (Sigma-Aldrich), 36 g Sodium Acetate (Sigma-Aldrich), 25 g Citric acid (Sigma-Aldrich), 6 ml of Glacial Acetic acid (Thermo-Fisher Scientific) and a final pH of 6 in a total of 500 ml ddH$_2$O) into nine different concentrations ranging from 200 μg/ml to 20 μg/ml. After incubation, the desiccated sample pellets were resuspended in 50 μl of Acetate-citrate buffer and all samples and standards (50 μl) were transferred into 5 ml tubes. One ml of Chloramine-T solution (1 g Chloramine T hydrate (Sigma-Aldrich) dissolved in 8 ml n-Propanol (Sigma-Aldrich) and 8 ml of ddH$_2$O and then supplemented with 64 ml Acetate-Citrate buffer) was added to each sample and standard and mixed by brief vortexing. Samples and standards were incubated at room temperature for 20 min and subsequently 1 ml of Ehrlich's solution (6.75 g 4-(dimethylamino)-benzaldehyde, 26 ml n-Propanol and 14 ml of 60% Perchloric acid) was added and all tubes were mixed by vortexing, transferred into a pre-heated oven set at 65° C. and incubated for 20 min. Samples and standards were then removed and cooled for 10 min without light exposure. Finally, 200 μl of each sample and the standards were transferred into a flat-bottom 96 well plate and absorbance at 550 nm was recorded using a BioTek Synergy H1 microplate reader (BioTek Instruments Inc.). Sample concentrations were calculated using an equation generated from the standard curve.

Statistical Analysis:

All statistical analyses were performed using GraphPad Prism software version 7 (GraphPad).

CCR10 is Significantly Increased in Rapidly Progressive IPF.

Figure 18:
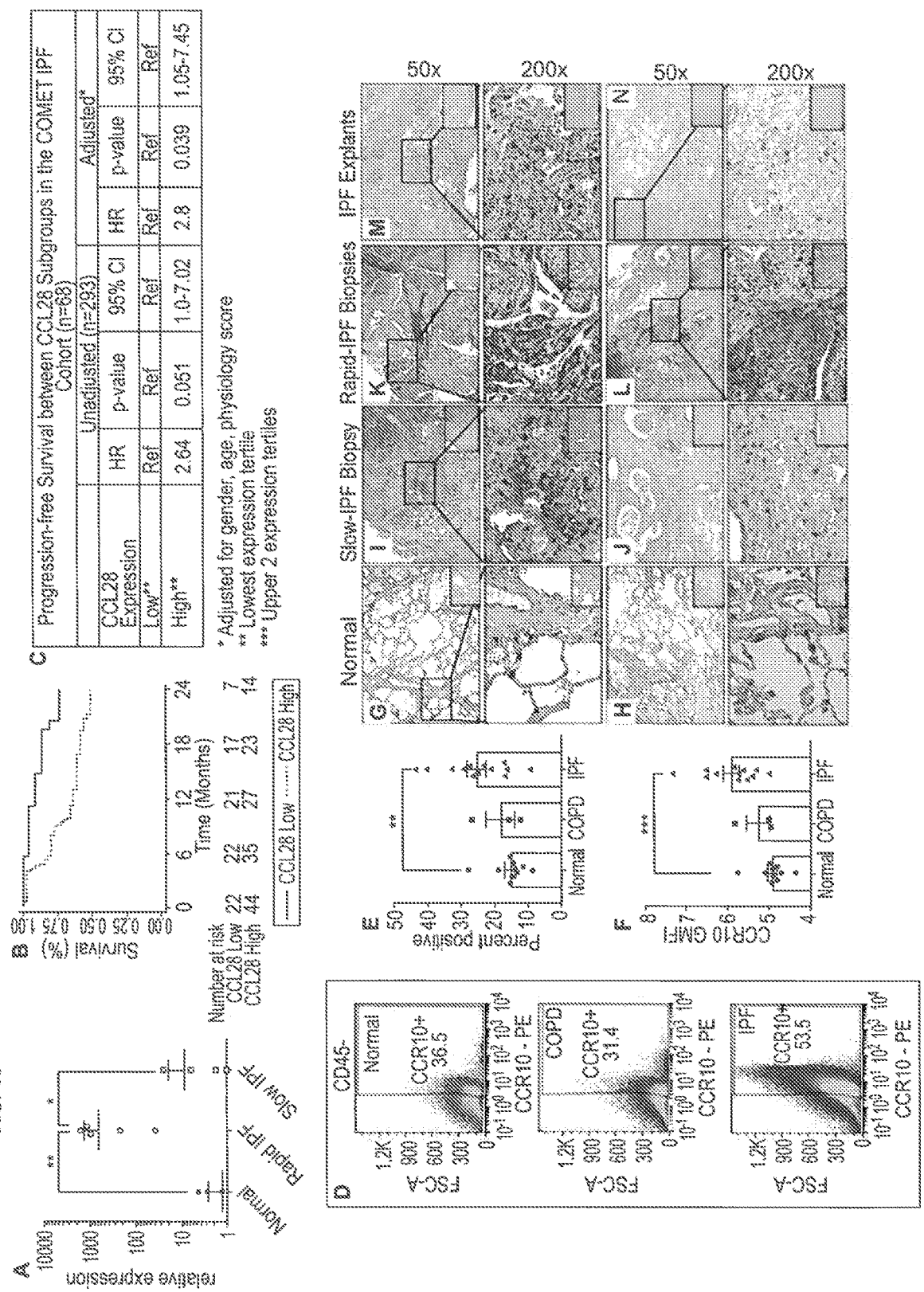
FIG. 18 shows CCR10 expression in normal and IPF lungs. (A) Transcriptomic analysis of lung samples (normal and rapid- and slow-IPF) for CCR10 transcripts. Data shown are mean±s.e.m.; n=4-9/group. (B) Correlation analysis of peripheral blood CCL28 transcript expression and progression free survival, as defined by death or FVC decline in 68 IPF patients over 24 months. (C) Depicted is the unadjusted and gender, age and physiological score adjusted statistical analysis for CCL28 transcript expression and IPF patient progression free survival. (I)) Flow cytometric analysis of mechanically dissociated normal and IPF lung explant cellular suspensions for cell surface CD45 and CCR10 proteins. Depicted are representative dot plots (B) of CCR10 expression in CD45$^-$ cells from normal (left), COPD (middle) and IPF (right) lung explants. (E-F) Depicted is the average percentage of CD45$^-$ cells expressing CCR10 and the geometric mean fluorescence intensity of CCR10 expression in CD45$^-$ CCR10$^+$ cells (F) from normal (n=10), COPD (n=3) or IPF (n=13) lung explants. *$p \le 0.05$$p \le 0.01$*$p \le 0.001$****$p \le 0.0001$ (G-N) IHC analysis for CCR10 protein expression in normal lung explants (G-H), Slow-IPF (I-J), Rapid-IPF lung biopsies (K-L) and IPF lung explants (M-N). Shown are representative images acquired at 50× (top) and 200× (bottom) magnification. The corresponding IgG isotype control staining is shown in the inlayed images. n=3-15 lung samples/group.
Figure 19:
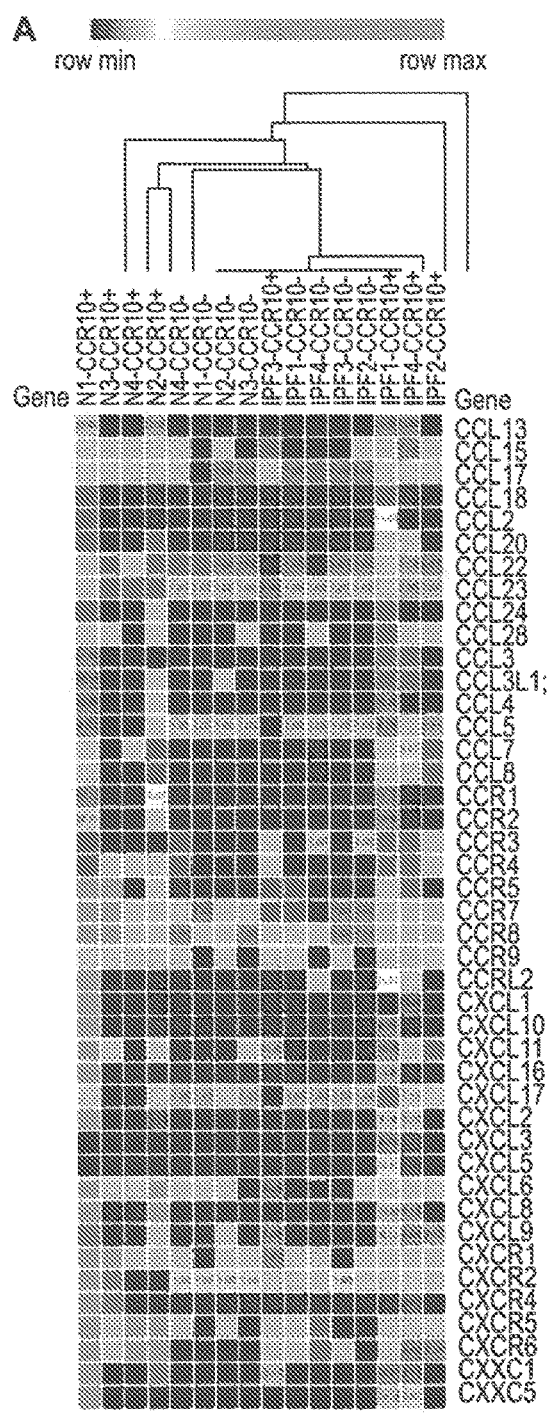
FIG. 19 shows transcriptomic analysis of CCR10$^+$ and CCR10$^-$ cells in normal and IPF lung explants. RNA was purified from magnetically sorted CCR10$^+$ and non-sorted CCR10$^-$ cells from normal (n=4) and IPF (n=4) lung explants followed by qPCR analysis. Heat maps were generated using Morpheus (https://software.broadinstitute.org/morpheus/) indicating the relative expression values for transcripts encoding various chemokine receptors and ligands (A) and tyrosine kinases (B) in CCR10$^+$ cells relative to non-sorted CCR10$^-$ cells.
Figure 19:
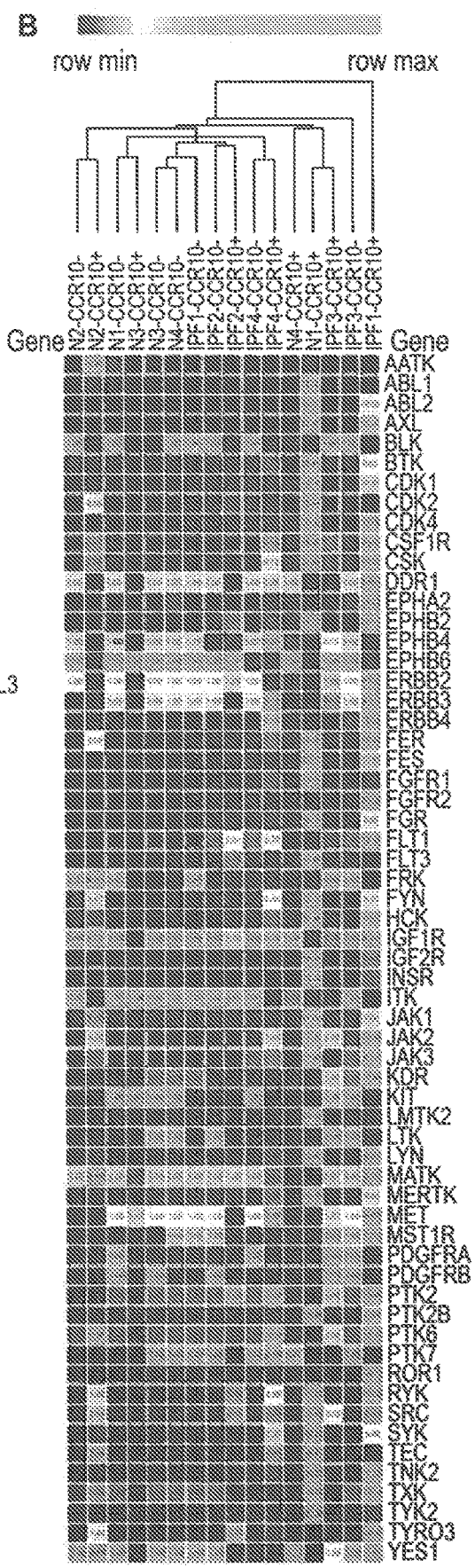

Although variable progression is described in IPF, the mechanisms accounting for this variability are poorly understood. Without wishing to be bound by any particular theory, we believe that the recruitment of immune cells and/or the activation of both immune and structural cells via chemokine receptors modulate the progression of IPF. Unexpectedly, CCR10 transcripts were significantly elevated in IPF biopsies from rapidly progressive patients (i.e., Rapid-IPF) compared with either slow-IPF lung biopsies or normal donor lung samples (FIG. 18A). Further, peripheral blood CCL28 (a CCR10 ligand) transcript levels were significantly correlated with reduced progression free survival (FIG. 18B-C) in the COMET IPF cohort. Flow cytometric analysis of CD45 negative structural cells in lung explant cellular suspensions showed a significant increase in CCR10$^+$ cells (FIG. 18D-E) and their CCR10 GMFI (FIG. 18F) in IPF relative to COPD and Normal lungs. Immunohistochemical (IHC) analysis showed that CCR10$^+$ interstitial cells were rarely observed in normal lung explants (FIG. 18G-H) but were most abundant in rapid-IPF lung biopsies (FIG. 18K-L) compared with slow-IPF lung biopsies and IPF lung explants (mainly from slow-IPF patients) (FIGS 18I-J & 18M-N, respectively). Quantitative PCR analysis of magnetically sorted CCR10$^+$ cells relative to non-labeled CCR10$^-$ cells showed differential chemokine receptor and ligand expression of IPF relative to normal lung derived cells, as evident by the differential clustering of normal and IPF CCR10$^+$ cells (FIG. 19A). Further, both normal and IPF CCR10$^+$ cells expressed unique tyrosine kinases compared with CCR10$^-$ cells (FIG. 19B). Collectively, these results demonstrate that CCR 10$^+$ cells are significantly increased in rapid-IPF compared with normal and stable-IPF and that CCR10$^+$ cells in normal and IPF lungs express similar tyrosine kinases but distinct chemokine receptors and ligands.

Figure 20:
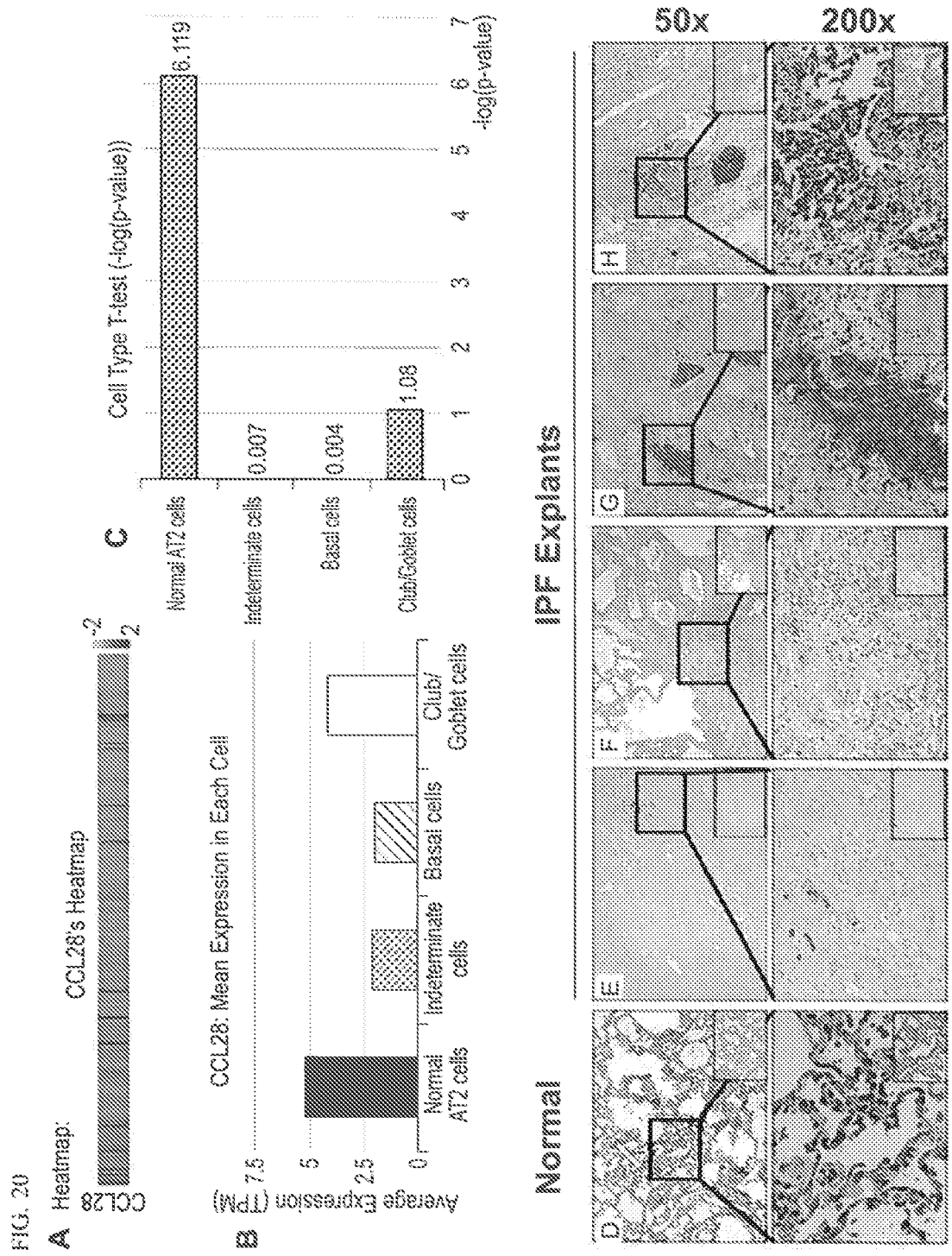
FIG. 20 shows CCL28 transcript and protein expression in normal and IPF lungs. (A-C) Publicly available single cell RNAseq datasets of normal type II alveolar epithelial cells (AT2 cells) and IPF epithelial cells were mined for CCL28 transcript expression. Depicted is a heat map (A) and average TPM expression (B) and the −log(p-value) (C) for CCL28 transcript expression in normal and IPF epithelial cells. (D-H) Representative images of CCL28 staining in normal (D) and IPF (E-H) lung explants. Shown are images taken at 50× (top) and 200× (bottom) magnification. n=1-4/group.

One explanation for the increased numbers of CCR10$^+$ cells in IPF might stem from the increased presence of its ligands CCL27 and CCL28 in the lungs of these patients. CCL27 was not present in gene array datasets of normal and IPF lungs; however, CCL28, was present in normal AT2 cells but not in IPF epithelial cells (FIG. 20A-C). CCL28$^+$ cells were diffusely detected by IHC in normal lung explants (FIG. 20D) but focally detected in a subset of IPF lung explants (FIG. 20G-H vs. 20E-F). Thus, these results show that CCL28 is expressed by normal AT2 cells and in focal regions in IPF lung explants.

Human CCR10$^+$ Cells Promote Fibrosis in NSG Mice Following Intravenous Injection.

Figure 22:
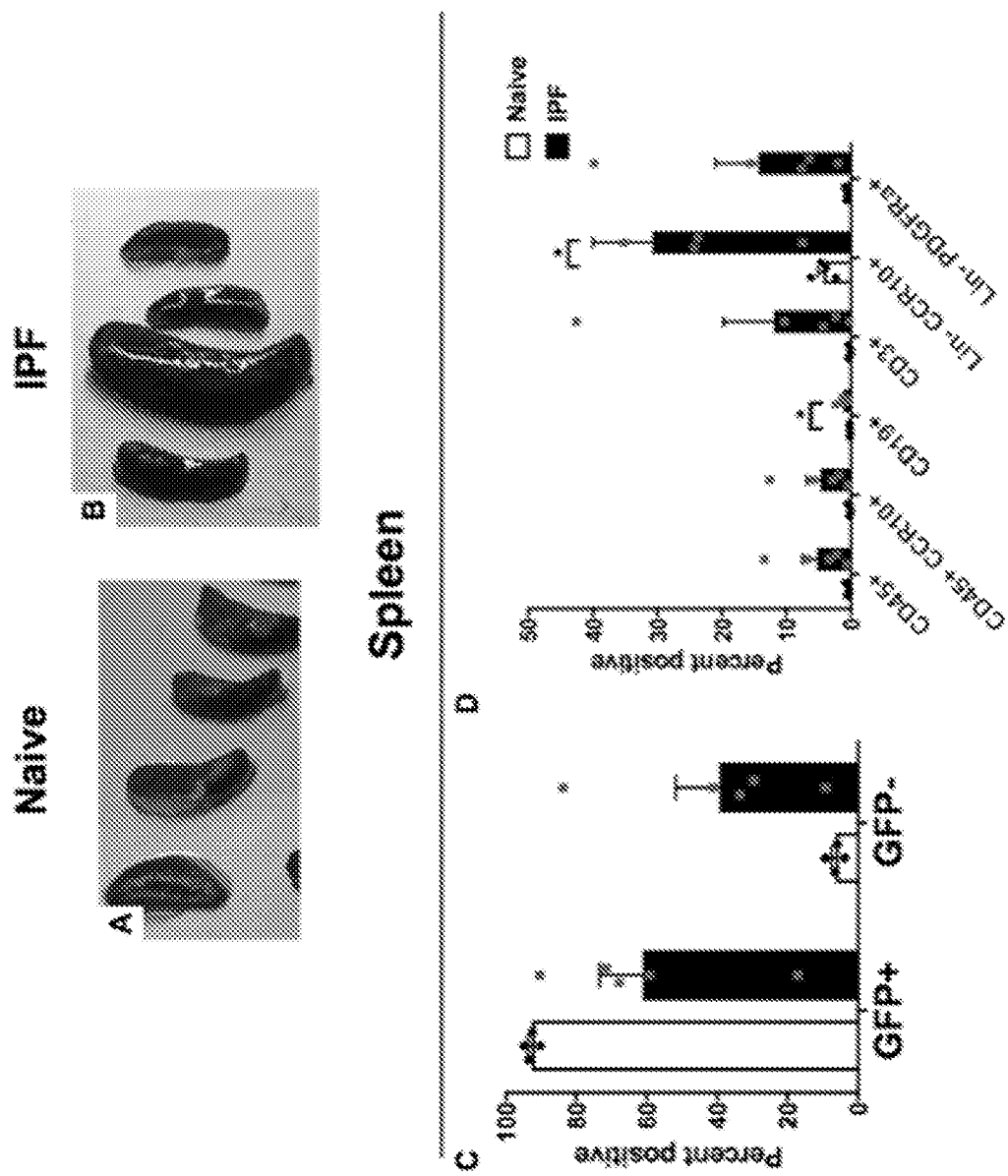
FIG. 22 shows abundance of xenografted GFP-human cells in NGS-GFP murine spleens. GFP-NSG or NSG mice were IV administered with IPF lung explant cells; 35-63 days after cellular administration, spleens were collected and cellular suspensions were generated for flow cytometric analysis. (A-B) Depicted are images for non-humanized (A) and humanized (B) NSG murine spleens, 63 days after cellular administration. (C-D) Depicted is the average percentage GFP$^+$ and GFP$^-$ cells (C) and GFP$^-$ cells staining for human CD45, EpCAM, CCR10, CD19, CD3 and/or PDGFRα proteins (D) in non-humanized and IPF lung explant challenged mice. *$p \le 0.05$

Compared to naive (i.e., non-humanized) NSG mice (FIG. 21A), fibrosis was observed histologically in the lungs of humanized mice (FIG. 21B-C) at day 63 after intravenous injection of IPF cells. Further, hydroxyproline was significantly elevated in humanized NSG mouse lungs compared with non-humanized NSG lungs (FIG. 21D). Thirty-five days after cell injection into NSG mice that were transgenic for EGFP (or NSG-GFP), GFP$^-$ cells were present in NSG-GFP lungs (FIG. 21E). Relative to non-humanized NSG-GFP mice, GFP$^-$ Lin$^-$ CCR10$^+$ (FIG. 21F) cells were significantly increased in humanized mice and there was a positive correlation between the number of CD45$^+$ CCR10$^+$ (FIG. 21G) and Lin$^-$ CCR10$^+$ (FIG. 21H) cells and hydroxyproline concentration in the lungs. Humanized NSG-GFP mice had enlarged spleens relative to non-humanized mouse spleens (FIG. 22A-B), where there was a marked decrease in the percentage of mouse GFP$^+$ cells and a concomitant increase in the percentage of human GFP$^-$ cells (FIG. 26C), Further characterization of human GFP– cells revealed increased percentages of CD45$^+$, CD45$^+$ CCR10$^+$, CD19$^+$, CD3$^+$ and Lin$^-$ PDGFRα$^+$ cells (FIG. 26D) compared with non-humanized SCID spleens. However, the majority of the GFP$^-$ cells in the spleens of humanized mice were Lin$^-$ CCR10$^+$ cells (FIG. 22D). Together, these findings demonstrate that CCR10$^+$ human cells engraft in NSG and NSG-GFP mice, and the presence of these cells positively correlate with lung fibrosis in these mice.

CCR10$^+$ Human Cells Transfer Fibrotic Lung Disease in NSG Mice.

Figure 23:
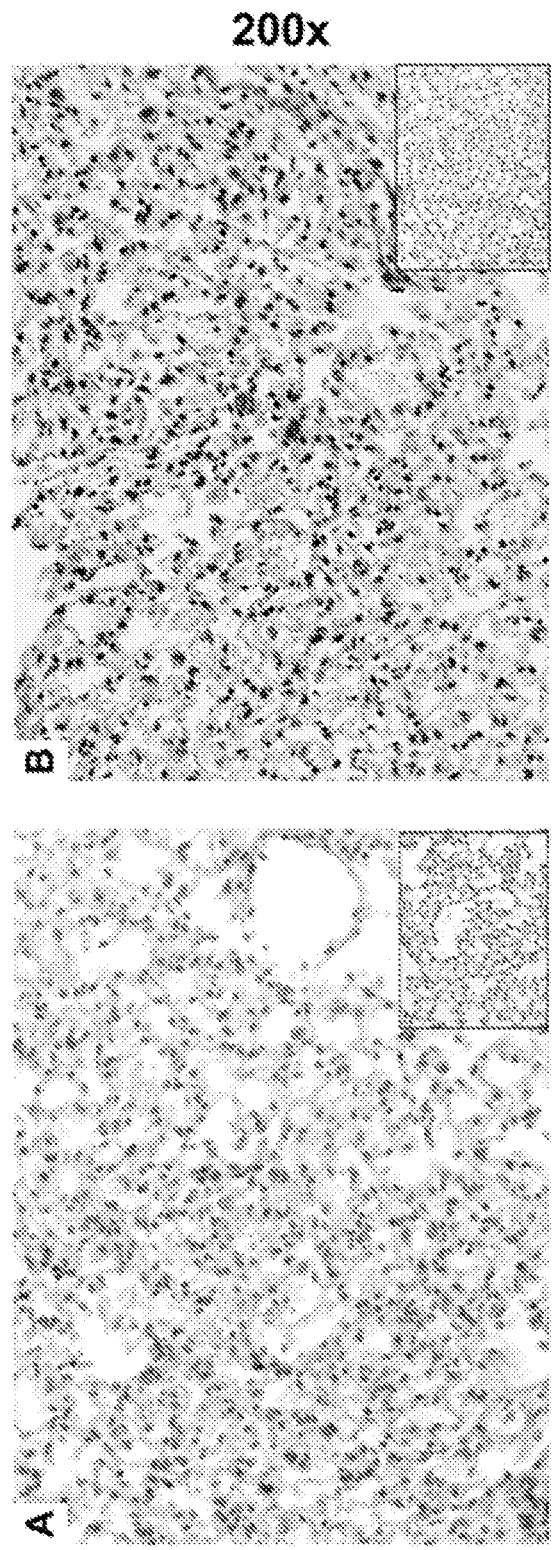
FIG. 23 shows that CCR10$^{30}$ cells are present in the lungs of primary and secondary humanized NSG mice. IPF explant cells were injected intravenously into a group of NSG mice (primary). Sixty-three days after injection, NSG lungs were collected for histological analysis, and spleens were collected for cell isolation. One million cells isolated from the spleens of this group were subsequently injected intravenously into a second group of NSG mice (secondary). At day 63 after injection, the lungs of this secondary group of NSG mice were collected for histological analysis. (A-B) Shown are representative images of mouse lungs from primary (A) and secondary (B) NSG mouse groups stained with isotype IgG control (inlay) or an anti-CCR10 antibody.
Figure 24:
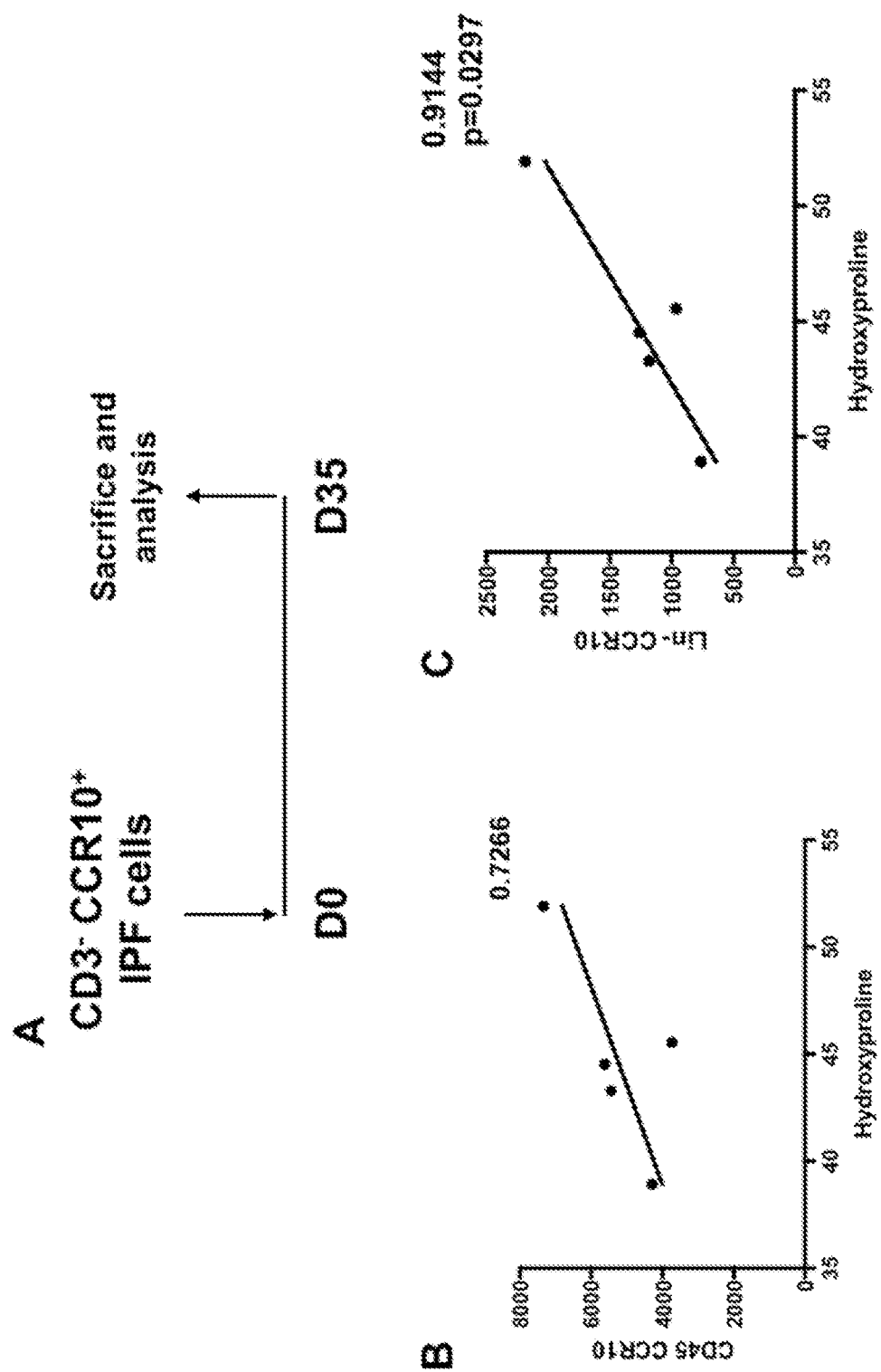
FIG. 24 shows CCR10$^+$ cells in the lungs of humanized NSG mice positively correlate with hydroxyproline. (A) CD3$^-$ CCR10$^+$ IPF lung cells were sorted and injected intravenously into NSG mice. At day 35 after IPF cell injection, lungs were analyzed using flow cytometry and an hydroxyproline assay. (B-C) Depicted are correlation analyses of hydroxyproline and number of human CD45$^{30}$ CCR10$^{30}$ (B) and Lin$^-$ CCR10$^+$ (C) cells in NSG lungs at day 35 after cell injection, n=5/group.

To determine whether human CCR10$^+$ cells transferred fibrotic lung disease from one cohort of NSG mice to another, human cells were purified from NSG spleens at day 63 after IPF cell administration (primary) and intravenously introduced into a new group of NSG mice (secondary). At day 63 after injection, this secondary group of NSG mice was analyzed for human cell engraftment and pulmonary remodeling (FIG. 21I). Masson's trichrome staining of lungs from humanized NSG mice revealed fibrosis in both the primary and secondary NSG groups (FIG. 21K-L) but not in a non-humanized NSG group (FIG. 21J). Hydroxyproline was significantly elevated in both the primary and secondary groups relative to non-humanized lungs (FIG. 21M), and Lin⁻ CCR10⁺ cells in spleen (FIG. 21N) and lung (FIG. 21O) were observed in the secondary group. Further. CCR10⁺ cells were detected histologically in lung from both NSG groups (FIG. 23A-B). Finally, 35 days after injection of sorted CCR10⁺ cells (FIG. 24A), the number of CD45⁺ CCR10⁺ (FIG. 24B) and Lin⁻ CCR10⁺ (FIG. 24C) cells all strongly correlated with hydroxyproline levels in humanized NSG mice. Thus, these results demonstrate that CCR10⁺ cells engraft, initiate, maintain, and transfer fibrotic lung disease in NSG mice.

BIBF1120 did not modulate CCR10⁺ IPF Cell-Induced Fibrosis in NSG Mice.

Figure 25:
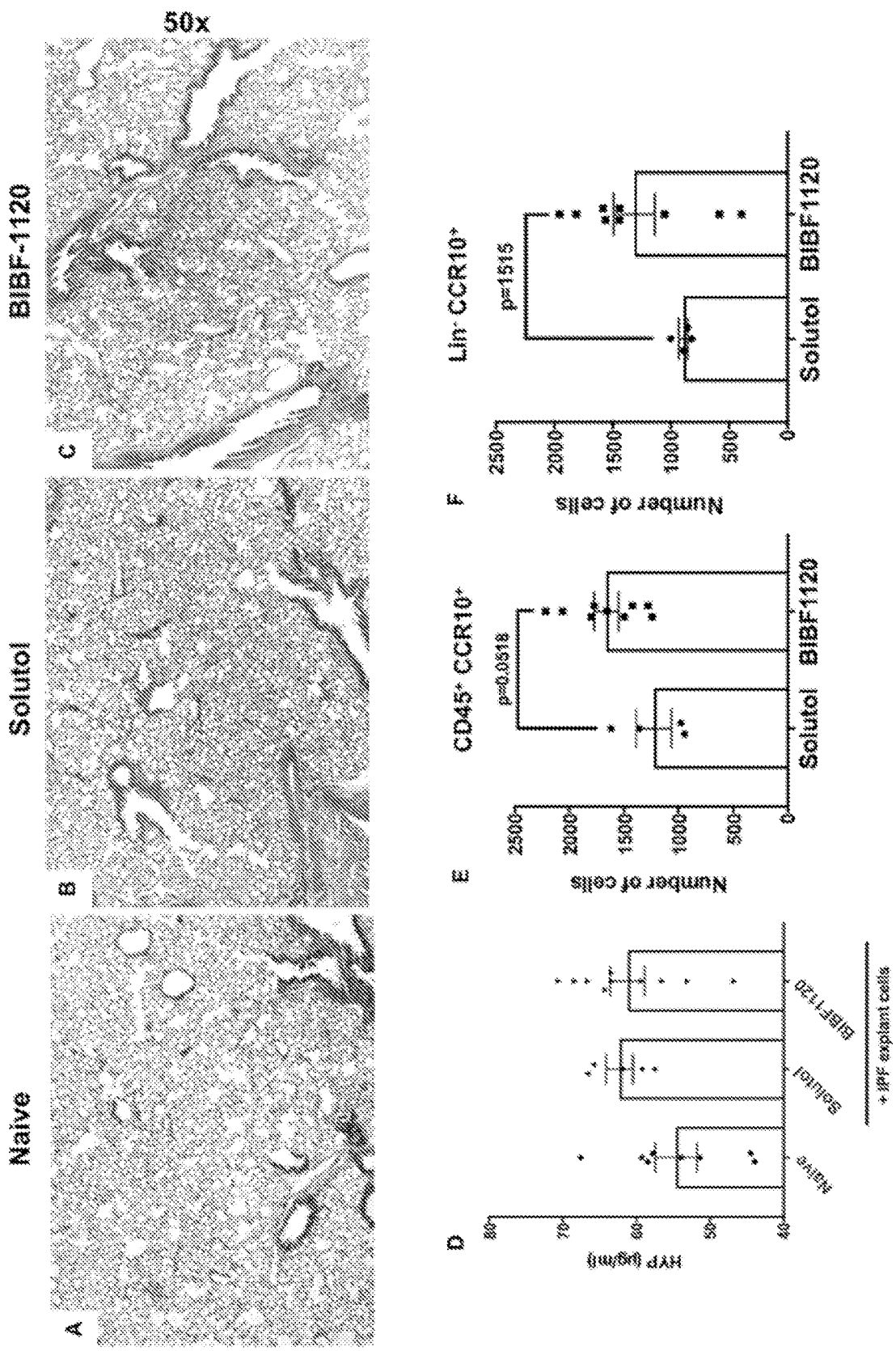
FIG. 25 shows that CCR10$^+$ were increased in humanized NSG mice treated with BIBF-1120. IPF cells were injected intravenously into NSG mice and beginning at day 35 after injection mice were treated either with a solutol vehicle or 60 mg/kg BIBF-1120 solubilized in solutol for 5 days a week over 4 weeks. (A-C) Depicted are representative images of Masson's Trichrome staining of non-humanized (A) and humanized NSG mice that received solutol (B) or BIBF-1120 (C). (D) Depicted is the hydroxyproline in the lungs of non-humanized or humanized NSG mice that received solutol or BIBF-1120. Data are mean±s.e.m.; n=5-10/group. (E-F) Solutol- or BIBF1120-treated NSG humanized mouse lungs were analyzed by flow cytometry for human CD45, EpCAM and/or CCR10 expression. Depicted is the average number of $CD45^+$ $CCR10^+$ (E) and $Lin^-$ $CCR10^+$ (F) cells in humanized NSG mice treated with solutol or BIBF1120. Data are mean±s.e.m.; n=5-10/group. p values indicated

To determine the efficacy of nintedanib in the humanized NSG model, groups of NSG mice received human IPF cells and treated with 60 mg/kg of Nintedanib/BIBF1120 solubilized in solutol vehicle or solutol alone weekly beginning at day 35 after IPF cell injection (i.e., when pulmonary fibrosis is established in this model). Unlike non-humanized NSG lungs (FIG. 25A), both vehicle—(FIG. 25B) and BIBF1120—(FIG. 25C) treated NSG groups showed lung fibrosis at day 63 after IPF cell injection. Lung hydroxyproline was elevated in both groups compared with non-humanized NSG lungs (FIG. 25D). Further, BIBF1120-treated NSG lungs contained greater CD45⁺ CCR10⁺ and Lin⁻ CCR10⁺ (FIGS. 25E & 25F, respectively) compared with vehicle-treated NSG groups. Collectively, these results demonstrate that BIBF1120 treatment was ineffective at modulating fibrosis in a humanized NSG model of IPF, potentially due to the activation and/or expansion of CCR10⁺ cells.

CCR10⁺ IPF Cells Express the Tyrosine Kinase Receptor EphA3.

Figure 26:
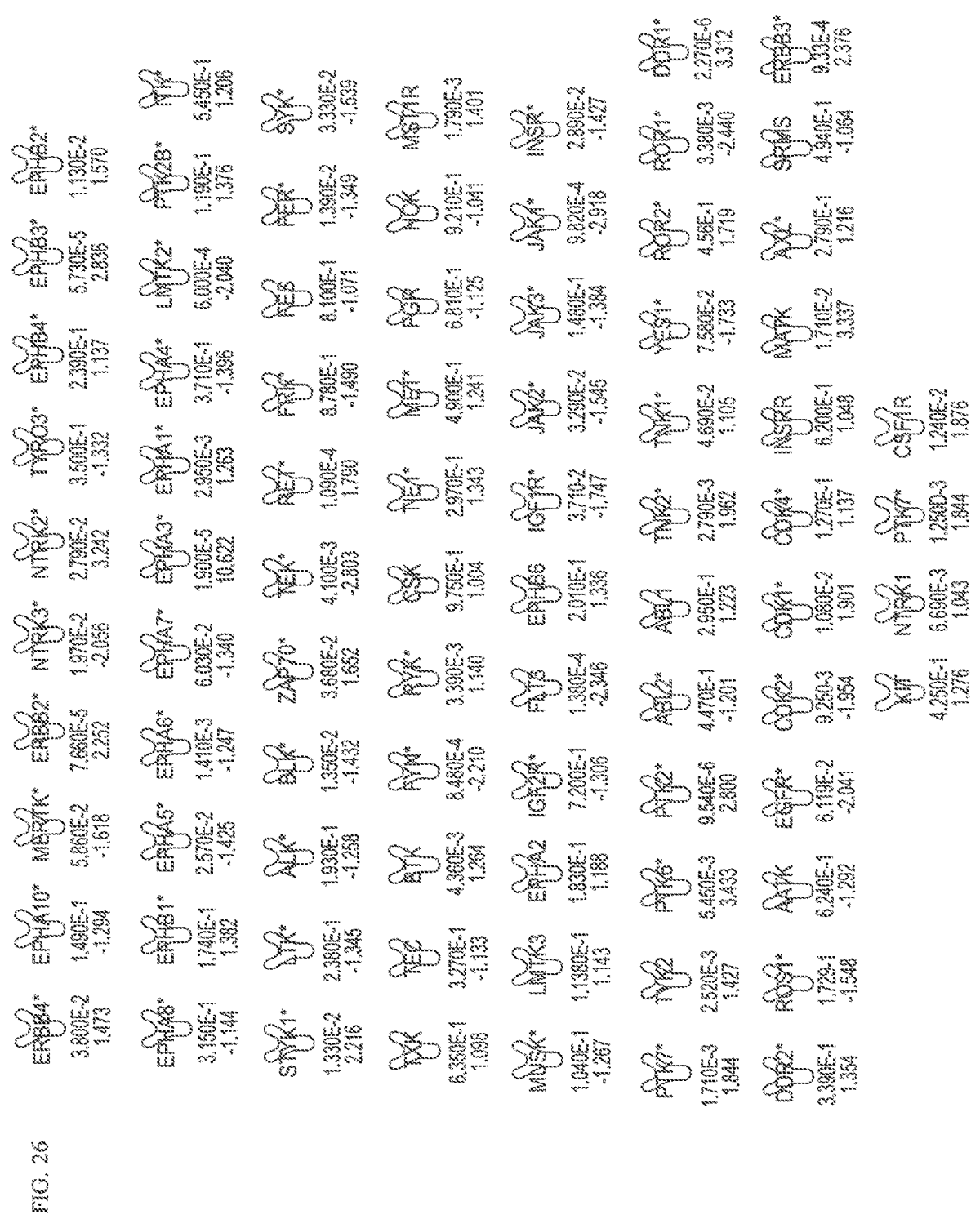
Figure 27:
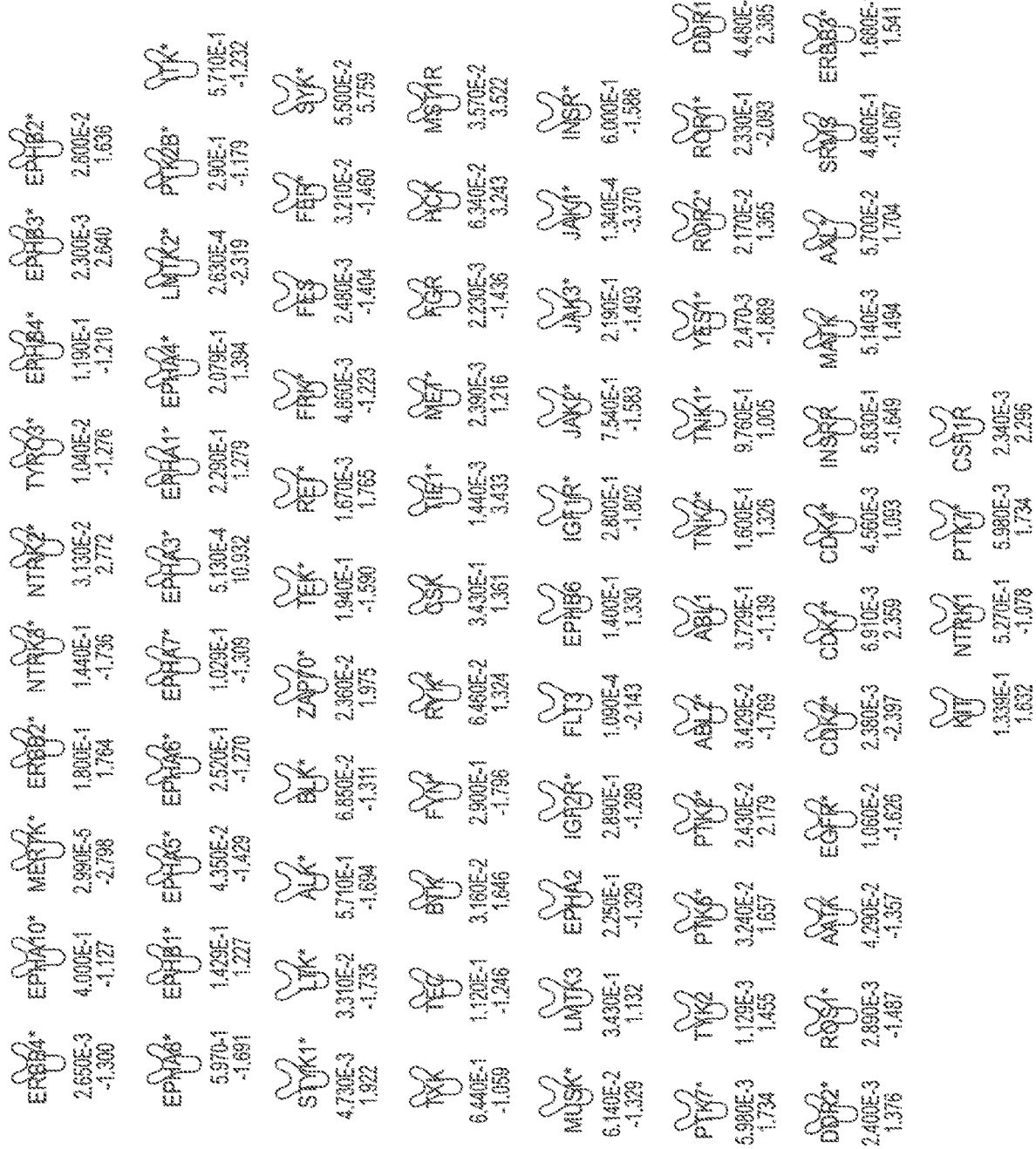
FIG. 27 shows transcript expression of tyrosine kinases that are resistant to nintedanib in IPF lung explants. Publicly-available transcriptomic datasets were analyzed using Geo2R and uploaded onto ingenuity's Integrated. Pathway Analysis (IPA). Tyrosine kinases not inhibited by BIBF1120 were added into a custom pathway designer in ingenuity IPA. Fold changes and p-values of transcript expression for these kinases in IPF compared with normal lung biopsies (GSE24206) is shown. Up- and down-regulated transcripts are depicted in red and green, respectively. Top and bottom values depict p-values and fold changes in expression, respectively, n=6 normal; n=4 IPF lung explants.
Figure 28:
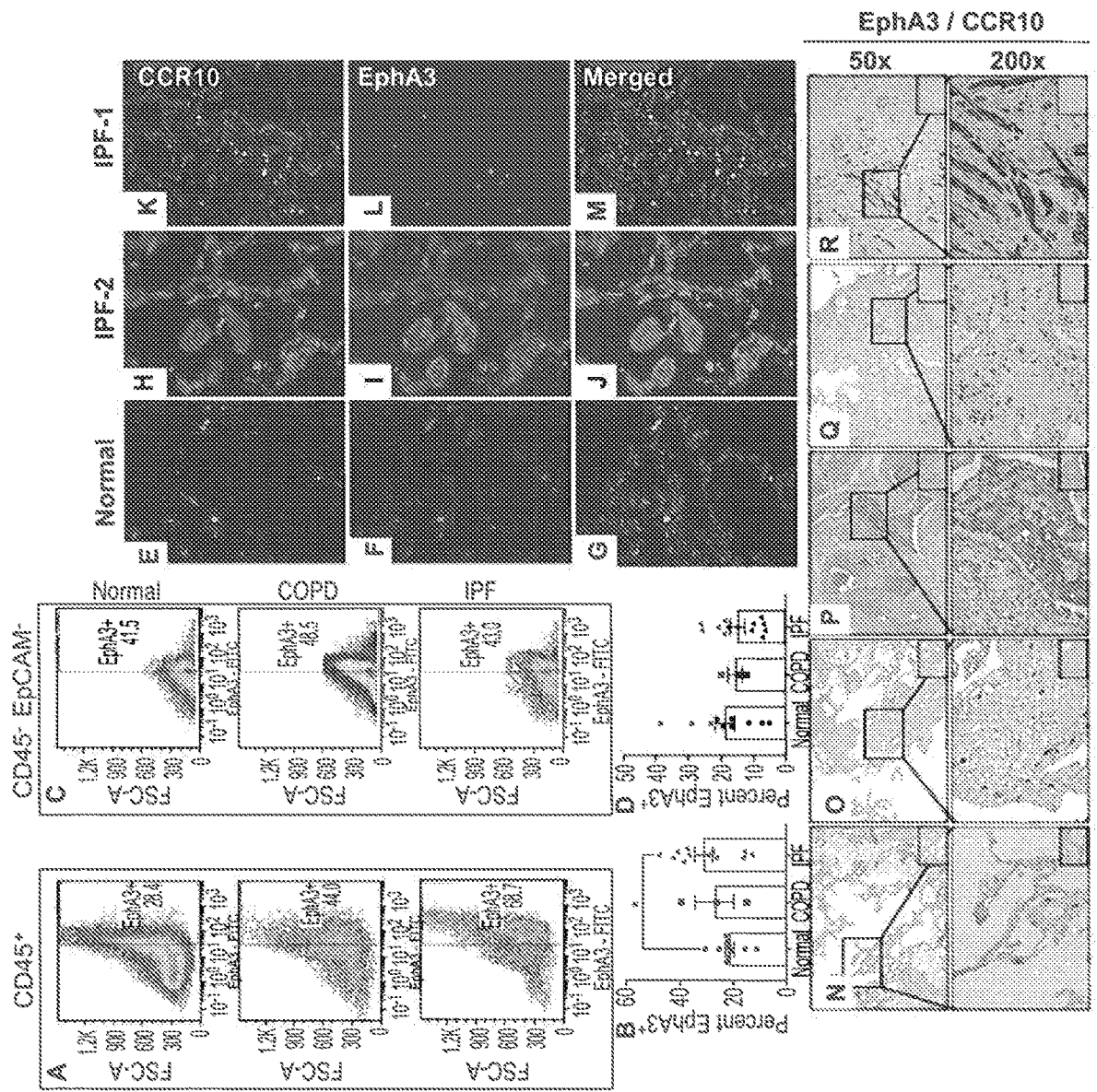
FIG. 28 shows EphA3 expression by $CCR10^+$ cells in normal and IPF lung explants. (A-C) Flow cytometric analysis of mechanically dissociated normal and IPF lung explant cellular suspensions for cell surface CD45, EpCAM and CCR10 proteins. Depicted are representative dot plots (A-C) of EphA3 expressing cells from normal (top), COPD (middle) and IPF (bottom) lung explants. Bar graphs (B & D) depict the average percentage of lineage labeled cells $CCR10^+$ cells expressing EphA3 protein in normal (n=10), COPD (n=3) or IPF (n=13) lung explants. *p≤0.05****p≤0.0001 (E-M) Representative immunofluorescence images showing CCR10 (green; E, H & K), EphA3 (red; F, I & L) and a merged composite (G, J & M) in both normal (E-G) and IPF (H-M) lung explants. n=5-7/group. (N-R) Representative IHC images stained for CCR10 (red) and EphA3 (brown) in normal lung (N), IPF lung biopsies (O-P) and IPF lung explants (Q-R) taken at 50× (top) and 200× (bottom). The respective IgG isotype control staining is shown in the inlayed images. n=5-8/group.

While not wishing to be bound by any particular theory, we believe that the persistence and/or expansion of CCR10⁺ cells in humanized NSG mice might be due, in part, to other tyrosine kinases, particularly those that were not targeted by nintedanib. Accordingly, a custom list of tyrosine kinases that were not listed as targets for BIBF-1120 was generated using Ingenuity IPA. Many of these receptor and non-receptor tyrosine kinases were elevated in both IPF lung biopsies (FIG. 26) and explants (FIG. 27) but EphA3 was consistently the highest in both the biopsies and explants (FIGS. 26-27). Comparing IPF with normal explant cells, a significant elevation in the percentage of EphA3⁺ CD45⁺ CCR10⁻ cells (FIG. 28A-B) without differences in the percentage of EphA3⁺ Lin⁻ CCR10⁺ cells (FIG. 28C-D) was observed. Although CCR10⁺ EphA3⁺ cells were rarely detected in immunofluorescent stained normal lung samples (FIG. 28E-G), these cells were abundant in IPF lung samples (FIG. 28H-M). Finally, dual color IHC analysis showed that CCR10⁺ EphA3⁺ cells were rarely localized in the interstitial areas of normal lung samples (FIG. 28N) but heterogeneous CCR10⁺ EphA3$^{30}$ cells were prominent in IPF samples (FIG. 28O-R). Together, these results demonstrate that CCR10⁺ cells co-express EphA3, and these cells are more abundant in IPF compared with normal human lungs.

Ephrin A Ligands Modulate Collagen Secretion by CCR10⁺ EphA3⁺ Human Lung Fibroblasts.

Figure 5:
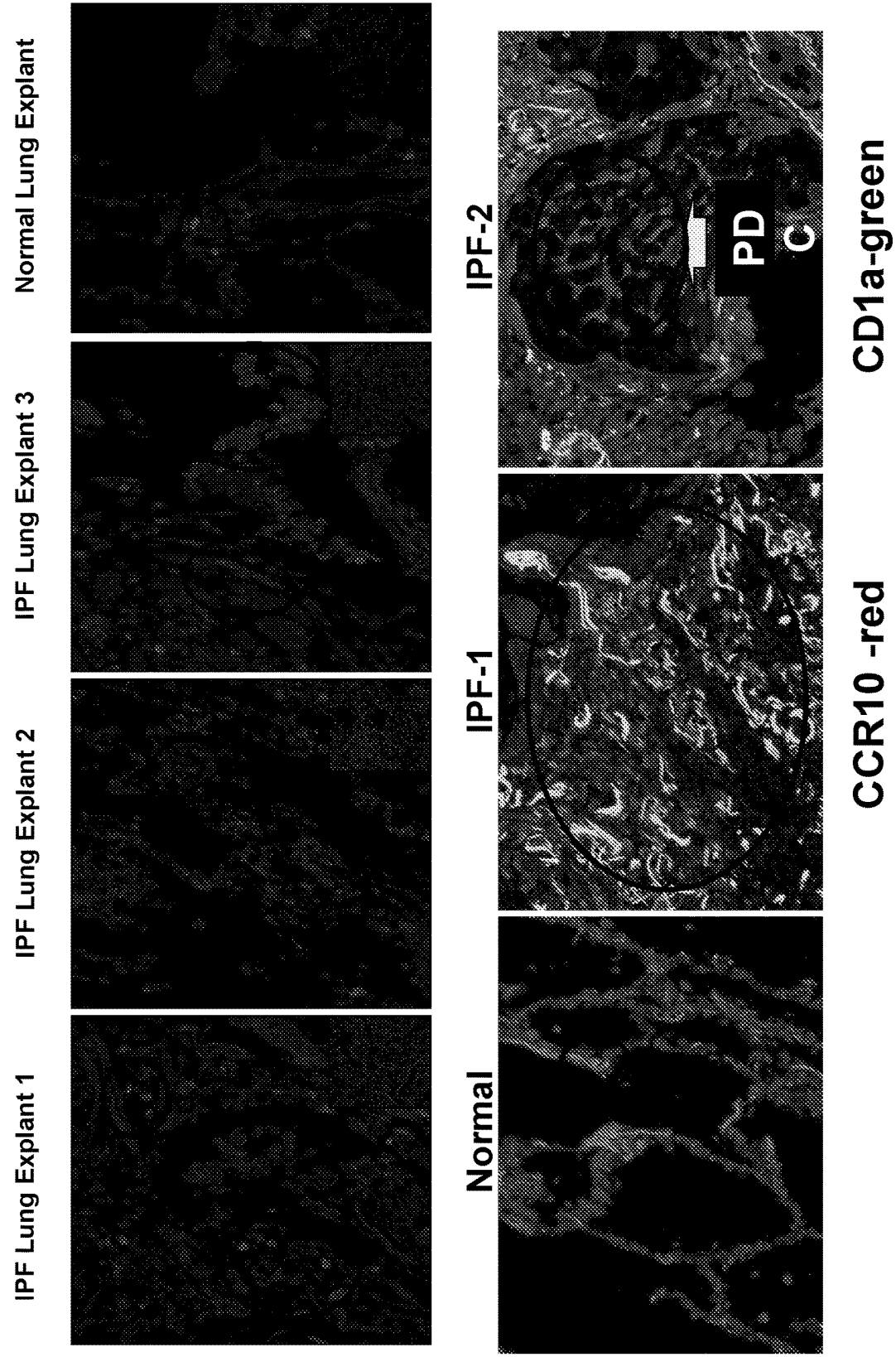
FIG. 5 shows further analysis of CCR10 expression in IPF and normal lung samples, which revealed the presence of another cell, which did not have the elongated appearance of a fibroblast but this other cell was highly positive for CCR10. CCR10 expression was much lower on these cells compared with the strongly positive cells clearly observed in IPF-1.
Figure 6:
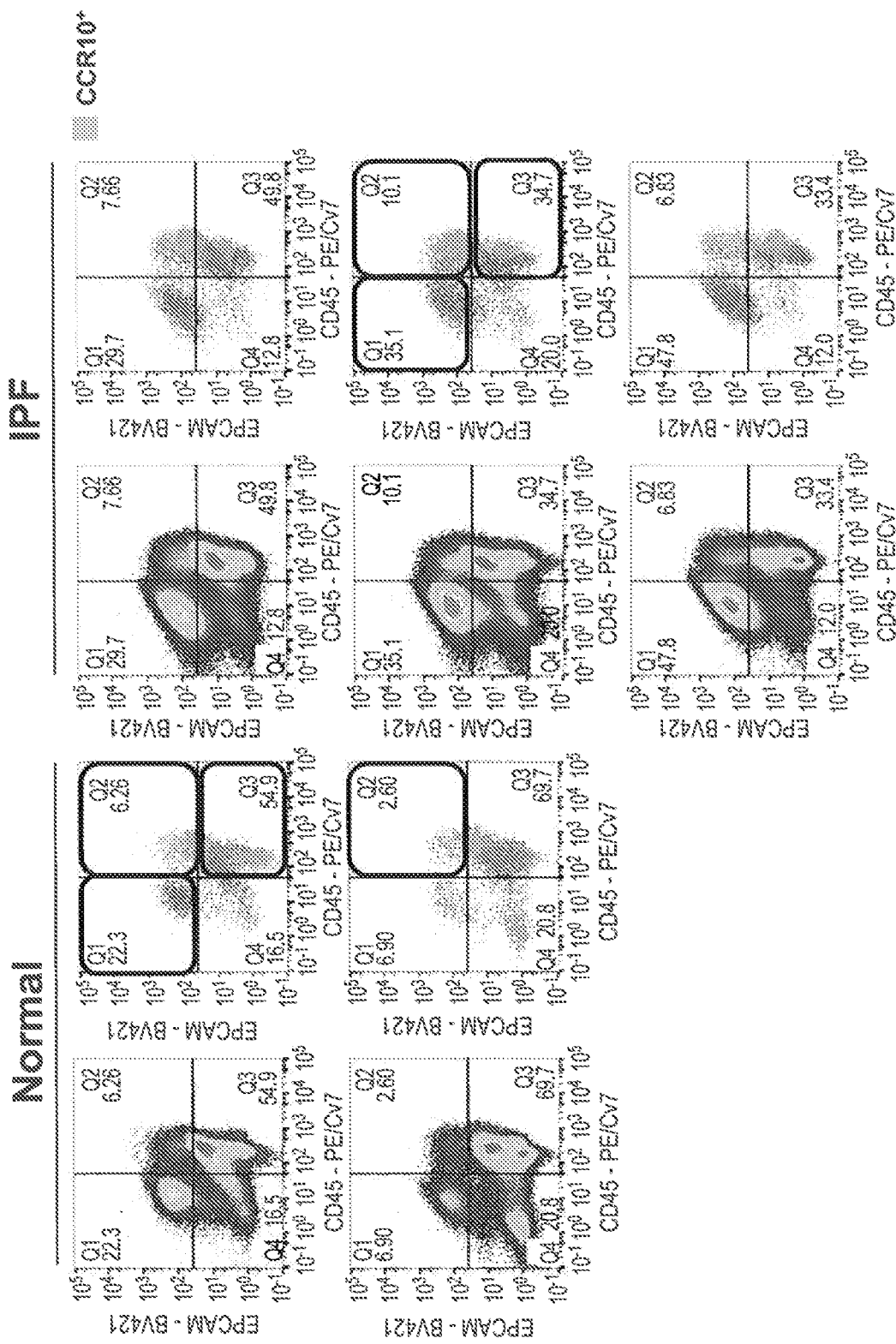
FIG. 6 shows the flow cytometry analysis on various cell populations dissociated from normal donor and IPF explanted lungs.
Figure 7:
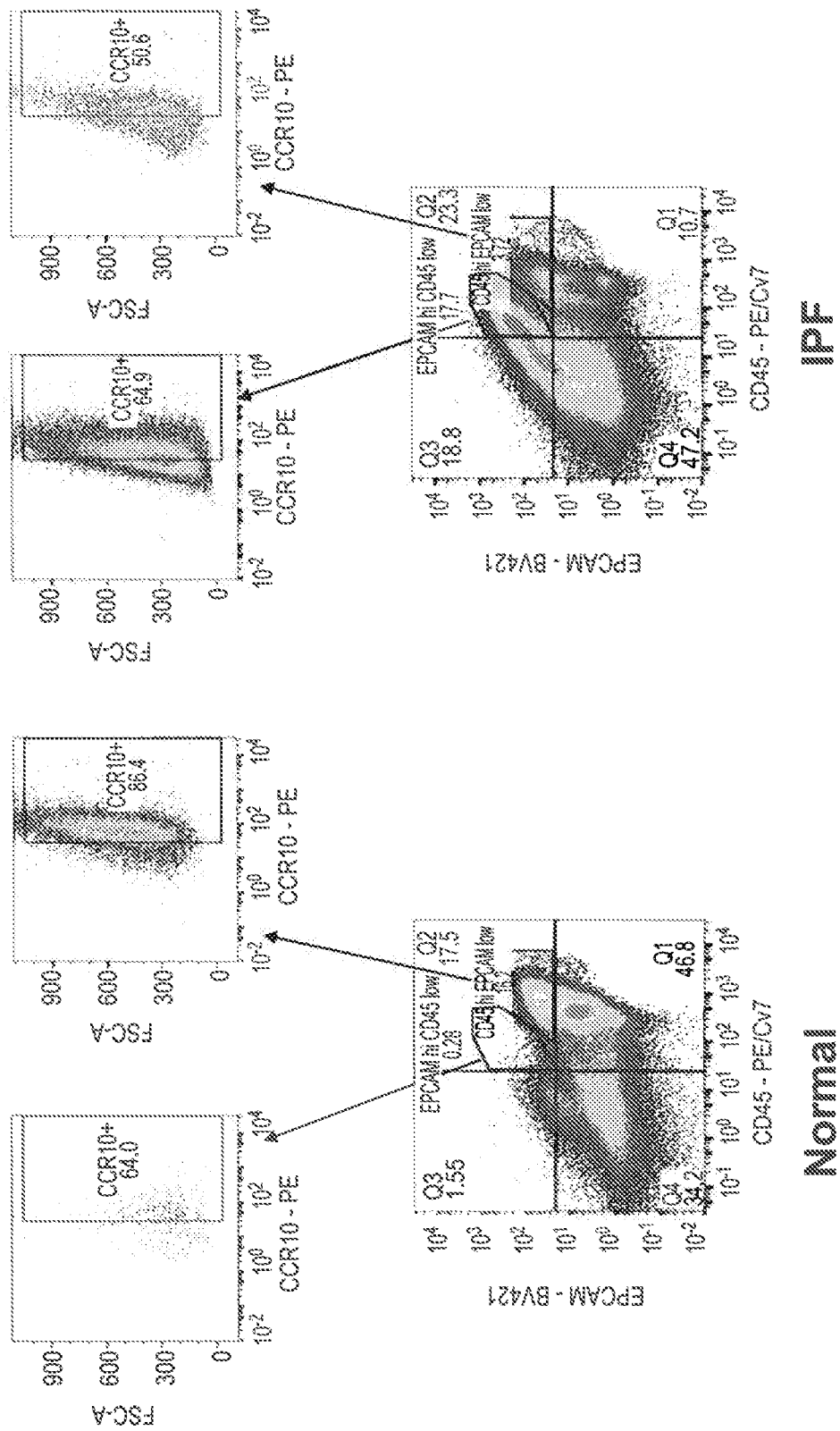
FIG. 7 shows that the CCR10 expression was uniquely localized to a population of cells in IPF, which expressed CD45, EpCAM, and CCR10. Note this population is not present in normal lung but is abundantly expressed in IPF.
Figure 8:
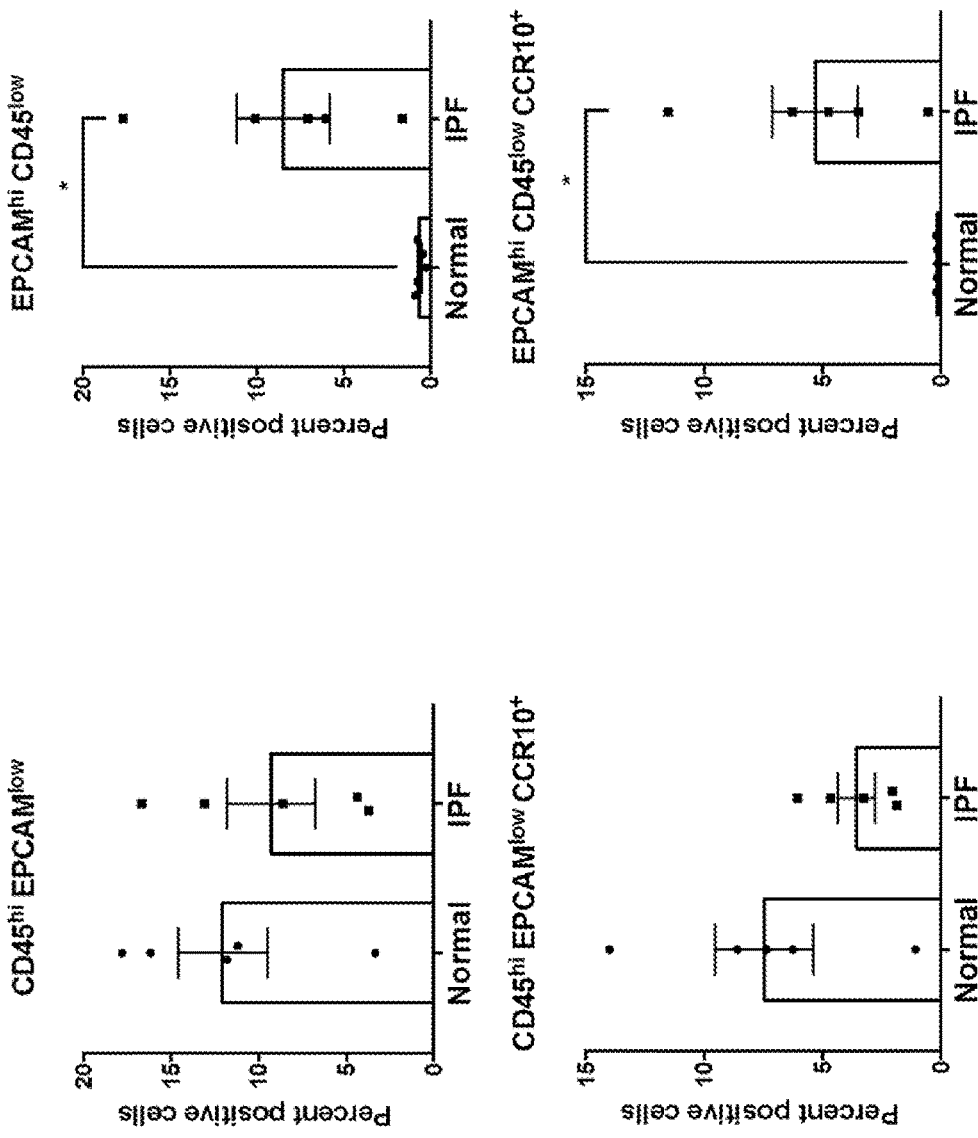
FIG. 8 shows the percentages of the various CD45 and EpCAM double positive cells, and these data clearly highlight the presence of an EpCAM, CD45, CCR10 population in IPF compared with normal lung samples.
Figure 9:
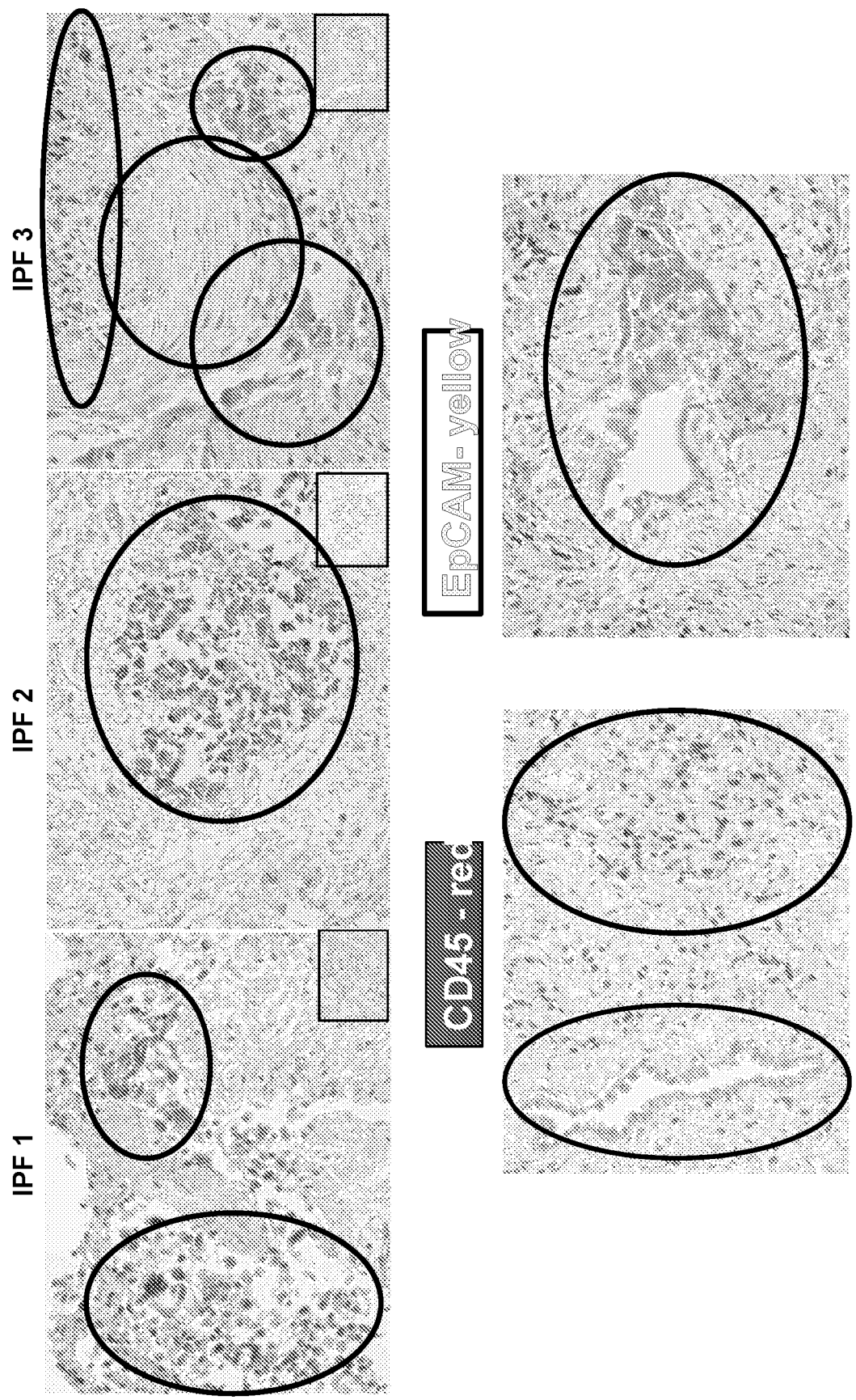
FIG. 9 shows the immunohistochemistry analysis confirming the presence of CD45 and EpCAM expressing cells in IPF lung samples. Double positive cells were observed and these cells were uniquely positioned next to fibroblastic foci (black circle) and in the areas of the lung that are undergoing 'honeycombing' or abnormal remodeling.
Figure 10:
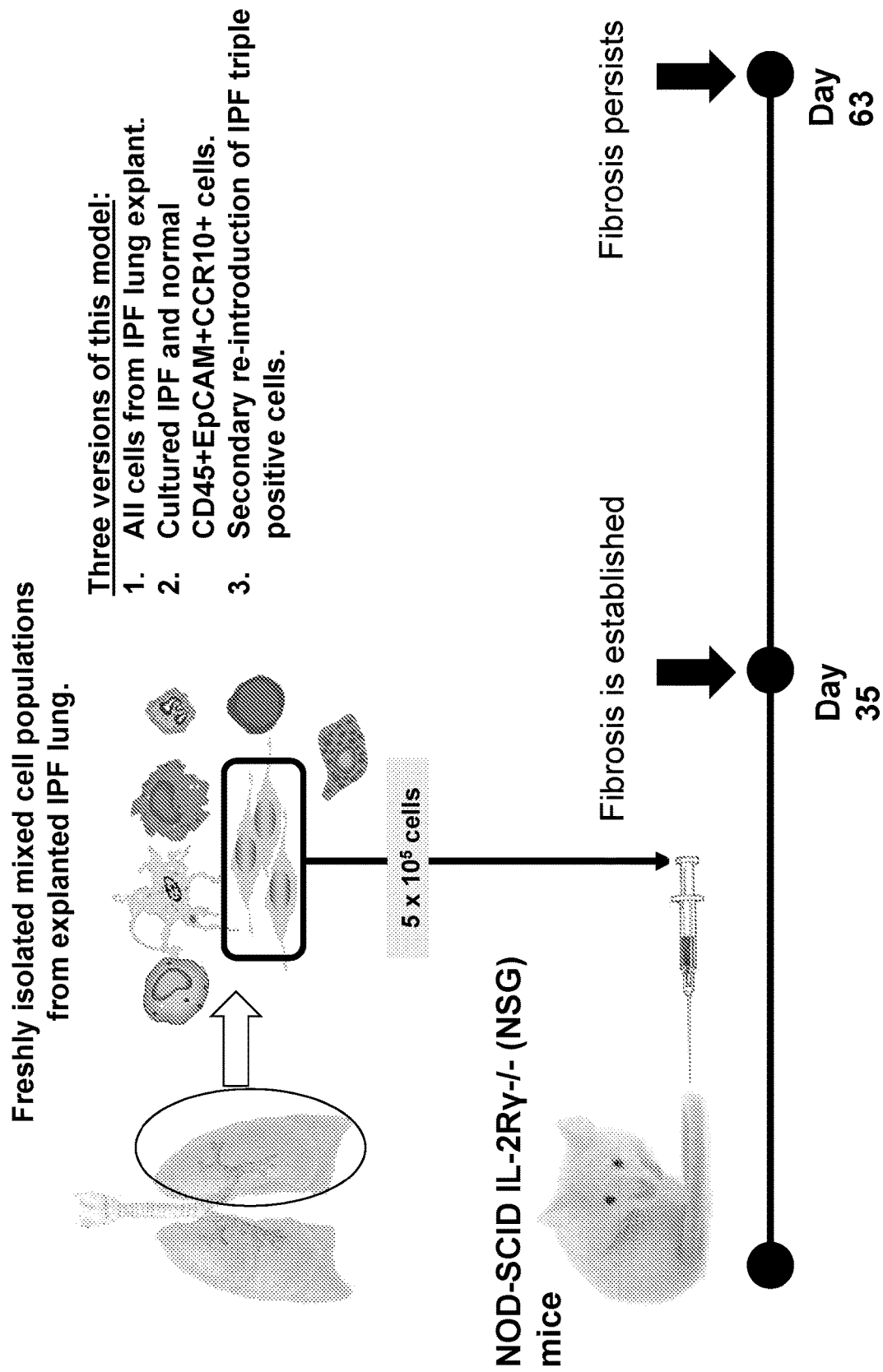
FIG. 10 shows details of a humanized SCID mouse model of IPF and the variations tested in this model.
Figure 11:
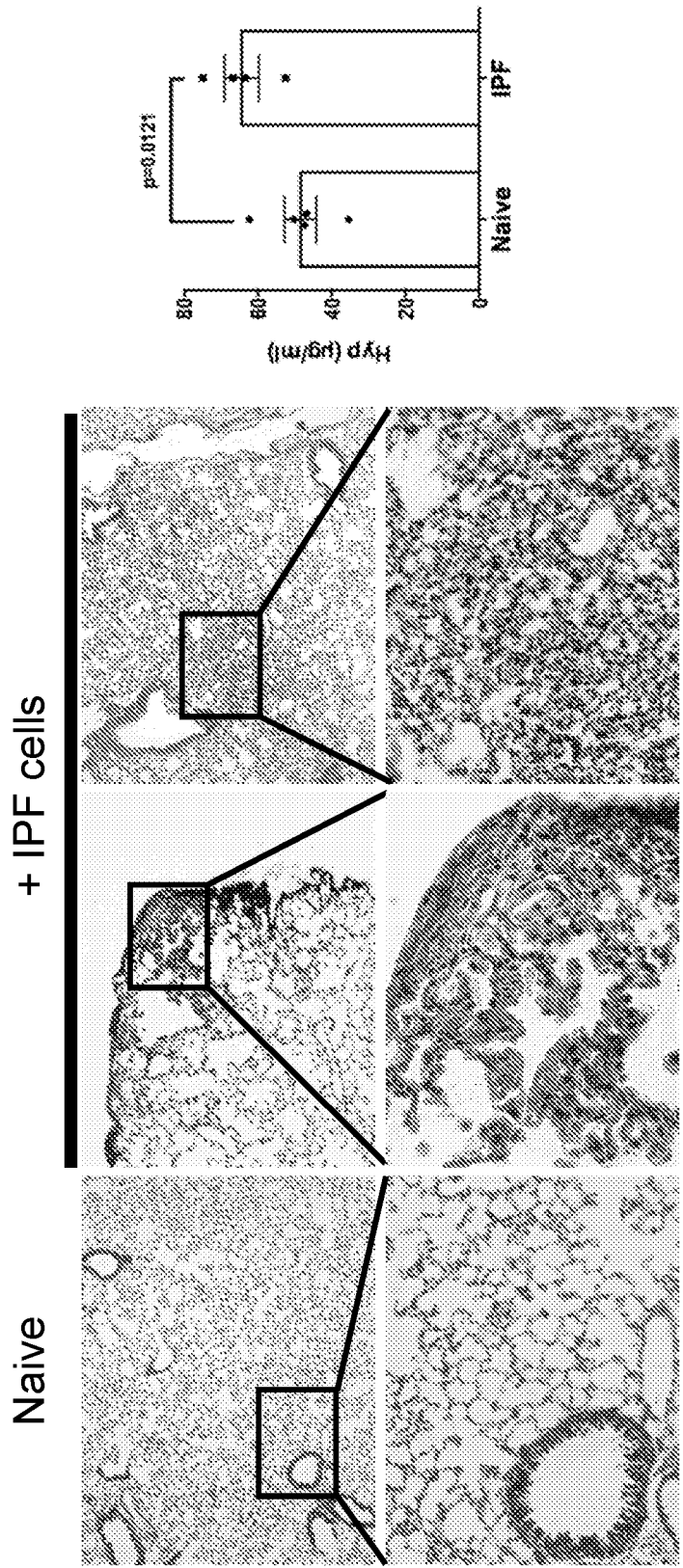
FIG. 11 shows that the infusion of human IPF cells causes lung fibrosis in SCID mice, which is apparent in histological sections and following biochemical analysis of other lung tissue for the presence of hydroxyproline.
Figure 12:
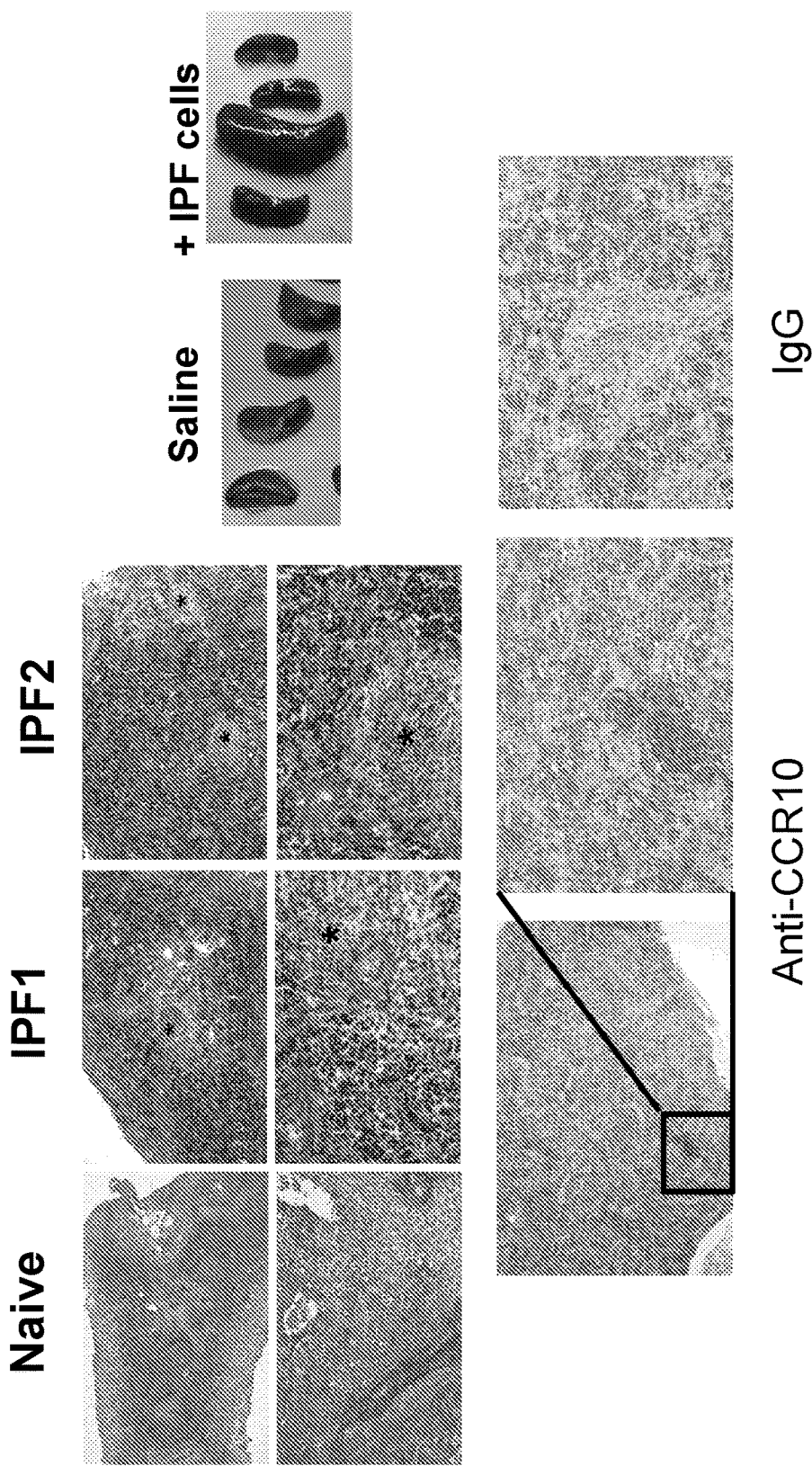
FIG. 12 shows that the CCR10 cells localize to the spleens of SCID mice following the infusion of IPF cells.
Figure 13:
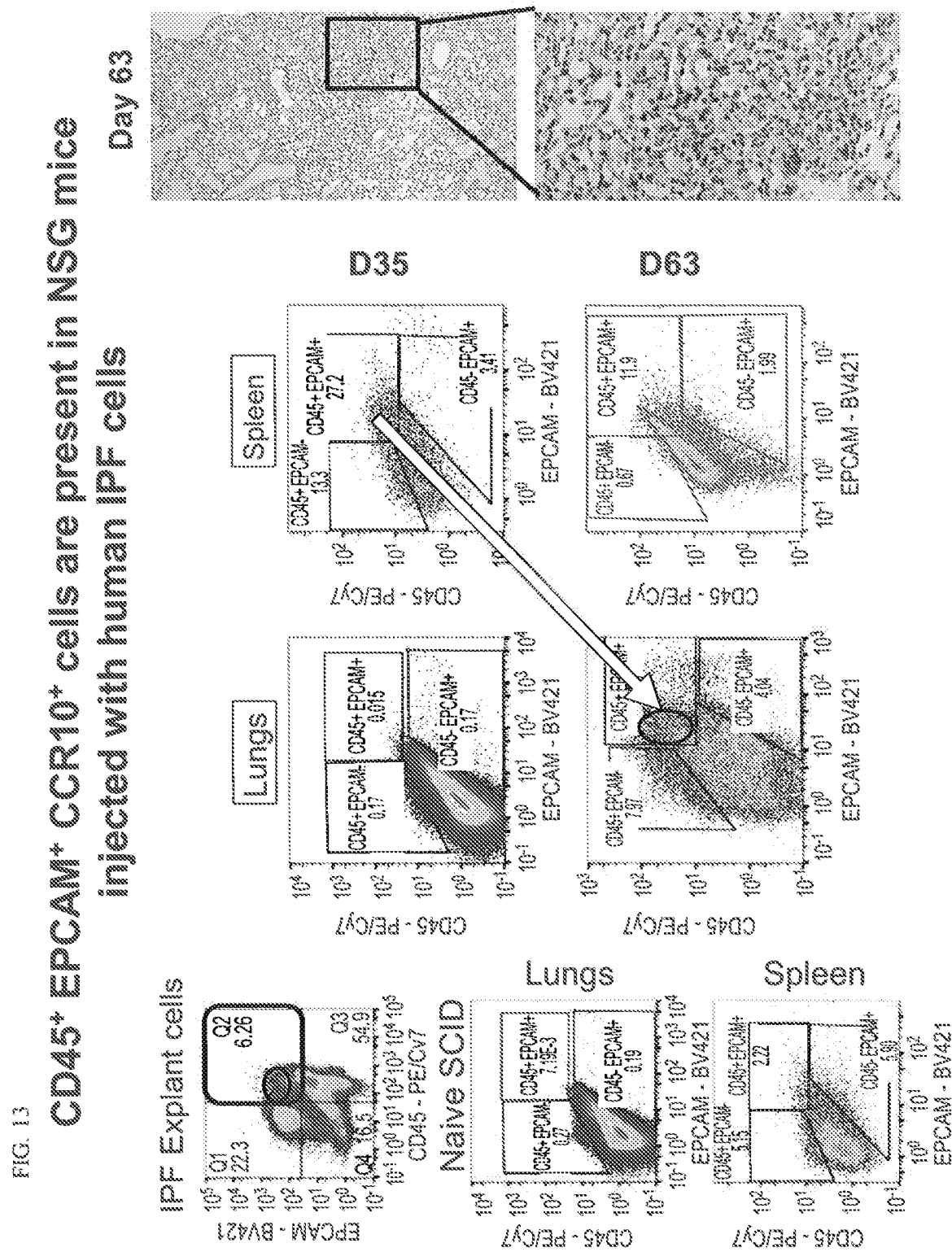
FIG. 13 shows that the triple positive cells are present in the cells infused into SCID mice, these cells are not present in naive SCID mice, and once infused the human triple positive cells localize in the spleen before moving to the lungs of injected SCID mice. The presence of human CCR10 in the lungs of SCID mice receiving human cells 63 days later is also shown.
Figure 14:
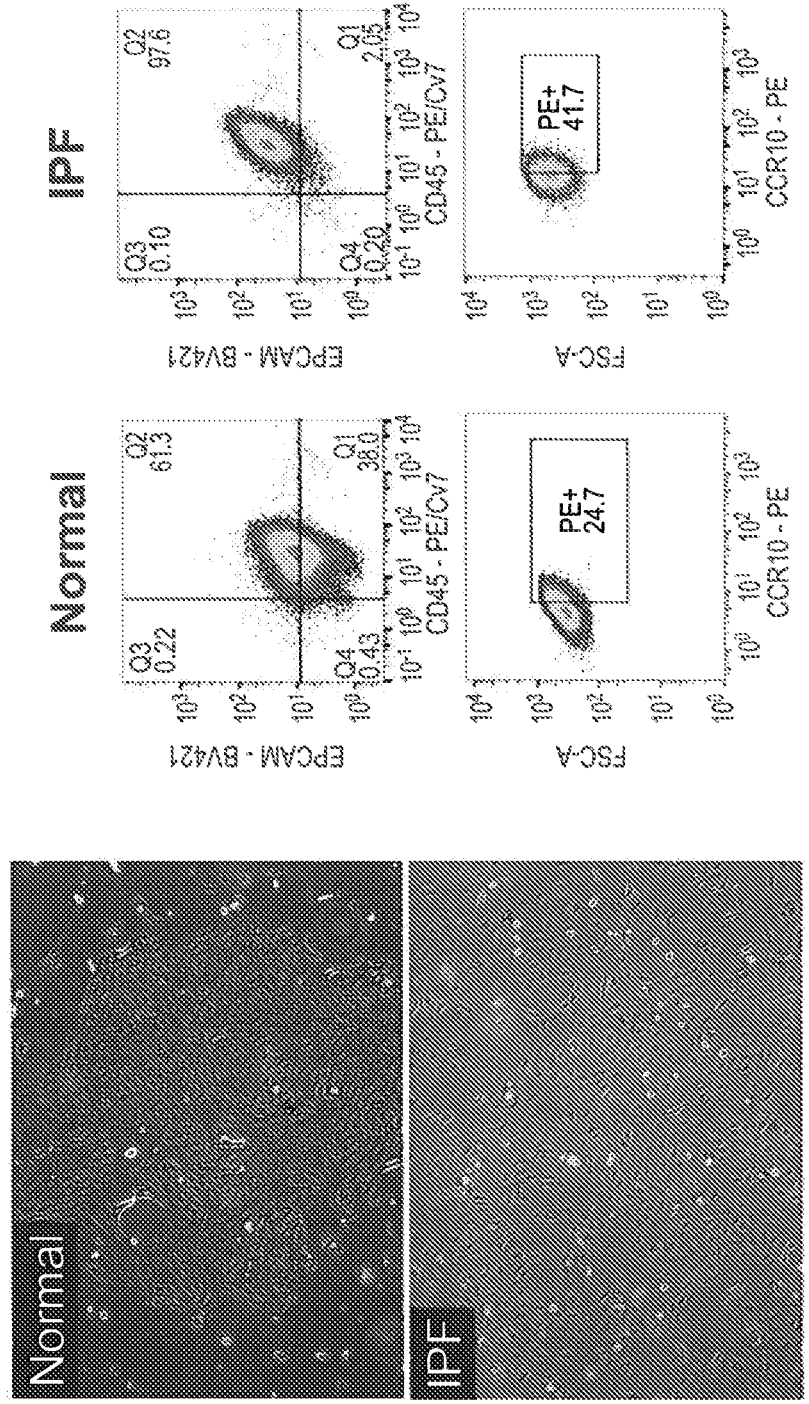
FIG. 14 shows the cell culture technique utilized to expand these to study the triple-positive cells in more detail. This technique was very effective in expanding the triple positive population using both normal and IPF cells.
Figure 15:
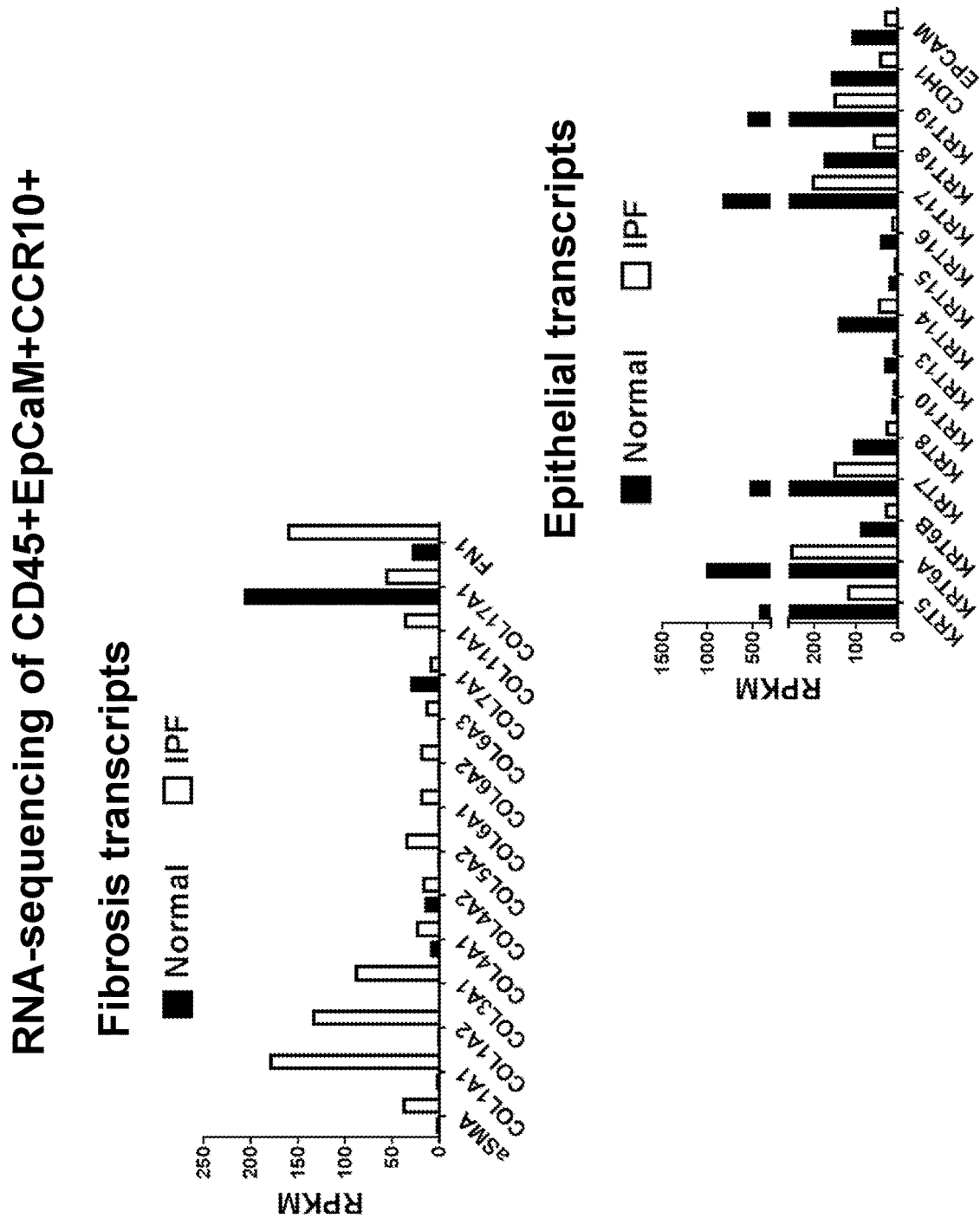
FIG. 15 shows that the IPF cells express much higher levels of fibrosis transcripts while the normal cells have a much stronger epithelial transcript signature.
Figure 16:
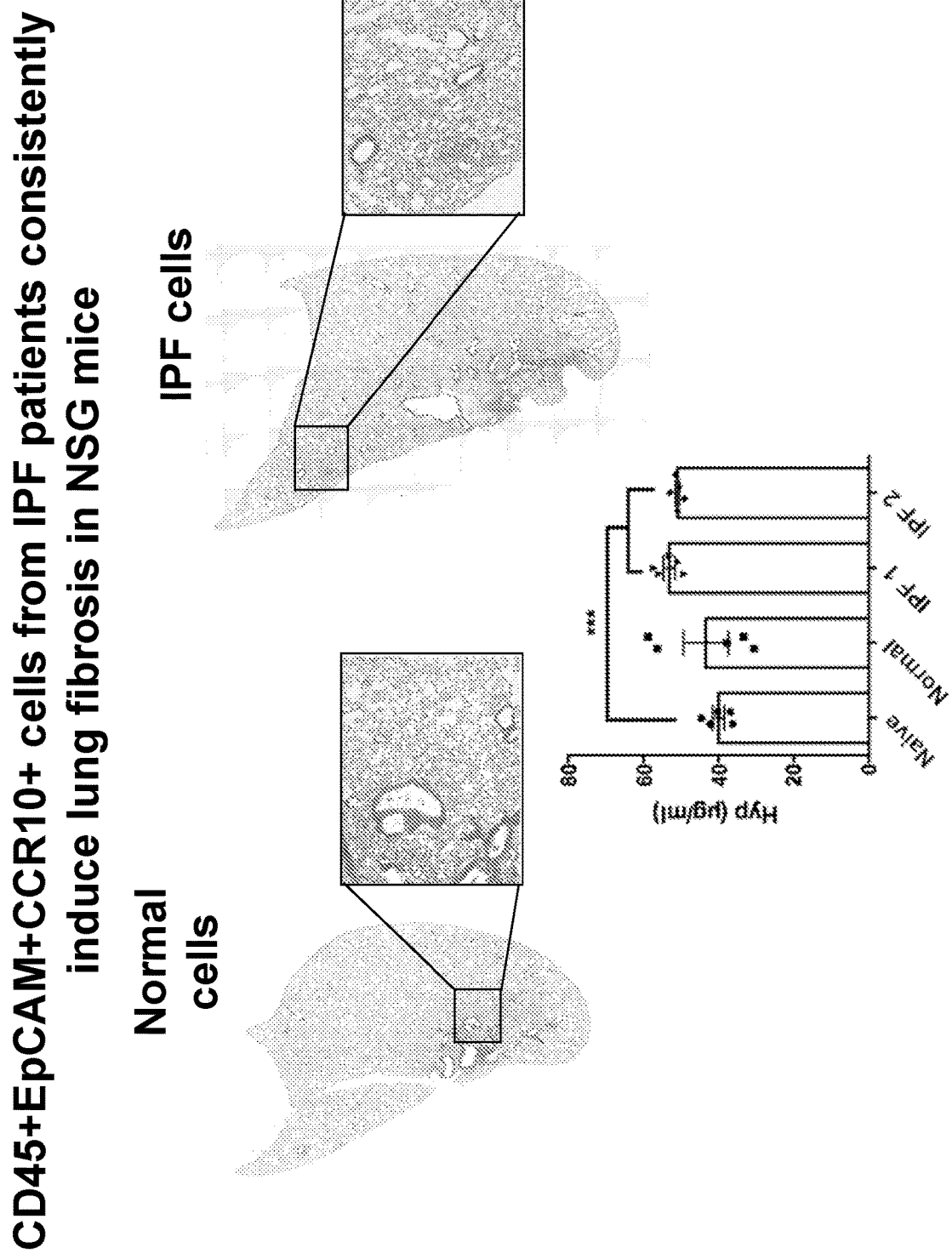
FIG. 16 shows that the infusion of IPF but not normal CD45, EpCAM, and CCR10 cells into SCID mice induced pulmonary fibrosis as shown histologically and via the hydroxyproline assay.
Figure 17:
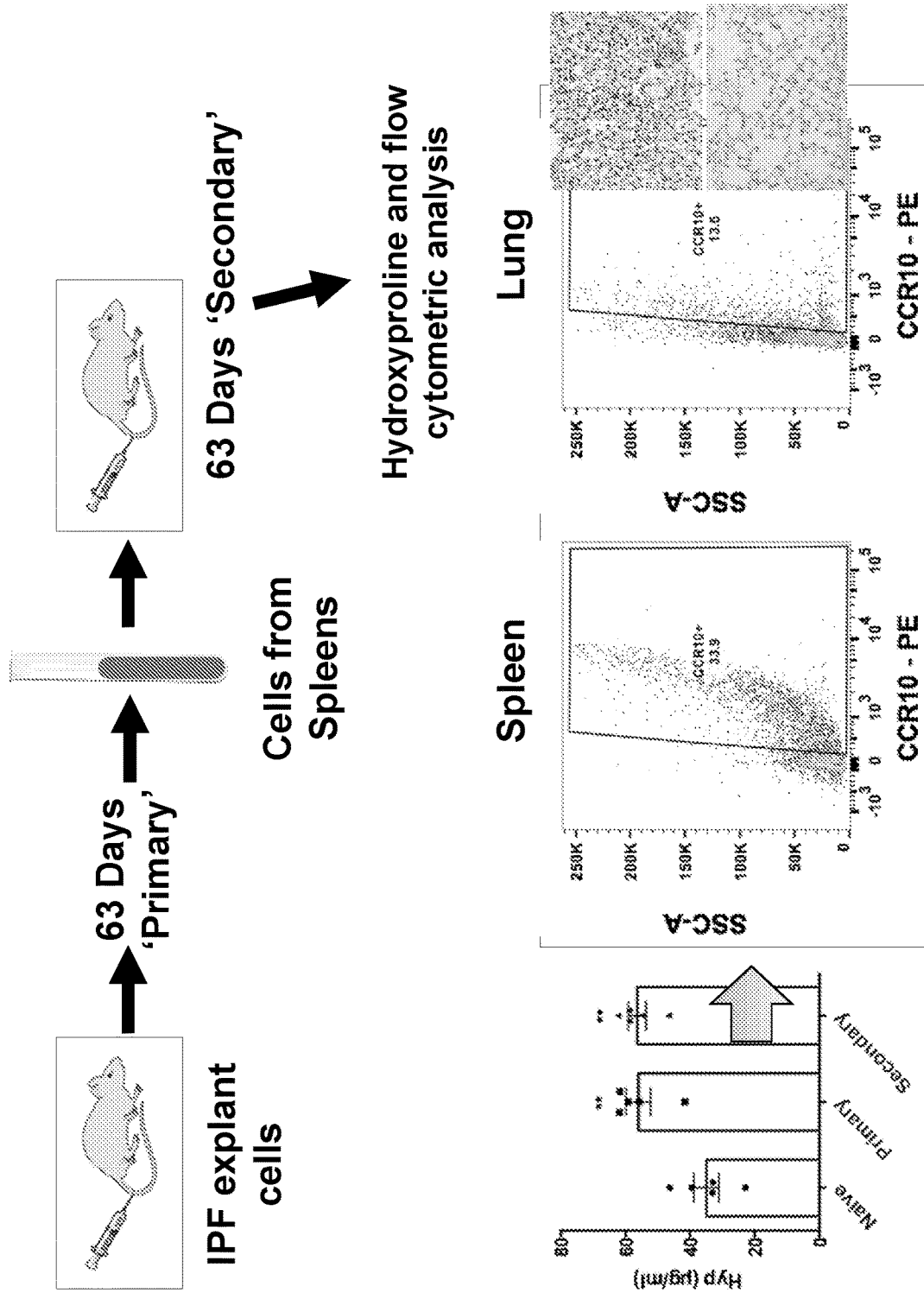
FIG. 17 shows the third SCID study, which provides yet further proof that the triple positive cell is both pro-fibrotic and disease transferring. In this 3rd study, IPF explant cells were introduced and 63 days later CCR10-expressing cells from the spleens of these mice were isolated. These human cells from mouse spleen were then introduced into a. second group of SCID mice and 63 days later, these mice were examined for the presence of pulmonary fibrosis. There was both biochemical and histological evidence of pulmonary fibrosis in the secondary model, and the predominant cell type was the human CCR10-expressing cell both in spleen and lung from this secondary group.
Figure 29:
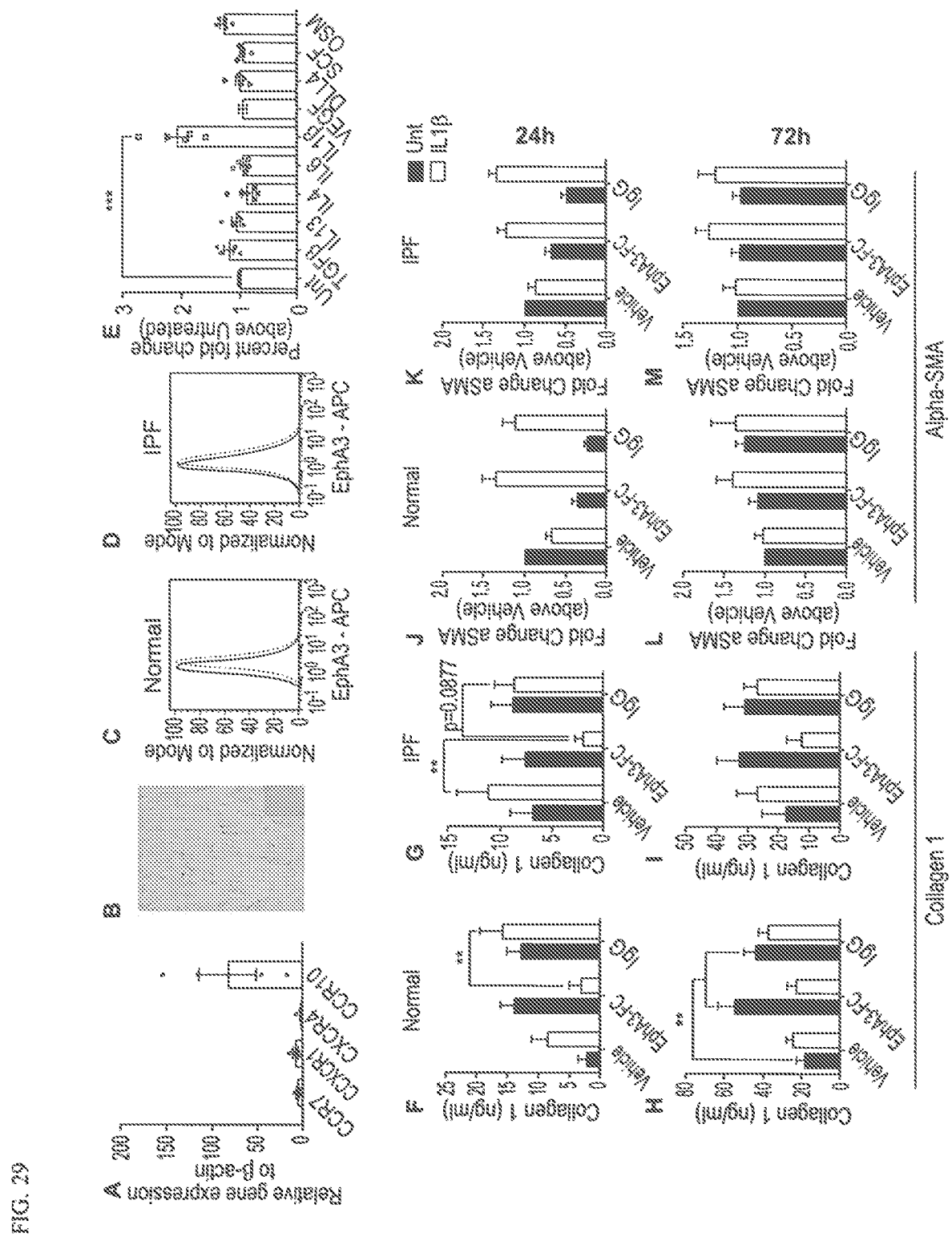
FIG. 29 shows Ephrin A ligand neutralization significantly reduces soluble collagen production by normal and IPF lung fibroblasts. (A) qPCR analysis for CCR7, CCXCR1, CXCR4, and CCR10 transcripts was performed on IPF lung fibroblasts. The average expression of the chemokine receptors relative to β-actin is shown. Data are mean±s.e.m.; n=4 fibroblast lines. (B) Normal and IPF lung fibroblasts were fixed and stained with an anti-EphA3 antibody. Representative images of EphA3 staining (brown) in IPF lung fibroblasts (inlay=isotype control antibody). Lung fibroblasts were exposed to various factors for 24 h followed by flow cytometry for surface EphA3 expression. (C-D) Representative histograms of untreated (dark grey) and IL1β-treated (light grey) normal (C) and IPF (D) lung fibroblasts stained with anti-EphA3 antibodies. (E) The fold change in surface EphA3 GMFI in treated compared with untreated fibroblasts. Data are mean±s.e.m., n=4-5 fibroblast lines/group. Normal and IPF lung fibroblasts were exposed to vehicle or IL1β with either EphA3-Fc or IgG control antibodies. At both 24 and 72 h, conditioned supernatants were collected and the cells were analyzed for αSMA content. (F-I) Soluble collagen 1 generated by normal (F & H) and IPF (G & I) lung fibroblasts at 24 (F-G) and 72 (H-I) h after the addition of IL1β or vehicle and/or EphA3-Fc or IgG. (J-M) Fibroblasts were permeabilized and an in-cell ELISA for αSMA and β-tubulin proteins were used. Alpha-SMA levels were normalized to β-tubulin levels and fold changes were calculated. Depicted is the average fold change of αSMA protein expression in normal (J & K) and IPF (L & M) lung fibroblasts, 24 (J-K) and 72 (L-M) h after IL1β or vehicle stimulation and/or EphA3-Fc or IgG treatment. Data shown are mean±s.e.m.; n=4-5 fibroblast lines/group.

Because IPF samples contained CCR10⁺ EphA3⁺ Lin⁻ cells (FIGS. 28C-D & 28R), we next determined the effects of CCR10 and EphA3 ligands in lung fibroblast activation. CCR10 was expressed amongst the greatest other chemokine receptors including CCR7, CCXCR1, and CXCR4 on IPF lung fibroblasts (FIG. 29A). However, the CCR10 ligand, CCL28, did not consistently modulate lung fibroblast invasiveness, collagen 1 secretion, or αSMA protein expression (not shown). Given that EphA3 was localized intracellularly in cultured CCR10⁺ human lung fibroblasts (FIG. 29B), studies were undertaken to identify factors that promoted surface localization of EphA3. Twenty-four hours after stimulation, only IL1β (20 ng/ml) significantly unregulated surface EphA3 on both normal and IPF lung fibroblasts (FIG. 29C-D and quantified in 29E). IL1β induced collagen 1 (FIG. 29F-I) but not intracellular αSMA protein in normal and IPF lung fibroblasts after 24 (FIGS. 29F-G & 29J-K, respectively) and, to a lesser extent, 72 h (FIGS. 29H-I & L-M, respectively). Further, neutralizing Ephrin A ligands using EphA3-FC in the presence of IL-1β significantly reduced collagen 1 secretion by IPF (FIG. 29G) but not by normal (FIG. 29F) lung fibroblasts at 24 h. At 72 h, EphA3-FC reduced soluble collagen 1 in IPF but not normal lung fibroblast cultures (FIGS. 5I and 5H respectively). Finally, EphA3-FC alone did not alter collagen 1 (FIG. 29F-I) or αSMA (FIG. 29J-M) compared with IgG-treated cells. Together, these results demonstrated that IL1β-induced the surface EphA3 expression and Ephrin A ligands promoted IL1β-induced collagen 1 secretion by primary CCR10⁺ human lung fibroblasts.

Targeting CCR10⁺ EphA3⁺ Cells Ameliorated Lung Fibrosis in NSG Mice.

Figure 30:
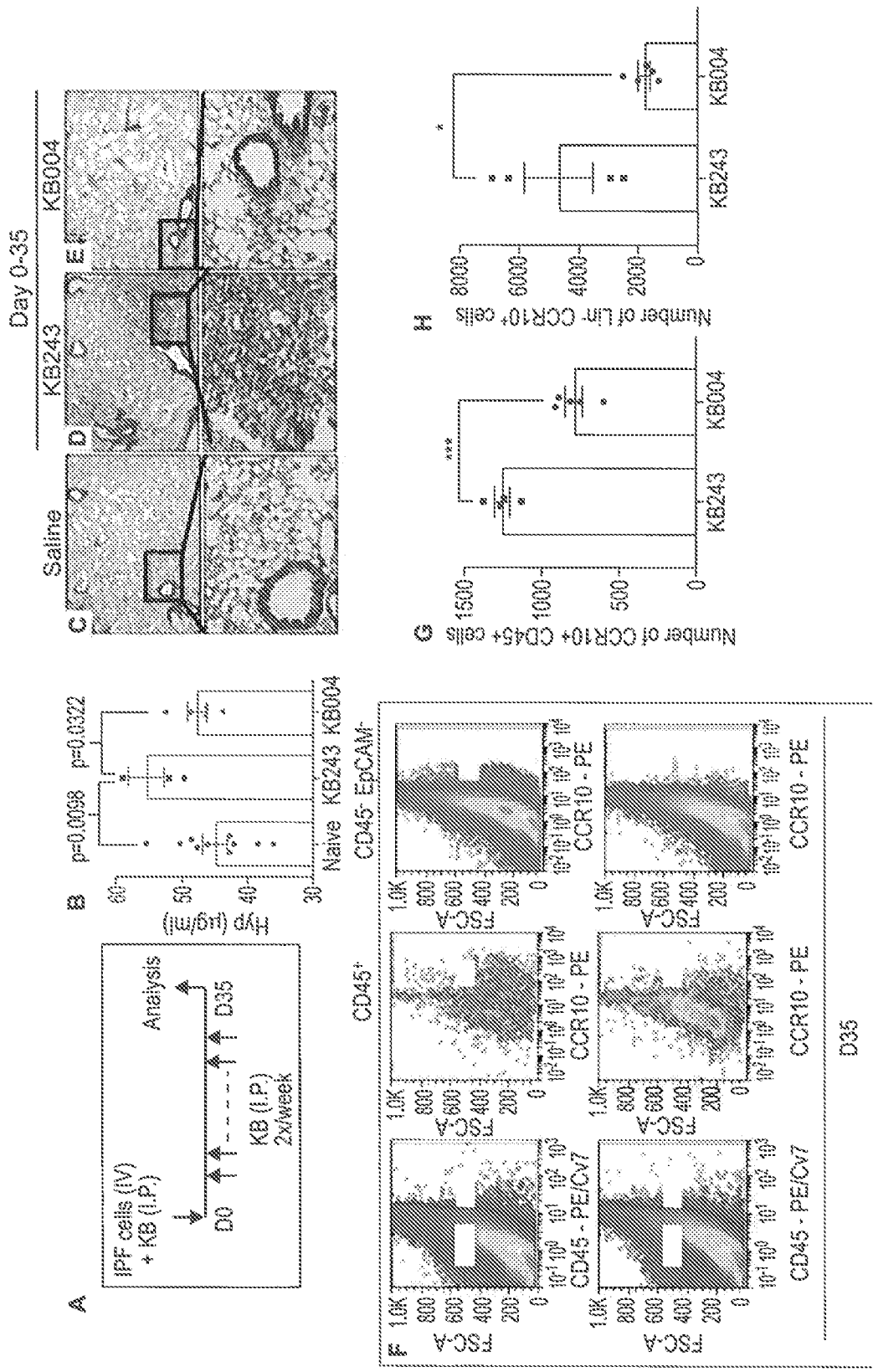
FIG. 30 shows targeting of $CCR10^+$ $EphA32^+$ cells prevented the development of fibrosis in humanized NSG mice. (A) Experimental scheme. (B) Hydroxyproline in non-humanized NSG mice and humanized NSG mice that received either KB243 or KB004. Data shown are mean±s.e.m.; n=4-5/group; p values indicated. (C-E) Representative images of Masson's trichrome staining of lungs from non-humanized mouse lung (C), and humanized NSG mice at day 35 after IPF cell injection and treatment with either KB243 (D) or KB004 (E). Shown are images taken at 50× (top) and 200× (bottom) magnification. (F) Human $CD45^+$, $CD45^+$ $CCR10^+$ and $Lin^-$ $CCR10^+$ cells in NSG mouse lungs at day 35 after IPF cell injection and mAb treatment. n=4-5/group. (G-H) Human $CD45^+$ $CCR10^+$ (G) and $Lin^-$ $CCR10^+$ (H) cells in NSG mice at day 35 after IPF cell injection and mAb treatment. Data shown are mean±s.e.m.; n=4-5/group, *p≤0.05 ***p≤0.001.
Figure 31:
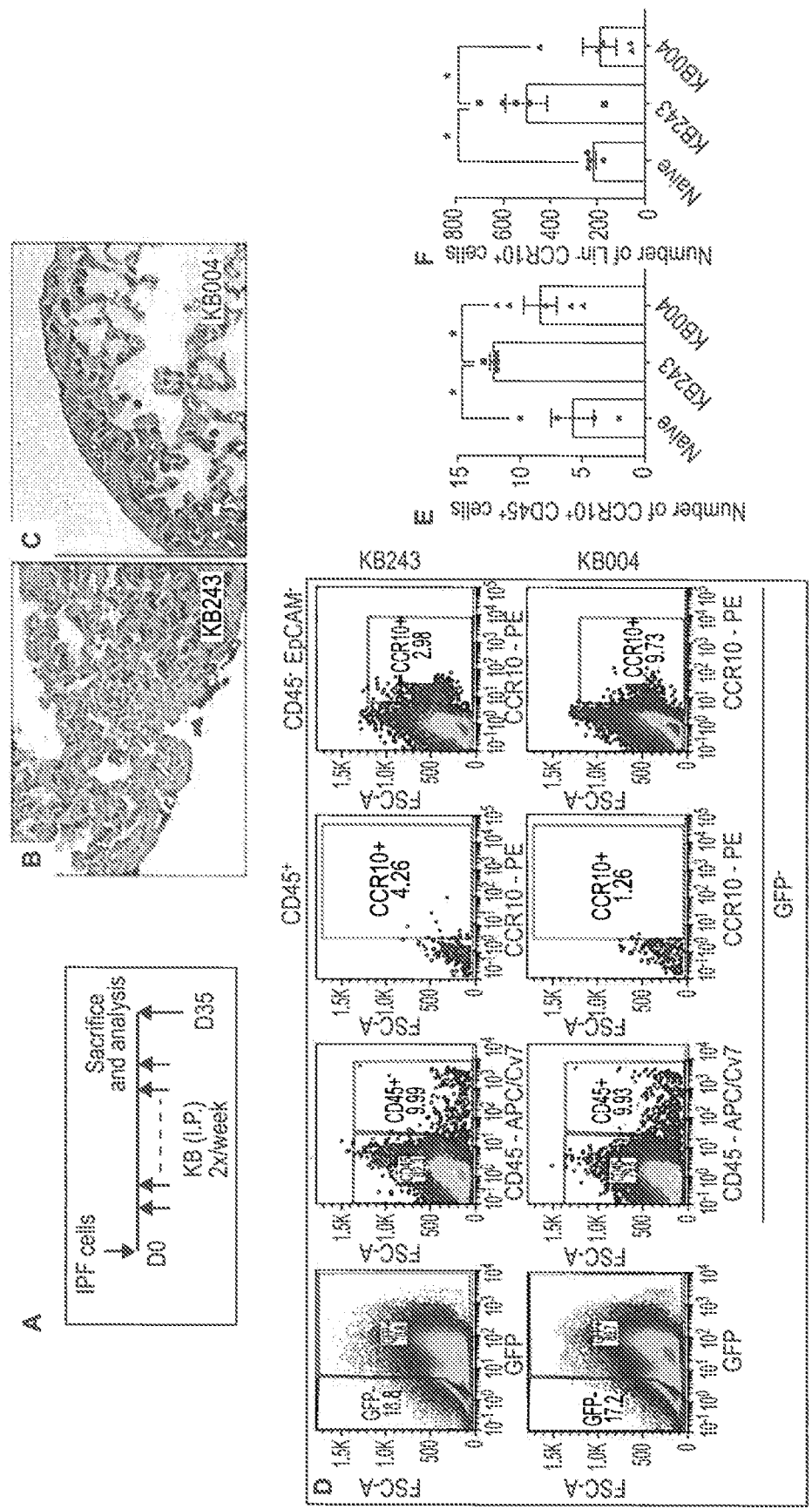
FIG. 31 shows KB004 antibody treatment significantly reduced $CCR10^+$ cells in lung and spleen of humanized. NSG-GFP mice. (A) IPF cells were injected intravenously into NSG-GFP mice, and 2 hours later groups of mice received either 5 mg/kg of KB004 (an afucosylated anti-EphA3 mAb) or KB243 (an isotype control) via intraperitoneal injection. Both groups of mice were injected twice a week with the antibodies for 5 weeks after which lungs and spleen were collected for histological and/or flow cytometric analysis. (B-C) Depicted are representative images of GFP-stained NSG mouse lung (red indicates the presence of transgenic GFP mouse cells) at day 35 after IPF lung injection in both the KB243 (B) and KB004 (C) treatment groups. (D) Flow cytometric dot plots depicting $GFP^-$ staining for human-CD45, CCR10 and/or EpCAM proteins. Representative dot plots for (from left to right) $GFP^-$ cells expressing CD45, CD45, and CCR10 or CCR10 alone in humanized NSG-GFP mice treated either with KB243 (top) or KB004 (bottom) antibodies are shown. (E-F) The average number of $GFP^-$ $CD45^+$ $CCR10^+$ (E) and $GFP^-$ $Lin^-$ $CCR10^+$ (F) cells in non-humanized and humanized NSG mice treated with either KB243 or KB004. Data shown are mean±sem n=4-5/group. *p≤0.05

To address the profibrotic effects of CCR10⁺ EphA3⁺ cells in vivo, humanized NSG mice were prophylactically treated with 5 mg/kg of either anti-EphA3 (KB004) or IgG isotype control (KB243) mAbs as shown in FIG. 30A. Hydroxyproline was significantly increased in the lungs of humanized NSG mice treated with KB243; however, KB004 treatment significantly reduced hydroxyproline to levels observed in non-humanized NSG lungs (FIG. 30B). There was interstitial remodeling and collagen staining observed in the KB243-treated group (FIG. 30D) but not in the KB004-treated group (FIG. 30E), which appeared similar to lung samples from non-humanized mice (FIG. 30C). A significant reduction in CCR10⁺ CD45⁺ and CCR10⁺ Lin⁻ cells was observed in the KB004—(FIG. 30F, bottom) versus the KB243-treated groups (FIG. 30F, top, quantified in FIG. 30G-H). To confirm human cell targeting, antibody treatment was stated immediately prior to humanization of NSG-GFP mice (FIG. 31A). IHC analysis for GFP cells at day 35 after IPF cell injection showed fewer GFP cells in KB004—(FIG. 31C) compared with KB243—(FIG. 31B) treated humanized NSG-GFP mice. Also, KB004 treatment significantly reduced the number of CD45⁺ CCR10⁺ and Lin⁻ CCR10⁺cells compared with the KB243 treatment group (FIG. 31O, bottom vs top rows; quantified in 31E-F).

Figure 32:
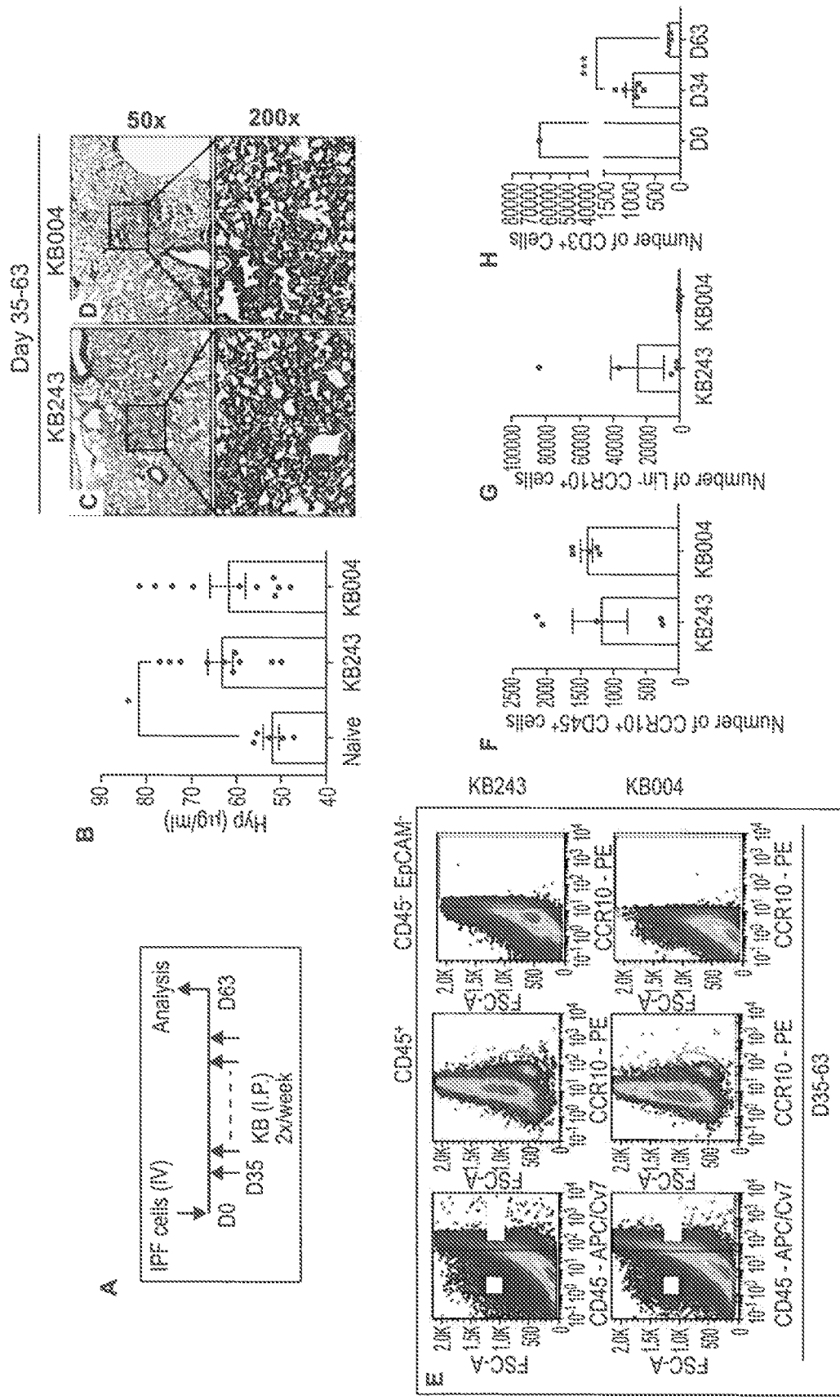
FIG. 32 shows therapeutic administration of KB004 did not reduce established pulmonary fibrosis in humanized NSG mice. (A) Experimental scheme. (B) Hydroxyproline in lungs from humanized NSG mice treated with either KB243 or KB004 mAbs. n=10/group (C-D) Representative images of Masson's trichrome staining of humanized NSG mouse lung at day 63 after IPF cell injection and treatment with either KB243 (C) or KB004 (D). Shown are images taken at 50× (top) and 200× (bottom) magnification. (E) Human CD45$^+$, CD45$^{30}$ CCR10$^+$ and Lin$^-$ CCR10$^+$ cells in NSG mouse lungs at day 63 after IPF cell injection and treatment with either KB243 or KB004; n=4-5/group. (F-G) Human CD45$^+$ CCR10$^+$ (F) and Lin$^-$ CCR10$^+$ (G) cells in NSG mice at day 63 after IPF cell injection and treatment with either KB243 or KB004. Data shown are mean±sem; n=4-5/group. p 0.05 ***p≤0.001. (I) CD3$^+$ cell counts in IPF cell preparations prior to intravenous injection (i.e. Day 0) and in NSG lungs at days 34 and 63 after IPF cell injection into NSG mice. Data shown are mean±sem; n=4-5/group; *p 0.05 ***p≤0.001.
Figure 33:
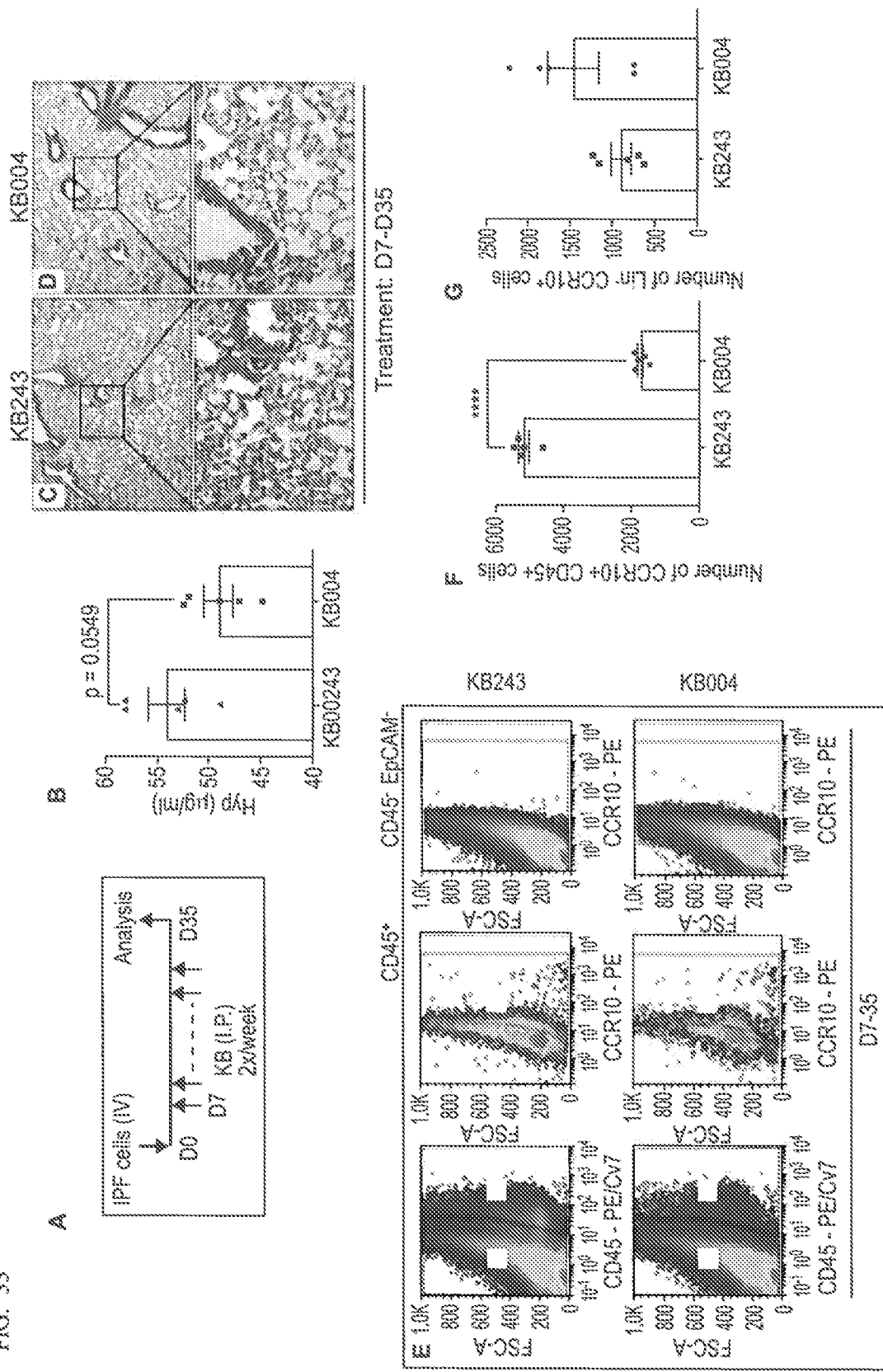
FIG. 33 shows early administration of KB004 reduced lung remodeling in humanized NSG mice. (A) Experimental scheme. (B) Hydroxyproline in lungs from humanized NSG mice treated with either KB243 or KB004 mAbs. n=5/group (C-D) Representative images of Masson's trichrome staining of humanized NSG mouse lung at day 35 after IPF cell injection and treatment with either KB243 (C) or KB004 (D). Shown are images taken at 50× (top) and 200× (bottom) magnification. (E) Human CD45$^+$, CD45$^+$ CCR10$^+$ and Lin$^-$ CCR10$^+$ cells in NSG mouse lungs at day 35 after IPF cell injection and treatment with either KB243 or KB004; n=4-5/group. (F-G) Human CD45$^+$ CC10$^+$ (F) and Lin$^-$ CCR10$^+$ (G) cells in NSG mice at day 35 after IPF cell injection and treatment with either KB243 or KB004. Data shown are mean±sem; n=4-5/group. ****p≤0.0001
Figure 34:
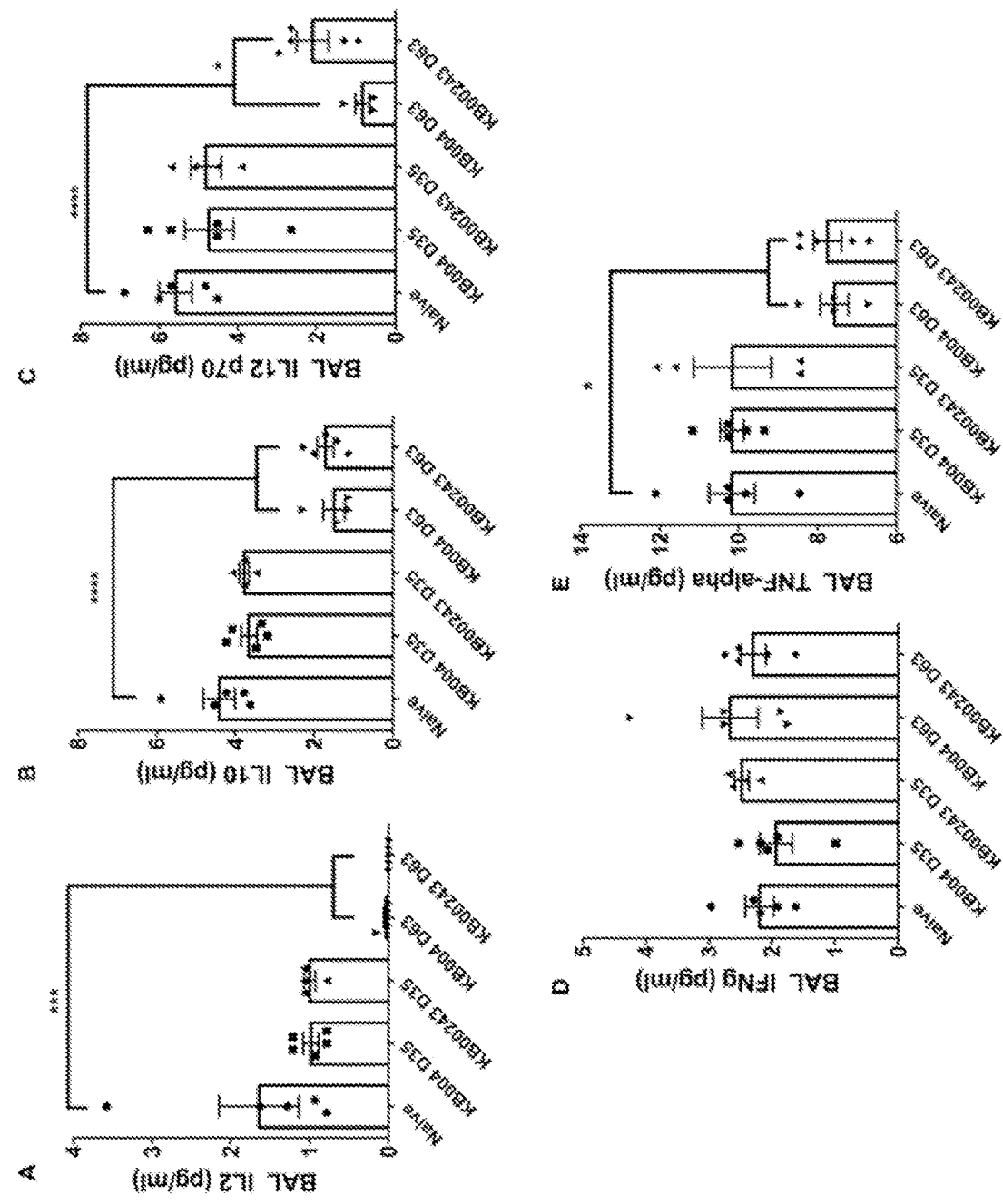
FIG. 34 shows that IPF lung cells did not promote inflammation in the NSG mouse. (A-E) Murine IL-2 (A), IL-10 (B), IL12-p70 (C), IFNγ, and TNFα in the BAL from non-humanized and humanized NSG mice treated with KB004 or KB243 from days 0 to 35, or from days 35 to 63 after IPF cell injection. Mouse cytokines were measured using Bioplex and data shown are mean±sem; n=5-10/group. ****p≤0.0001

To address the therapeutic effects of KB004, separate groups of NSG mice were treated with either KB243 or KB004 starting at day 35 after IPF cell administration (FIG. 32A). Hydroxyproline was elevated in humanized NSG lungs (KB243 & KB004) relative to non-humanized mice (FIG. 32B). However, there was no significant difference in lung hydroxyproline (FIG. 32B), histological appearance (FIG. 32C-D) or CCR10⁺ cell numbers (FIG. 32E and quantified in 32F-G) between KB243 and KB004-treated groups. One explanation for the lack of a therapeutic effect of KB004 in this model pertains, in part, to the diminished numbers of human immune effector cells required for mAb-mediated ADCC of CCR10⁺ EphA3⁺cells in this model. The numbers of putative immune effectors T cells (introduced at the time of injection) were significantly diminished when enumerated at days 35 and 63 after IPF cell injection into NSG mice (FIG. 32I). Because of this finding, a separate group of NSG mice was therapeutically treated beginning at day 7 after IPF cell injection (FIG. 33A). Lung hydroxyproline was lower (FIG. 33B), histological interstitial consolidation was ameliorated (FIG. 33C-D) and a significant reduction in the number of $CD45^+$ $CCR10^+$ but not $Lin^-$ $CCR10^+$ (FIG. 33E-G) in KB004-compared to KB243-treated groups. It should be noted that neither KB243 or KB004 treatments in humanized NSG mice evoked inflammation in the mouse lung based upon findings from a Bioplex analysis for murine IL-2, IL-10, IL-12-p70, and TNFα (FIG. 34A-E). These results demonstrate that KB004-directed targeting of $CCR10^+$ IPF cells in humanized SCID mice was less efficacious therapeutically compared with its effects preventatively, possibly due to the loss of immune effector cells with time in this NSG mouse model of lung fibrosis.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc, As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

What is claimed is:

1. A method of determining the efficacy of a pulmonary fibrosis treatment, and optionally continuing to treat pulmonary fibrosis, comprising:
   obtaining a biological sample selected from whole blood, serum, plasma, peripheral blood mononuclear cells, immune cells or combinations thereof from a subject;
   detecting the number of CCR10-positive cells, the quantity of CCL28, or both in the biological sample when the biological sample is whole blood, plasma, peripheral blood mononuclear cells, and/or immune cells, or detecting the quantity of CCL28 when the biological sample is serum;
   comparing the number of CCR10-positive cells, or the quantity of CCL28, or both in the biological sample to the subject's baseline value or to a reference value;
   determining that the pulmonary fibrosis treatment is effective in the subject if the number of CCR10-positive cells, or quantity of CCL28, or both is the same as the subject's baseline value, is less than the subject's baseline value, or is less than the reference value, or
   determining that the pulmonary fibrosis treatment is ineffective in the subject if the number of CCR10-positive cells, or quantity of CCL28, or both is higher than the reference value.

2. The method of claim 1, wherein the method comprises continuing to treat pulmonary comprising:
   continuing to administer the pulmonary fibrosis treatment to a subject who has been determined that the pulmonary fibrosis treatment is effective.

3. A method of treating pulmonary fibrosis, comprising:
   requesting or obtaining the results regarding the number of CCR10-positive cells the quantity of CCL28, or both in a biological sample selected from whole blood, serum, plasma, peripheral blood mononuclear cells, immune cells or combinations thereof obtained from the subject;
   determining that a pulmonary fibrosis treatment is effective in the subject if the number of CCR10-positive cells, or quantity of CCL28, or both is the same as a subject's baseline value, is less than the subject's baseline value, or is less than a reference value, and continuing to administer the pulmonary fibrosis treatment, or
   determining that the pulmonary fibrosis treatment is ineffective in the subject if the number of CCR10-positive cells, or quantity of CCL28, or both is higher than the reference value, and stopping the administration of the pulmonary fibrosis treatment.

4. The method of claim 3, wherein the results are obtained by a method comprising:
   obtaining the biological sample from the subject;
   detecting the number of CCR10-positive cells, or quantity of CCL28, or both in the biological sample when the biological sample is whole blood, plasma, peripheral blood mononuclear cells, and/or immune cells, or detecting the quantity of CCL28 when the biological sample is serum.

5. A method of treating pulmonary fibrosis, comprising:
   continuing to administer a pulmonary fibrosis treatment to a subject who has been diagnosed that the pulmonary fibrosis treatment is effective by the method comprising:

detecting the number of CCR10-positive cells, or quantity of CCL28, or both in a biological sample obtained from the subject when the biological sample is whole blood, plasma, peripheral blood mononuclear cells, and/or immune cells, or detecting the quantity of CCL28 in the biological sample obtained from the subject when the biological sample is serum;

comparing the number of CCR10-positive cells, or the quantity of CCL28, or both in the biological sample to a reference value;

determining that the pulmonary fibrosis treatment is effective in the subject if the number of CCR10-positive cells, or the quantity of CCL28, or both is the same as the subject's baseline value, is less than the subject's baseline value, or is less than the reference value, wherein the biological sample is selected from whole blood, serum, plasma, peripheral blood mononuclear cells, immune cells or combinations thereof.

6. A method of predicting progression of pulmonary fibrosis, and selecting a pulmonary fibrosis treatment, comprising:

obtaining a biological sample selected from whole blood, serum, plasma, peripheral blood mononuclear cells, immune cells or combinations thereof from a subject;

detecting the number of CCR10-positive cells, the quantity of CCL28, or both in the biological sample when the biological sample is whole blood, plasma, peripheral blood mononuclear cells, and/or immune cells, or detecting the quantity of CCL28 when the biological sample is serum;

comparing the number of CCR10-positive cells, quantity of CCL28, or both in the biological sample to a reference value;

predicting a faster progression of pulmonary fibrosis if the number of CCR10-positive cells, quantity of CCL28, or both are higher than the reference value, or predicting a slower progression of pulmonary fibrosis if the number of CCR10-positive cells, quantity of CCL28, or both are lower than the reference value; and selecting an experimental treatment if the subject is predicted to have a faster progression of pulmonary fibrosis, or selecting a standard pulmonary fibrosis treatment if the subject is predicted to not have a faster progression of pulmonary fibrosis.

7. The method of claim 6, wherein the pulmonary fibrosis is idiopathic pulmonary fibrosis (iPF).

8. The method of claim 6, wherein the experimental pulmonary fibrosis treatment is an anti-EphA3 antibody.

9. The method of claim 6, wherein the experimental pulmonary fibrosis treatment is antibody KB004.

10. A method of detecting resistance to nintedanib in a subject having idiopathic pulmonary fibrosis, comprising:

detecting whether the number of CCR10+cells in a subject having or suspected of having pulmonary fibrosis is higher or lower than the subject's baseline value or a reference value by detecting the number of CCR10-positive cells in a biological sample from the subject;

comparing the number of CCR10-positive cells in the biological sample to the subject's baseline value or to a reference value; and determining whether the number of CCR10-positive cells in the biological sample is higher or lower than the subject's baseline value or the reference value; and determining resistance to nintedanib if the number of CCR10-positive cells in the biological sample is higher than subject's baseline value or the reference value.

11. The method of claim 10, further comprising first obtaining the biological sample from the subject having or suspected of having pulmonary fibrosis.

12. The method of claim 10, wherein detecting the number of CCR10-positive cells comprises using an assay selected from the group consisting of flow cytometry, enzyme-linked immunosorbent assay (ELISA), immunohistochemistry, fluorescence in situ hybridization (FISH), radioimmuno assay, and affinity purification, transcript analysis, qPCR, RNA sequencing, and affymetrix array.

13. The method of claim 10, further comprising administering an anti-EphA3 antibody.

14. The method of claim 10, further comprising administering KB004.

* * * * *